US010611786B2

(12) United States Patent
White et al.

(10) Patent No.: US 10,611,786 B2
(45) Date of Patent: Apr. 7, 2020

(54) MANGANESE (III) CATALYZED C—H AMINATIONS

(71) Applicant: The Board of Trustees of the University of Illinois, Urbana, IL (US)

(72) Inventors: M. Christina White, Champaign, IL (US); Joseph R. Clark, Milwaukee, WI (US); Kaibo Feng, Urbana, IL (US); Anasheh Sookezian, King of Prussia, PA (US); Chloe Wendell, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/153,178

(22) Filed: Oct. 5, 2018

(65) Prior Publication Data
US 2019/0106448 A1    Apr. 11, 2019

Related U.S. Application Data

(60) Provisional application No. 62/569,872, filed on Oct. 9, 2017.

(51) Int. Cl.
*C07D 487/22* (2006.01)
*C07F 13/00* (2006.01)
(Continued)

(52) U.S. Cl.
CPC .......... *C07F 13/005* (2013.01); *B01J 31/183* (2013.01); *B01J 31/26* (2013.01); *C07C 303/34* (2013.01); *C07D 207/20* (2013.01); *C07D 209/58* (2013.01); *C07D 209/60* (2013.01); *C07D 209/88* (2013.01); *C07D 211/28* (2013.01); *C07D 215/42* (2013.01); *C07D 221/10* (2013.01); *C07D 221/20* (2013.01); *C07D 235/06* (2013.01); *C07D 263/12* (2013.01); *C07D 307/87* (2013.01); *C07D 311/76* (2013.01); *C07D 487/22* (2013.01); *C07D 493/22* (2013.01); *C07D 499/04* (2013.01); *C07F 11/005* (2013.01); *C07J 41/0005* (2013.01); *C07J 43/003* (2013.01);
(Continued)

(58) Field of Classification Search
CPC .................................................. C07D 487/22
See application file for complete search history.

(56) References Cited

U.S. PATENT DOCUMENTS 5,817,877 A    10/1998 Hartwig et al.
6,307,087 B1    10/2001 Buchwald et al.
(Continued)

FOREIGN PATENT DOCUMENTS

EP    2099749 B1    9/2015
JP    2006057014 A    3/2006
WO    2007059015 A1    5/2007
WO    2010028159 A2    3/2010

OTHER PUBLICATIONS

Liu et al. Journal of Molecular Catalysis A: Chemical 246 (2006), 49-52.*
Petkov et al. (Applied Surface Science, 2016, 379, 415-423).*
Chen et al., "A Predictably Selective Aliphatic C—H Oxidation Reaction for Complex Molecule Synthesis," Science, 318(5851):783-787, Nov. 2007.
Dolotova et al., Zhurnal Obshchei Khimii (Russian Journal of General Chemistry), 58(9):2173,1988.
Dolotova et al., Zhurnal Obshchei Khimii (Russian Journal of General Chemistry), 62(9):2064-75, 1992.
Fürstner, A., "Alkene Metathesis in Organic Synthesis (Topics in Organometallic Chemistry)," 1, 1998, 7pgs.
(Continued)

*Primary Examiner* — Brian E McDowell
(74) *Attorney, Agent, or Firm* — Haukaas Fortius PLLC; Michael H. Haukaas

(57) ABSTRACT

Reactions that directly install nitrogen into C—H bonds of complex molecules are significant because of their potential to change the chemical and biological properties of a given compound. Selective intramolecular C—H amination reactions that achieve high levels of reactivity, while maintaining excellent site-selectivity and functional-group tolerance is a challenging problem. Herein is reported a manganese perchlorophthalocyanine catalyst [$Mn^{III}(ClPc)$] for intermolecular benzylic C—H amination of bioactive molecules and natural products that proceeds with unprecedented levels of reactivity and site-selectivity. In the presence of Brønsted or Lewis acid, the [$Mn^{III}(ClPc)$]-catalyzed C—H amination demonstrates unique tolerance for tertiary amine, pyridine and benzimidazole functionalities. Mechanistic studies indicate that C—H amination proceeds through an electrophilic metallonitrene intermediate via a stepwise pathway where C—H cleavage is the rate-determining step of the reaction. Collectively these mechanistic features contrast previous base-metal catalyzed C—H aminations. The catalyst can be a compound of Formula I:

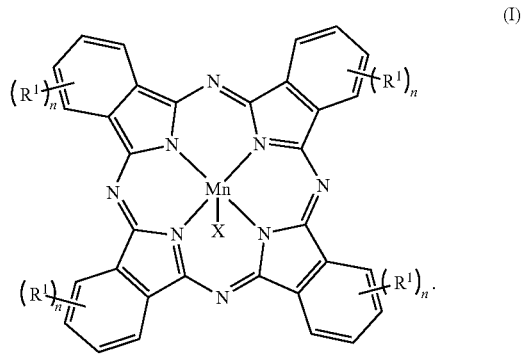

8 Claims, 5 Drawing Sheets

(51) Int. Cl.

| | | |
|---|---|---|
| C07D 311/76 | (2006.01) | |
| C07D 215/42 | (2006.01) | |
| C07D 209/88 | (2006.01) | |
| C07D 207/20 | (2006.01) | |
| C07D 263/12 | (2006.01) | |
| C07D 221/20 | (2006.01) | |
| C07D 211/28 | (2006.01) | |
| C07D 209/58 | (2006.01) | |
| C07D 307/87 | (2006.01) | |
| C07D 221/10 | (2006.01) | |
| C07D 499/04 | (2006.01) | |
| C07D 209/60 | (2006.01) | |
| C07D 235/06 | (2006.01) | |
| C07D 493/22 | (2006.01) | |
| C07J 41/00 | (2006.01) | |
| C07J 43/00 | (2006.01) | |
| B01J 31/18 | (2006.01) | |
| B01J 31/26 | (2006.01) | |
| C07C 303/34 | (2006.01) | |
| C07F 11/00 | (2006.01) | |

(52) U.S. Cl.
CPC .... *B01J 2231/4283* (2013.01); *B01J 2231/44* (2013.01); *B01J 2531/72* (2013.01)

(56) References Cited

U.S. PATENT DOCUMENTS

| 7,829,342 | B2 | 11/2010 | White et al. |
| 7,871,855 | B2* | 1/2011 | Yan ..................... C09B 47/045 |
| | | | 257/E51.024 |
| 9,770,711 | B2 | 9/2017 | White et al. |
| 9,925,528 | B2 | 3/2018 | White et al. |
| 2004/0087820 | A1 | 5/2004 | Fuchs et al. |
| 2009/0093638 | A1 | 4/2009 | Doyle et al. |
| 2009/0221083 | A1 | 9/2009 | White et al. |
| 2010/0063277 | A1 | 3/2010 | Zhang et al. |
| 2011/0015397 | A1 | 1/2011 | White et al. |
| 2012/0190635 | A1 | 7/2012 | Li et al. |
| 2013/0184494 | A1 | 7/2013 | Kurosawa et al. |

OTHER PUBLICATIONS

Gormisky et al., "Catalyst-Controlled Aliphatic C—H Oxidations with a Predictive Model for Site Selectivity," J. Am. Chem. Soc., 135(38):14052-14055, Sep. 2013.

Groves et al., "Hydrocarbon Oxidations with Oxometalloporphinates. Isolation and Reactions of a (porphinato) Manganese(V) Complex," J. Am. Chem. Soc., 102(20):6375-6377, Sep. 1980.

Groves et al., "Synthesis, Characterization, and Reactivity of Oxomanganese(IV) Porphyrin Complexes," J. Am. Chem. Soc., 110(26):8628-8638, Dec. 1988.

Gustafson et al., "Linear Free Energy Relationship Analysis of a Catalytic Desymmetrization Reaction of a Diarylmethane-Bis(Phenol)," Org. Lett., 12(12):2794-2797, May 2010.

Harper et al., "Three-Dimensional Correlation of Steric and Electronic Free Energy Relationships Guides Asymmetric Propargylation," Science, 333(6051):1875-1878, Sep. 2011.

Howell et al., "Remote Oxidation of Aliphatic C—H Bonds in Nitrogen-Containing Molecules," J Am Chem Soc., 137(46):14590-14593, Nov. 2015.

International Search Report and Written Opinion of the ISA/US dated Dec. 4, 2014 in International Application No. PCT/US2014/054835; 10pgs.

Knecht et al., "Synthesis and Properties of Soluble Phthalocyaninatomanganese(III) Complexes," J. Porphyrins Phthalocyanines; 3:292-298; Apr. 1999.

Paradine et al., "A Manganese Catalyst for Highly Reactive yet Chemoselective Intramolecular C(Sp3)—H Amination," Nat. Chem., 7:987-994, Oct. 2015.

Paradine et al., "Iron-Catalyzed Intramolecular Allylic C—H Amination," J. Am. Chem. Soc., 134(4):2036-2039, Jan. 2012.

Ruppel et al., "Cobalt-Catalyzed Intramolecular C—H Amination with Arylsulfonyl Azides," Org. Lett., 9(23):4889-4892, Oct. 2007.

* cited by examiner

MANGANESE (III) CATALYZED C—H AMINATIONS

RELATED APPLICATIONS

This application claims priority under 35 U.S.C. § 119(e) to U.S. Provisional Patent Application No. 62/569,872, filed Oct. 9, 2017, which is incorporated herein by reference.

GOVERNMENT SUPPORT

This invention was made with government support under Grant No. GM122525 awarded by the National Institutes of Health. The government has certain rights in the invention.

BACKGROUND OF THE INVENTION

Introduction of nitrogen into natural products and biologically active small molecules has the potential to drastically change the physical and biological properties of a given molecule. For example, ampicillin, the first broad-spectrum penicillin derivative, differs from penicillin G by the presence of a benzylic amine (FIG. 1a). In fact, the importance of nitrogen in the benzylic position of pharmacophores can be gleaned by its appearance in top-selling FDA-approved drugs such as imatinib, meclizine, clopidogrel, sertraline, rivastigmine and donepezil, as well as many others. In nature, such nitrogen functionality is installed through oxygenated intermediates. For example, in the biosynthesis of 1-p-hydroxyphenylglycine, a crucial component of several peptidic natural products, the benzylic amine is installed from the benzylic ketone. Analogously, standard synthetic methods to install nitrogen rely on functional group transformations from pre-oxidized carbon-heteroatom (C—O, C—X, X=halogens) precursors. This approach limits the direct installation of nitrogen into topologically and functionally complex molecules, often necessitating de novo syntheses. The ability to effect late-stage functionalization via direct and selective installation of nitrogen in complex molecules may expedite discovery processes for biologically active small molecules and re-invigorate the exploration of natural-product-derived drug candidates.

Significant reactivity and selectivity challenges exist in the late-stage C—H amination of natural products and pharmaceuticals, as many similar C—H bond types may be present in a molecule. Noble-metal rhodium catalysis via metallonitrene intermediates is well established for the intramolecular C—H amination of a wide range of C—H bond types. One advantage of proceeding via metallonitrene intermediates is that both C—H cleavage and functionalization are tightly regulated at the metal and therefore are amenable to tuning via ligand/metal modifications. Intermolecular rhodium-catalyzed C—H aminations are emerging for benzylic, tertiary and allylic C—H aminations; however, chemo- and site-selectivity challenges exist in molecules with multiple reactive functionalities or C—H bonds. For example, in molecules with both tertiary and benzylic C—H bonds, inseparable product mixtures are formed (FIG. 1b). Moreover, the ability to effect remote C—H amination in molecules with basic amines or heterocyclic functionality has not been demonstrated for this type of C—H amination (FIG. 1c). Tertiary amine-containing natural products undergo α-amination/oxidation sequences to give amidines or direct N-amination to furnish hydrazine sulfamate zwitterions, with protection of nitrogen as an amine salt not shown to be tolerated.

Base-metal catalysts have emerged for highly selective intramolecular C—H aminations; however, analogous intermolecular processes are scarce. For example, cobalt-catalyzed intermolecular benzylic C—H aminations are not suitable for late-stage applications as they have formidable reactivity challenges requiring solvent quantities of substrates (FIG. 1d), and intramolecular processes do not appear to discriminate between C—H bonds based on electronic properties (FIG. 1e). Copper-catalyzed processes can have significant site- and chemoselectivity issues, furnishing mixtures of aminated products with substrates as simple as ethylbenzene. Iron- and manganese-catalyzed intermolecular C—H azidations have been reported to have tolerance for nitrogen heterocyclic functionality, but these proceed via free-radical pathways that result in poor site selectivities and long-lived substrate radicals that scramble the stereochemistry and may lead to skeletal rearrangements (FIG. 1f).

Accordingly, there is a need for a reagent that can selectively catalyze intermolecular C—H aminations in the presence of other functionalities.

SUMMARY

Herein we report a manganese perchlorophthalocyanine [$Mn^{III}$(ClPc)] catalyst for a highly site-selective and functional-group-tolerant intermolecular benzylic C($sp^3$)-H amination. This methodology enables preparative base-metal nitrene-mediated late-stage amination on a broad range of natural products and pharmaceuticals, including ones containing multiple benzylic sites and basic nitrogen (tertiary amines, pyridines and benzimidazole) functionality.

Accordingly, this disclosure provides a compound of Formula I:

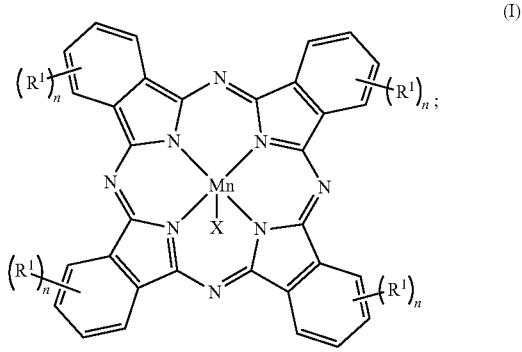

wherein
X is an anion;
each $R^1$ is independently an electron withdrawing group; and
each n is independently 1, 2, 3, or 4.

This disclosure also provides various embodiments of Formula I wherein:
each $R^1$ is independently halo, —C(=O)$R^2$, —S(=O)$_2$$R^3$, —C≡C$R^4$, —C$Q_3$, or —C$Q_2$C$Q_3$;
$R^2$ is H, —C$Q_3$, —($C_1$-$C_6$)alkyl, O$R^5$, N($R^5$)$_2$, or phenyl;
$R^3$ is —C$Q_3$, —($C_1$-$C_6$)alkyl, N($R^5$)$_2$, or phenyl;
$R^4$ is H, halo, —C$Q_3$, —($C_1$-$C_6$)alkyl, or phenyl;
Q is choro or fluoro; and
each $R^5$ is independently H, or —($C_1$-$C_6$)alkyl;
wherein optionally each phenyl is independently substituted with 1-5 substituents.

Additionally, this disclosure provides a composition comprising a compound of Formula I and a salt.

Furthermore, this disclosure also provides a method for forming a C—N bond comprising contacting an organic substrate, a nitrogen-containing oxidant, and a compound of Formula I, in a solvent to form a mixture, wherein a C—H moiety of the organic substrate is aminated, thereby forming a C—N bond.

The invention provides novel compounds of Formula I and Formula II, intermediates for the synthesis of compounds of Formula I and Formula II, as well as methods of preparing compounds of Formula I and II. The invention also provides compounds of Formula I and II that are useful as intermediates for the synthesis of other useful compounds.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
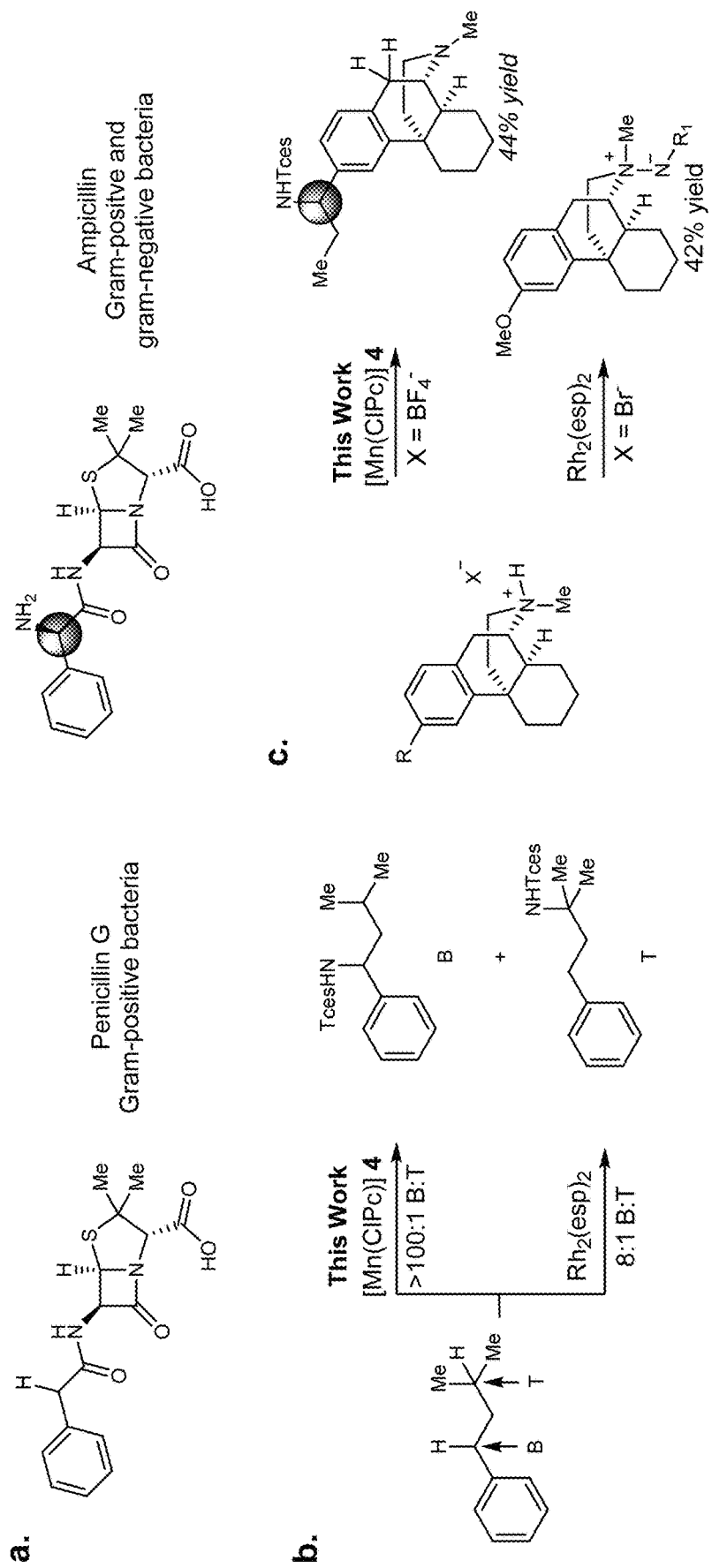
FIG. 1. Converting C—H bonds to C—N bonds. a, Ampicillin, a broad-spectrum antibacterial drug, differs from penicillin G by an atomistic change of a benzylic C—H to C—N. b, Comparison of site selectivities for benzylic versus tertiary C—H amination of Mn-versus Rh-catalyzed C—H aminations. Tces: 2,2,2-trichloroethoxysulfonyl. esp: α,α,α',α'-tetramethyl-1,3-benzenedipropionate. c, Chemoselectivity in a tertiary amine containing natural product in Mn-versus Rh-catalyzed C—H aminations. d, Comparison of reactivity of Mn-versus Co-catalyzed benzylic C—H aminations. $^a$Yield based on equivalents of substrate used. $^b$Yield based on equivalents of oxidant used. Troc: 2,2,2-trichloroethoxycarbonyl. e, Observed site-selectivity of Mn-versus Co-catalyzed C—H aminations. f, Comparison of site selectivities among sterically differentiated benzylic C—H bonds on estrone/estradiol derivatives of a Mn-catalyzed reaction proceeding via a metallonitrene with previously reported Fe-catalyzed C—H azidation proceeding via a free-radical intermediate.
Figure 1:
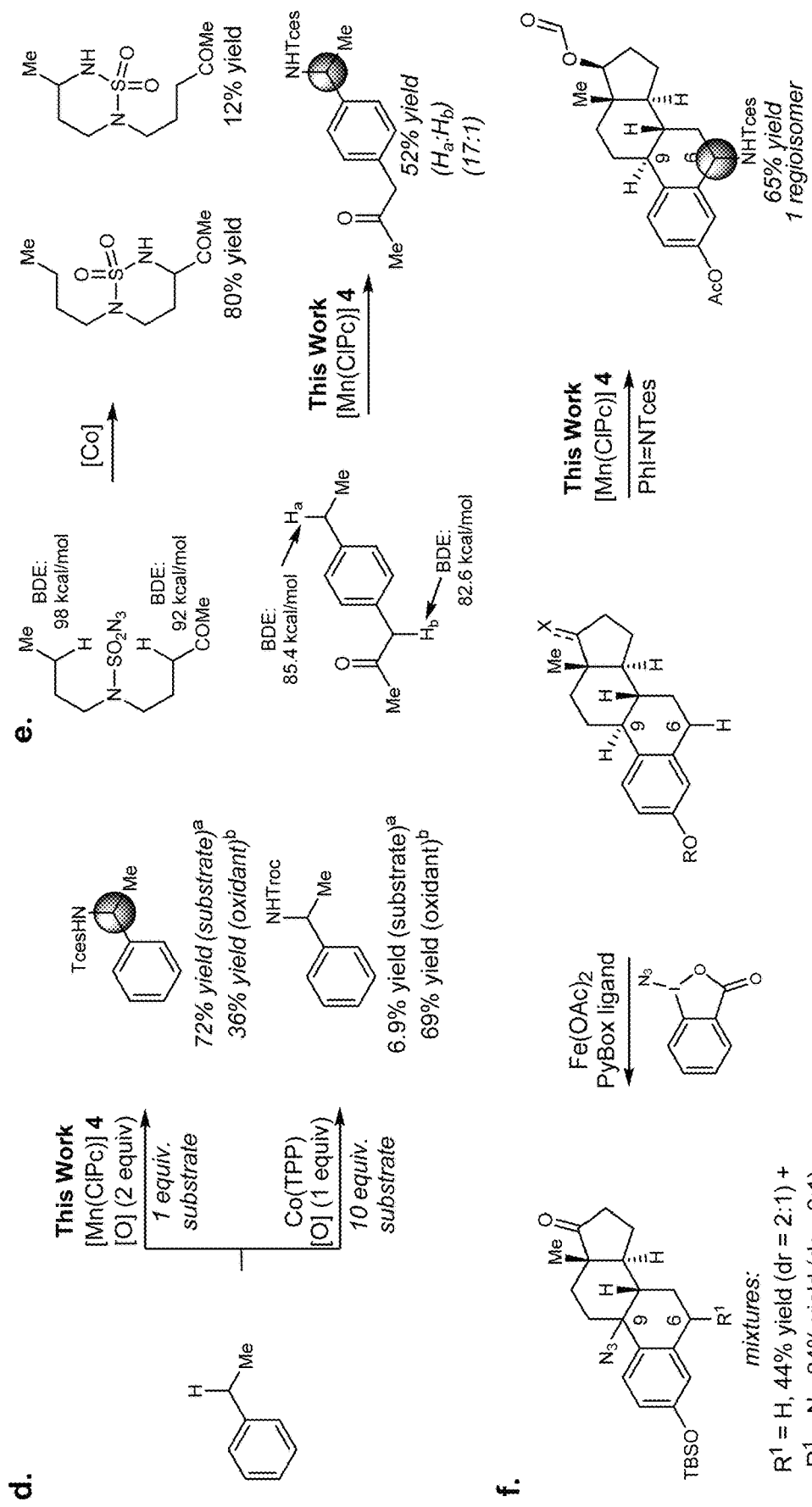
Figure 2:
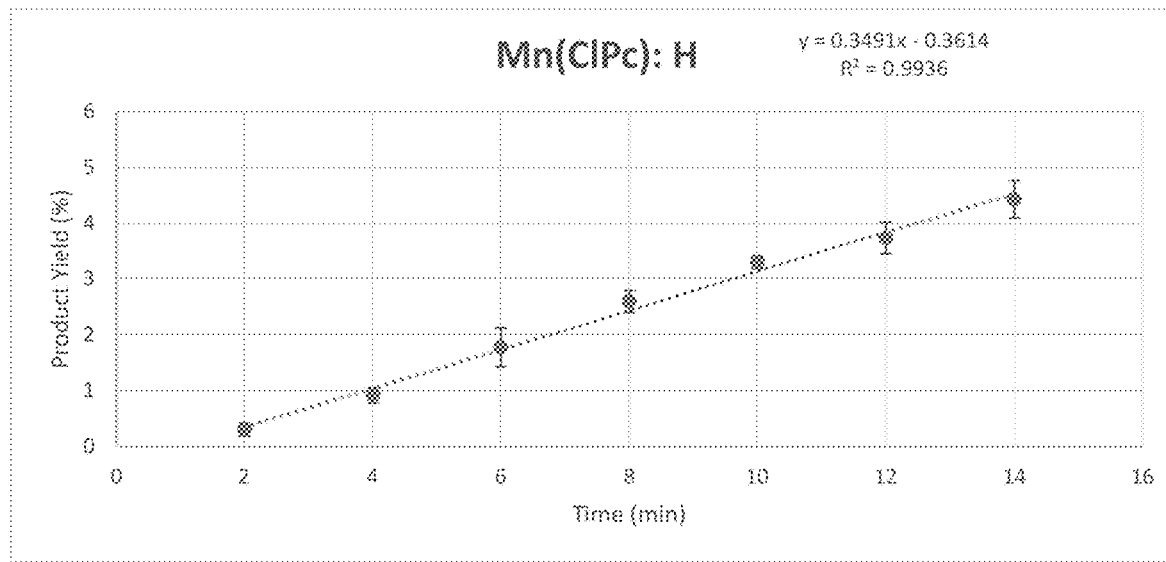
FIG. 2. Determination of $k_H$.
Figure 3:
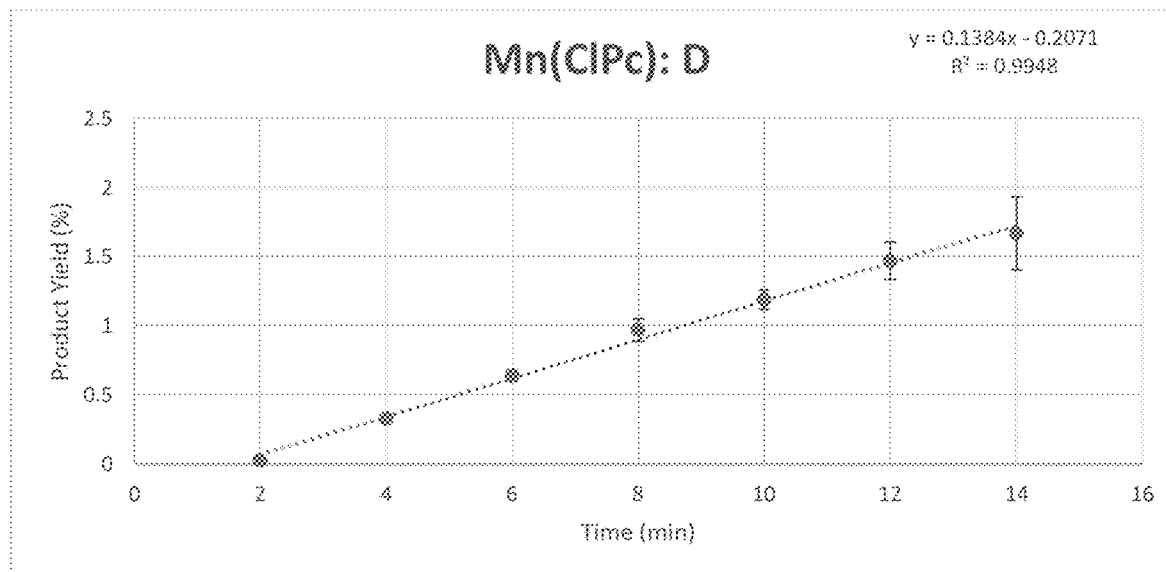
FIG. 3. Determination of $k_D$.
Figure 4:
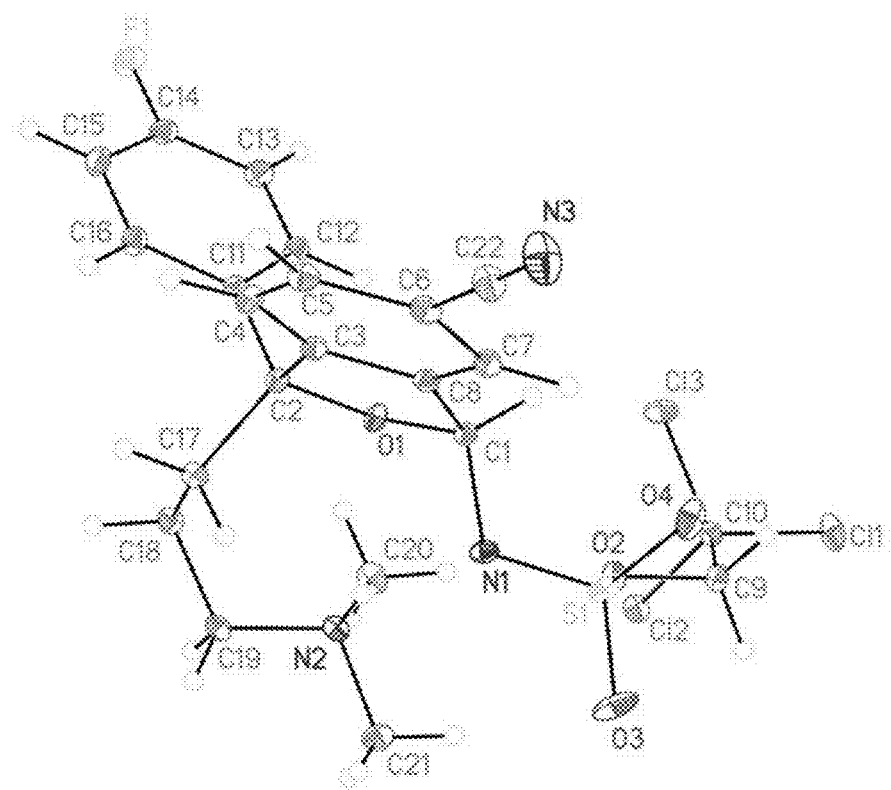
FIG. 4. X-ray crystal structure analysis of aminated citalopram (±)36.
Figure 5:
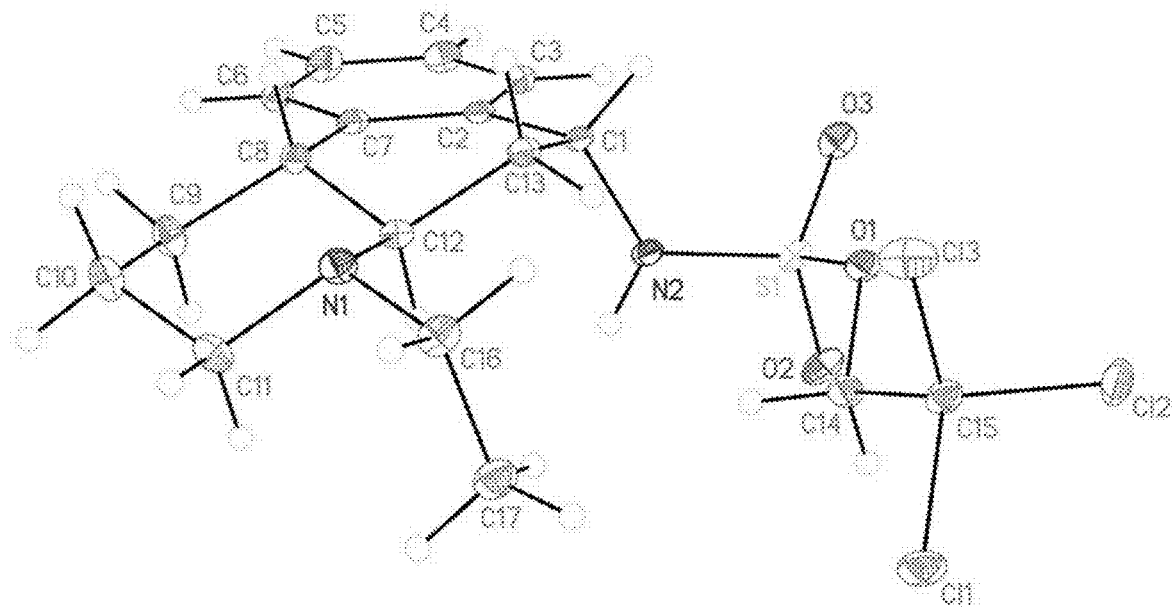
FIG. 5. X-ray crystal structure analysis of aminated dopamine receptor agonist (±)37.
Figure 6:
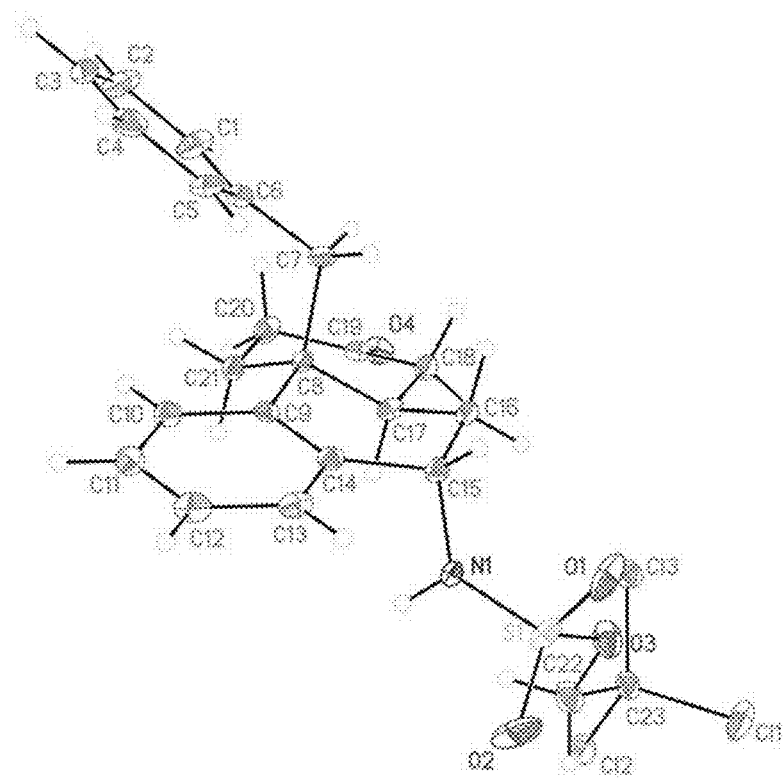
FIG. 6. X-ray crystal structure analysis of aminated glucocorticoid receptor agonist (−)38.
Figure 7:
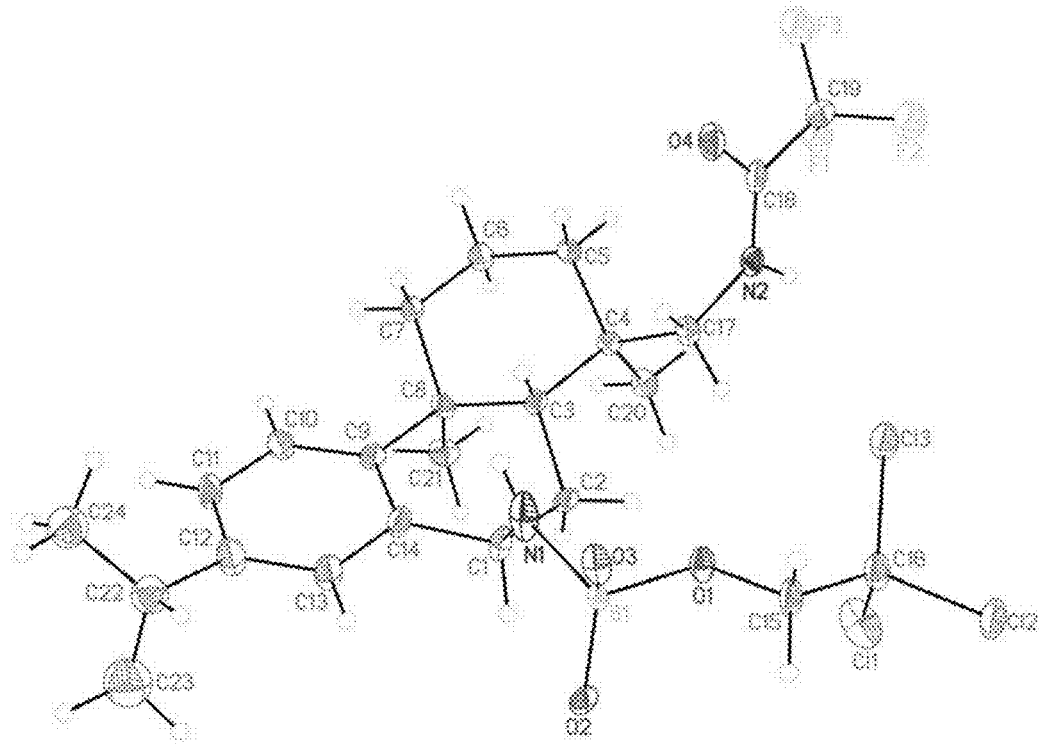
FIG. 7. X-ray crystal structure analysis of aminated leelamine (−)44.

A base-metal-catalyzed intermolecular benzylic C—H amination is reported that proceeds with unprecedented levels of reactivity, site selectivity and functional group tolerance. The [Mn$^{III}$(ClPc)] 4 catalyst is synthesized in a one-step, scalable reaction from abundant and sustainable commercial starting materials. The [Mn$^{III}$(ClPc)] 4-catalyzed C—H amination demonstrates high site selectivity in molecules containing multiple reactive C—H bonds based on steric and electronic differentiation. Moreover, the catalyst is compatible with both Brønsted and Lewis acid complexed basic nitrogen functionality, enabling remote C—H amination in molecules containing tertiary amines and heterocycles that cannot effectively be masked via alternative methods. Collectively, the combination of reactivity and selectivity makes this [Mn$^{III}$(ClPc)] 4-catalyzed intermolecular benzylic C(sp$^3$)-H amination uniquely effective at late-stage functionalization of bioactive molecules and natural products. Mechanistic studies suggest that this method proceeds via a stepwise C—H amination pathway with C—H cleavage as the rate-determining step. A competition study and empirical data on the impact of electronic effects on site selectivities suggest that the nature of the key intermediate is that of an electrophilic metallonitrene. Collectively, these features significantly contrast with other base-metal-catalyzed C—H aminations that are poorly reactive intermolecularly and generally proceed via intermediates with more free-radical character that exhibit less control on site selectivity. The high reactivity and selectivity of this reaction make it uniquely effective for late-stage installation of valuable nitrogen functionality in complex molecule settings. Moreover, the mechanistic features enable tunable control of site selectivity when the reactivity is increased for intermolecular amination of other C(sp$^3$)-H bond types.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983).

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'2)$_n$ wherein n is 1, 2, 3, or more, and each R$^1$ is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, 3-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Embodiments of the Invention

This disclosure provides various embodiments of a compound of Formula I:

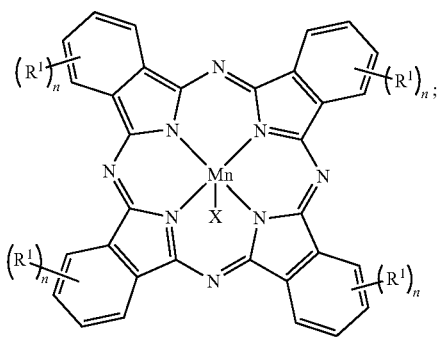

(I)

wherein
X is an anion;
each $R^1$ is independently an electron withdrawing group; and
each n is independently 1, 2, 3, or 4.

Various additional embodiments of Formula I are encompassed by this disclosure, wherein:
  each $R^1$ is independently halo, —C(=O)$R^2$, —S(=O)$_2$$R^3$, —C≡C$R^4$, —C$Q_3$, or —C$Q_2$C$Q_3$;
  $R^2$ is H, —C$Q_3$, —($C_1$-$C_6$)alkyl, O$R^5$, N($R^5$)$_2$, or phenyl;
  $R^3$ is —C$Q_3$, —($C_1$-$C_6$)alkyl, N($R^5$)$_2$, or phenyl;
  $R^4$ is H, halo, —C$Q_3$, —($C_1$-$C_6$)alkyl, or phenyl;
  Q is choro or fluoro; and
  each $R^5$ is independently H, or —($C_1$-$C_6$)alkyl;
  wherein optionally each phenyl is independently substituted with 1-5 substituents.

In some embodiments, X is halo or Sb$F_6$. In other embodiments, $R^1$ is halo. In further embodiments, $R^1$ is chloro. In yet other embodiments, n is 3 or 4; or n is 2 or 3; or n is 4. In some other embodiments, the compound of Formula I is a compound of Formula II:

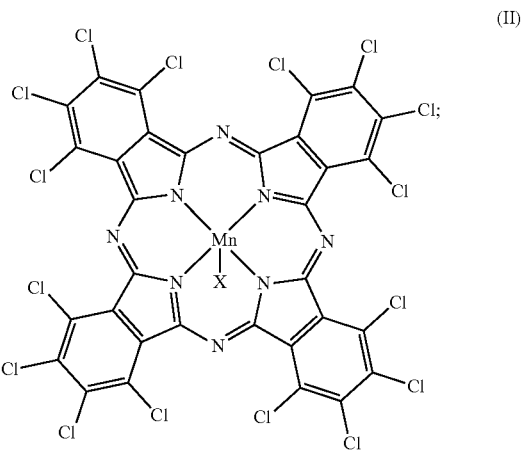

(II)

wherein X is Cl or Sb$F_6$.

This disclosure also provides a composition comprising a compound of Formula I and a salt. In some embodiments, the salt is AgSb$F_6$. In other embodiments, the composition comprises a compound of Formula I and a solvent, such as, for example, water, toluene, benzene, dichloroethane, etc. In other embodiments, the composition comprises the compound 3:

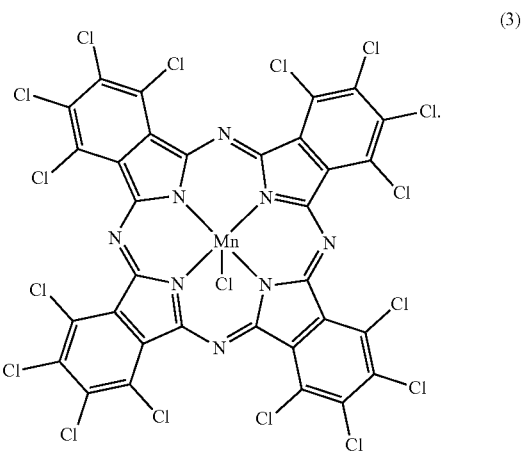

(3)

This disclosure further provides a method for forming a C—N bond comprising contacting an organic substrate, a nitrogen-containing oxidant, and a compound of Formula I described herein, in a solvent to form a mixture, wherein a C—H moiety of the organic substrate is aminated, thereby forming a C—N bond. In various embodiments, the nitrogen-contain oxidant comprises, for example, a sulfonate, tosylate, or carbamate. In some embodiments the oxidant is an iminoiodinane. In other embodiments, the iminoiodinane is formed in situ. In yet other embodiments, the iminoiodinane is 2,2,2-trichloroethyl (phenyl-$\lambda^3$-iodanylidene)sulfamate.

In yet further embodiments, the oxidant and the compound of Formula I described herein form a metallonitrene catalyst. In additional embodiments, the compound of Formula I described herein is manganese (III) perchlorophthalocyanine chloride (3). In some additional embodiments, the mixture described above further comprises silver hexafluoroantimonate. In some other embodiments, the C—H moiety described above is electron rich.

In various embodiments of the disclosed method, the organic substrate is intermolecularly (or is intramolecularly) and selectively aminated at the most electron rich and sterically accessible C—H moiety (e.g. the C—H moiety aminated is the least hindered or is unhindered by proximal (nearby) substituents that block (or deflect) the catalyst from approaching the organic substrate (molecule). In other embodiments, the carbon atom of the C—H moiety is a primary carbon (1°), secondary carbon (2°), or tertiary carbon (3°). In yet other embodiments, the C—H moiety is at a benzylic position.

In other embodiments, the organic substrate is an organic molecule having a basic nitrogen atom, for example, the basic nitrogen atom is in a molecule comprising an alkyl amine, a pyridine, an imidazole, etc. In further embodiments, the mixture further comprises a Brønsted acid or a Lewis acid. In yet some other embodiments, the Brønsted acid or the Lewis acid comprises $HBF_4$ or $BF_3$. In further embodiments, the Brønsted acid or the Lewis acid comprises a complex, such as, for example, a solvent complex.

Some aspects of the disclosure include a method of intermolecular (or intramolecular)C—H amination, the method comprising:

incubating a mixture comprising a compound of Formula I or a composition disclosed anywhere herein, a target substrate, an oxidant, and a solvent at a temperature of about 20° C. to about 40° C. for about 8 hours to about 16 hours.

In various aspects of the full disclosure, the solvent is a polar aprotic solvent. In other aspects, the solvent is selected from benzene, 1,2-dicholorethane, methylene chloride, pentane, chlorobenzene, chloroform and isopropyl acetate. In additional aspects the oxidant is a preformed iminoiodinane. In yet other aspects, the preformed iminoiodinane is selected from 2,2,2-trichloroethyl suflamate ($TcesNH_2$) and PhI$(OAc)_2$ (PhI=NTces), 2,2,2-trifluoroethyl sulfamate and PhI$(OAc)_2$, hexafluoroisopropyl sulfamate and PhI$(OAc)_2$, p-fluorophenyl sulfamate and PhI$(OAc)_2$, p-trifluoromethylphenyl sulfonamide and PhI$(OAc)_2$, p-chlorophenyl sulfonamide and PhI(OAc)2, 2,2-dichloroethyl sulfamate and PhI$(OAc)_2$ and 2-chloroethyl sulfamate and PhI$(OAc)_2$.

In some other aspects of the methods described herein, the described oxidant is present at about 1.0 equivalent to about 3.0 equivalents. In other aspects, the disclosed composition is present in an amount of about 5 mol % to about 15 mol %. In additional aspects, the disclosed methods comprise protonating the target substrate with $HBF_4 \cdot OEt_2$ or complexing the target with $BF_3 \cdot OEt_2$. In yet other aspects, the methods have high site-selectivity in molecules containing multiple reactive C—H bonds.

In additional aspects, the methods have an amination preference for the least sterically encumbered and most electron-rich site. In other aspects, the methods are effective at late stage functionalization of bioactive molecules and natural products.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above.

Similarly, if the variable disclosed is a number greater than "number10", it implies a continuous range that includes whole numbers and fractional numbers greater than number10. These ranges can be modified by the term "about", whose meaning has been described above.

Results and Discussion

Reaction Development

Reaction development commenced by examining commercially available first-row transition metal catalysts previously demonstrated to be effective in intramolecular C—H amination via metallonitrene intermediates. The combination of 2,2,2-trichloroethyl sulfamate ($TcesNH_2$) and PhI$(OPiv)_2$ oxidant in the presence of iron phthalocyanine gave no product, whereas manganese phthalocyanines gave trace product (Table 1, entries 1-4). In the presence of cobalt(II) tetraphenylporphyrin ($Co^{II}$(TPP)), no reactivity was observed under in situ iminoiodinane conditions or previously reported TrocN3 conditions (entry 5). Mechanistic studies for intramolecular C—H amination processes promoted by manganese phthalocyanines suggested that in situ formation of iminoiodinane, an equilibrium process that favors the sulfamate ester, may be partially rate-determining.

Examining if elimination of this step could enhance the reactivity by using preformed iminoiodinane (PhI=NTces) gave improved yields of benzylic amination across all the phthalocyanine catalysts examined, with [$Mn^{III}$(Pc)]SbF$_6$ giving the best results (entries 6-8). The use of a non-coordinating hexafluoroantimonate ($SbF_6^-$) counterion is thought to increase reactivity in these systems by furnishing a cationic metal complex with enhanced electrophilicity.

It was hypothesized that electron-withdrawing ligand modifications may promote the formation of an electrophilic metallonitrene that is more reactive towards intermolecular C—H amination. Gratifyingly, a novel perchlorinated manganese phthalocyanine catalyst [$Mn^{III}$(ClPc)]4 (4=[$Mn^{III}$(Cl$_{16}$Pc)]SbF$_6$), readily accessed in one step from commercial reagents, significantly improved the yield of the desired amination to 53% (Table 1 entry 9, Scheme 1a). Increasing the reaction temperature from 23 OC to 40° C. further increased the yield of aminated product to 68% (entry 10). Lowering the catalyst loading to 5 mol % or cutting the PhI=NTces to 1.0 equiv. led to 47% and 42% yields, respectively (entries 11 and 12). Replacing the benzene solvent with 1,2-dichloroethane, a polar aprotic solvent compatible with polar substrates and complex molecules (vide infra), gave a synthetically useful 60% yield (entry 13).

In the absence of AgSbF$_6$, a synthetically useful 50% yield is still obtained (entry 14), whereas elimination of [$Mn^{III}$(ClPc)] 4 resulted in no product formation (entry 15). Re-examination of $Co^{II}$(TPP) with iminoiodinane under the optimal [$Mn^{III}$(ClPc)] 4 conditions did not lead to a productive reaction (entry 16). In situ iminoiodinane formation under these optimal conditions was unproductive (entry 17). It is important to note, however, that iminoiodinane (PhI=NTces) can be readily synthesized from commercial starting materials and, upon isolation, can be stored for months. Interestingly, using preformed iminoiodinane for rhodium-catalyzed intermolecular benzylic C—H amination was reported (*J. Am. Chem. Soc.* 2007, 129, 562) to result in a significant decrease in yield relative to the in situ method.

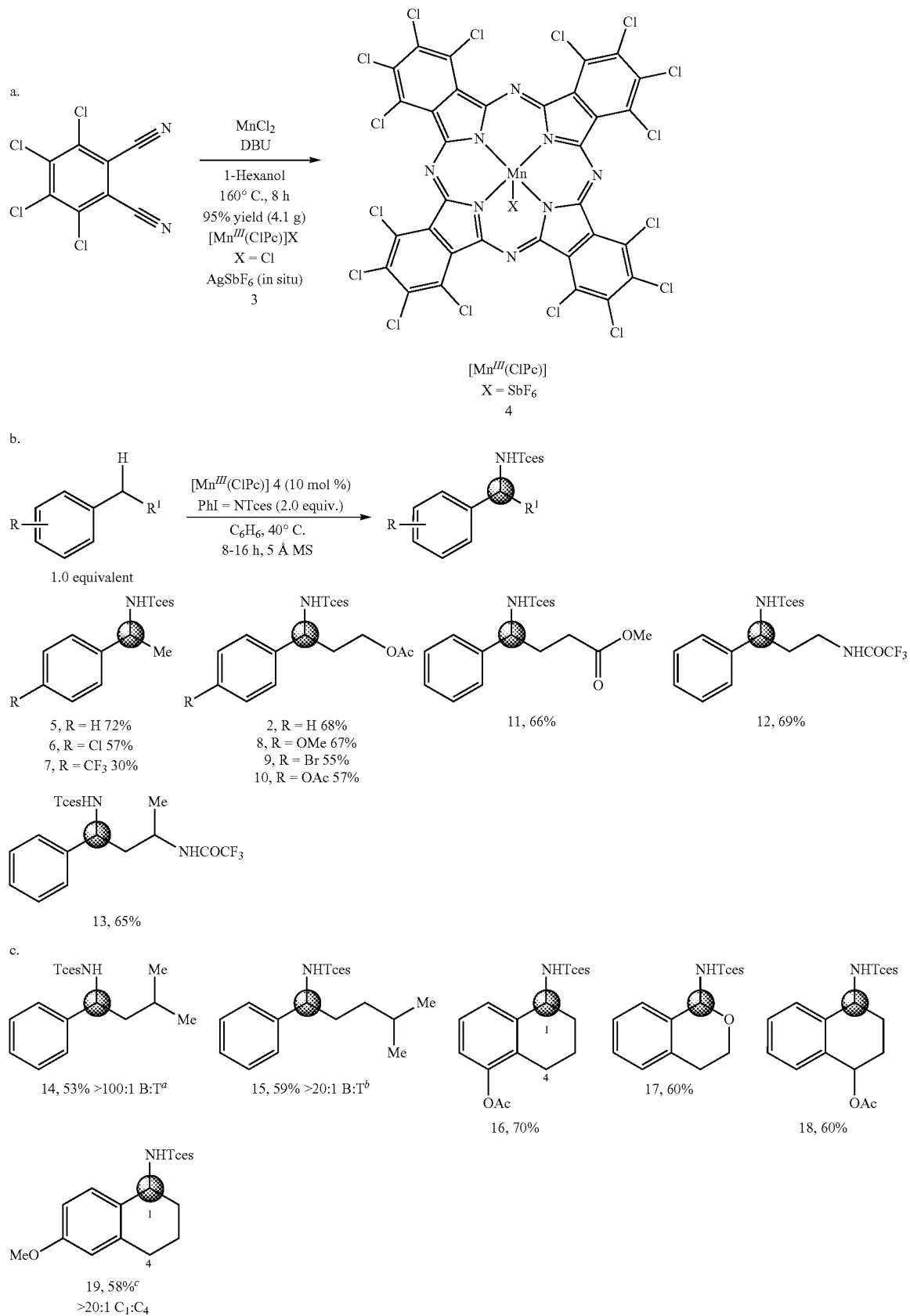
Scheme 1. Intermolecular benzylic C—H amination substrate scope.

d.

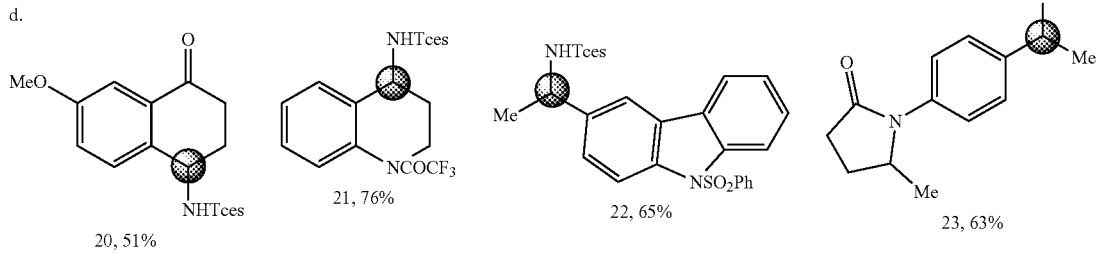

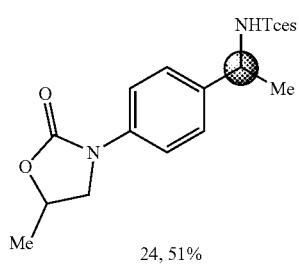

e.

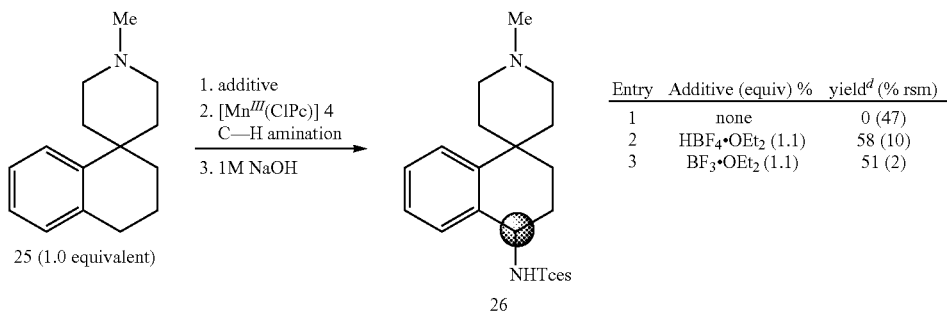

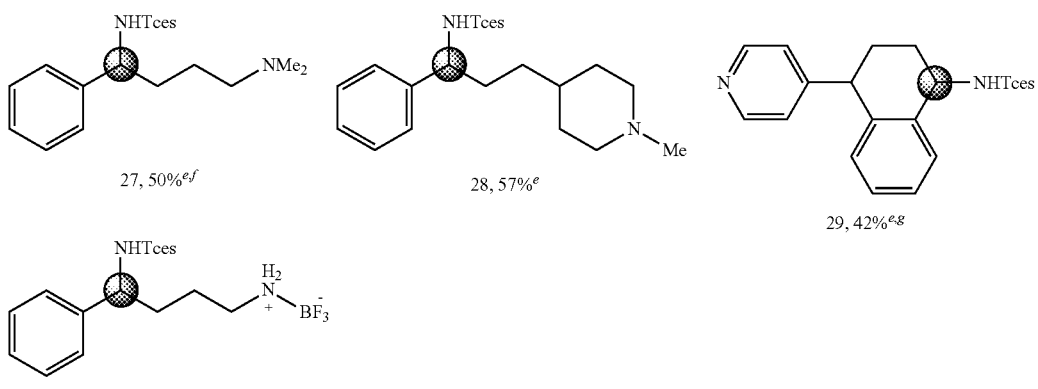

a, One-step, gram-scale synthesis of [Mn^III(ClPc)]Cl from commercial materials. b, General reaction conditions and evaluation of aryl and alkyl electronic effects. Reaction conditions: substrate (0.2 mmol, 1 equiv.), [Mn^III(ClPc)]Cl 3 (10 mol %), AgSbF$_6$ (10 mol %), PhI=NTces (2 equiv.), C$_6$H$_6$ (0.5M), 5 Å molecular sieves (40 mg), 40° C., 8-16 h. Isolated yields are averages of three runs. Diastereomeric ratios are 1:1 unless otherwise noted c, Evaluation of site selectivity: benzylic versus tertiary and sterically and electronically differentiated benzylic C—H bonds. d, Nitrogen-containing heterocyclic substrates with electron-withdrawing groups on nitrogen. e, Brønsted and Lewis acid protection strategy for basic tertiary amine- and pyridine- containing substrates. [a]No tertiary product detected by HPLC (detection limit 0.0002 mg ml$^{-1}$ using authentic product). [b]No tertiary product detected in 1H NMR crude or after purification. [c]No monoamination product detected at C4 by HPLC (detection limit 0.00015 mg ml$^{-1}$ using an authentic product); trace diamination detected using authentic product by HPLC, not seen by $^1$H NMR. An imine product at C1 was isolated in 12% yield. [d]Overall three-step yield (1,2-DCE, 0.5M): acid complexation, amination and decomplexation. [e]3 equiv. PhI = NTces. [f]15 mol % catalyst used. [g]3 Å molecular sieves.

TABLE 1

Development of [Mn^III(ClPc)]-catalysed intermolecular benzylic C—H amination.

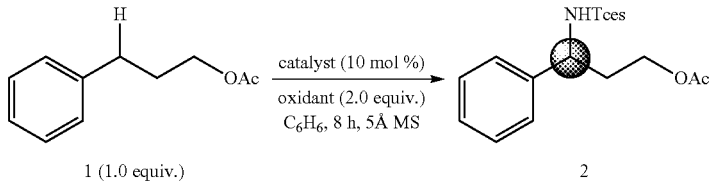

1 (1.0 equiv.)   →   2 catalyst (10 mol %)
oxidant (2.0 equiv.)
$C_6H_6$, 8 h, 5Å MS

| Entry[a] | Sulfamate Ester | Oxidant | Catalyst | Temp | % yield (% rsm) |
|---|---|---|---|---|---|
| 1 | $NH_2Tces$ | $PhI(OPiv)_2$ | $[Fe^{III}(Pc)]SbF_6$ | 23° C. | 0% (100%) |
| 2 | $NH_2Tces$ | $PhI(OPiv)_2$ | $[Mn^{III}(Pc)]SbF_6$ | 23° C. | trace (96%) |
| 3[b] | $NH_2Tces$ | $PhI(OPiv)_2$ | $[Mn^{III}(Pc)]SbF_6$ | 23° C. | trace (95%) |
| 4 | $NH_2Tces$ | $PhI(OPiv)_2$ | $[Mn^{III}(^tBuPc)]SbF_6$ | 23° C. | trace (94%) |
| 5[c] | $NH_2Tces$ | $PhI(OPiv)_2$ | $Co^{II}(TPP)$ | 23° C. | 0% (99%) |
| 6 | | PhI=NTces | $[Fe^{III}(Pc)]SbF_6$ | 23° C. | 9% (85%) |
| 7 | | PhI=NTces | $[Mn^{III}(^tBuPc)]SbF_6$ | 23° C. | 12% (88%) |
| 8 | | PhI=NTces | $[Mn^{III}(Pc)]SbF_6$ | 23° C. | 17% (83%) |
| 9 | | PhI=NTces | $[Mn^{III}(ClPc)]SbF_6$ | 23° C. | 53% (41%) |
| 10 | | PhI=NTces | $[Mn^{III}(ClPc)]SbF_6$ | 40° C. | 68% (32%) |
| 11[d] | | PhI=NTces | $[Mn^{III}(ClPc)]SbF_6$ | 40° C. | 47% (49%) |
| 12[e] | | PhI=NTces | $[Mn^{III}(ClPc)]SbF_6$ | 40° C. | 42% (58%) |
| 13[f] | | PhI=NTces | $[Mn^{III}(ClPc)]SbF_6$ | 40° C. | 60% (24%) |
| 14 | | PhI=NTces | $[Mn^{III}(ClPc)]Cl$ | 40° C. | 50% (43%) |
| 15 | | PhI=NTces | $AgSbF_6$ | 40° C. | 0% (100%) |
| 16 | | PhI=NTces | $Co^{II}(TPP)$ | 40° C. | trace (95%) |
| 17 | $NH_2Tces$ | $PhI(OPiv)_2$ | $[Mn^{III}(ClPc)]SbF_6$ | 40° C. | trace (87%) |

[a]Reaction conditions: 1 (0.2 mmol, 1 equiv.), catalyst (10 mol %), $AgSbF_6$ (10 mol %), oxidant (2 equiv.), $C_6H_6$ (0.5M), 5Å molecular sieves (40 mg), 8 h. Yields are of isolated products. Trace yield (<5%) and recovered starting material (rsm) are reported based on $^1H$ NMR analysis of the crude reaction using 1,3,5-trimethylbenzene as an internal standard.
[b]2.2 equiv. of MgO used as an additive in the reaction.
[c]A separate reaction with 1 (1 equiv.), $TrocN_3$ (2 equiv.), $Co^{II}(TPP)$ (10 mol %), $C_6H_6$ (0.5M), 40° C., 5Å molecular sieves (40 mg), 8 h resulted in 0% yield (88% rsm). TPP, tetraphenylporphyrin.
[d]5 mol % catalyst used.
[e]1 equiv. of PhI=NTces used.
[f]3Å molecular sieves used. 1,2-DCE used as solvent.

Reaction Scope

The substrate scope of this transformation under preparative conditions was evaluated (all examples are with 1 equiv. of substrate) using the novel and readily accessible [Mn^III(ClPc)] 4 catalyst, synthesized in one step as the chloride [Mn^III(ClPc)]Cl 3 from commercial starting materials (95% yield, multigram scale, Scheme 1a) followed by an in situ metathesis with equimolar $AgSbF_6$. In contrast to results with previously reported base-metal catalysts, ethyl benzene furnished good yields and selectivities of aminated product (Scheme 1b; 5, 72%). Significantly, substituting the para position with an electron-withdrawing functionality (Cl, $\sigma_{para}$=0.23, $CF_3$, $\sigma_{para}$=0.54) led to diminished yields as the sigma value of the substituent increased (6, 57%; 7, 30%). A similar trend is observed when varying the aromatic ring electronics on screening substrate 1 where a bias for electron-neutral and electron-rich aromatic systems can be observed (2, 8-10, 55-68% yields). Remote electron-withdrawing aliphatic functionality is well tolerated in this reaction, as seen with ester- and trifluoroacetamide-containing compounds undergoing [Mn^III(ClPc)] 4 catalyzed aminations in good yields (11-13, 65-69% yields).

The [Mn^III(ClPc)] 4-catalyzed benzylic C—H amination was explored in substrates containing more than one potential site for functionalization. In substrates containing both a benzylic and a tertiary site, selective amination at the benzylic position with no tertiary amination was observed by LC-MS (liquid chromatography-mass spectrometry) and/or $^1H$ NMR analysis (Scheme 1c, 14, 53% yield, >100:1 benzylic:tertiary (B:T) amination; 15, 59% yield, >20:1 B:T). These results are in contrast to noble-metal-catalyzed methods where (often inseparable) mixtures of benzylic and tertiary amination products are routinely observed (FIG. 1b).

In substrates containing multiple benzylic sites, it was found there is an amination preference for the least sterically encumbered and most electron-rich site. For example, evaluation of 5-acetoxytetralin bearing two methylene benzylic sites (C1 and C4) revealed preferential amination at the C1 site over the C4 site, possibly due to the 1,3 strain present at C4 (16, 70% yield). Oxygen substitution in cyclic ethers activates adjacent C—H bonds towards amination via hyperconjugation (17, 60% yield). In contrast, oxygen with an electron-withdrawing substituent like acyl deactivates the proximal C—H bond towards amination (18, 60% yield, 1:1 d.r.), probably due to a combination of electronic and steric deactivation. Electronic substitution on the aromatic ring can have substantial effects on site selectivity and reactivity in this reaction. For example, 6-methoxytetralin contains two potential sites for oxidation, differentiated by the electron-donating para-methoxy group on the phenyl ring. The amination product at C1 (19, 58%) was isolated, the more electronically favored site, with only trace diaminated product detected in the crude reaction mixture (determined by HPLC). In contrast, under rhodium catalysis, an inseparable 7:1 mixture of C1:C4 amination products is reported alongside a 15% yield of diamination product. The methoxy substitution on 7-methoxytetralone provides electronic activation to the benzylic methylene C—H bonds to achieve a synthetically useful 51% yield of aminated tetralone 20 (Scheme 1d). It is significant to note that an unsubstituted α-tetralone affords only trace amounts of aminated product.

Evaluation of nitrogen-containing heterocycles commenced using strongly electron-withdrawing protecting groups for secondary amine functionality. Tetrahydroquinoline is a viable substrate for C—H amination when the nitrogen is protected as a trifluoro-acetamide (Scheme 1d, 21, 76% yield). Carbazole, a key heterocycle in many alkaloids, was aminated at the pendent benzylic site in good yield (22, 65%) when the secondary amine was protected with a phenylsulfonyl group. Moderately basic amide-containing heterocycles were also examined under [Mn$^{III}$(ClPc)] 4 catalysis: an N-aryl lactam derived substrate underwent benzylic C—H amination in good yield (23, 63% yield, 1:1 d.r.) and N-aryl oxazolidinone, a structural motif found in pharmaceuticals like linezolid, was aminated to form 24 in 51% yield (1:1 d.r.). The lack of diastereoselectivity observed with these substrates can be attributed to the substrate's stereogenic center being distal to the site of C—H amination.

Despite the high prevalence of basic tertiary amines and basic heterocycles in pharmaceuticals and natural products, previous methods for metal-catalyzed C—H amination proceeding via metallonitrene intermediates have not demonstrated tolerance for these functionalities in remote C—H aminations. Indeed, examining this amination protocol in a substrate containing a tertiary piperidine yielded no benzylic amination product, with 47% recovered starting material (rsm, Scheme 1e, entry 1). It was hypothesized that the basic amine may bind strongly to the metal, inhibiting catalysis, and/or undergo α-amination or direct N-amination to furnish polar products that are not easily isolated. Brønsted acid and Lewis acid complexation strategies that have been demonstrated to circumvent such issues in the context of aliphatic C—H hydroxylations were examined. Both protection methods produced the desired product in good yield (26, 58% and 51% yields, entries 2 and 3). Analogous to previous reports, HBF$_4$ has proven to be more effective for tertiary amines having steric bulk. However, the BF$_3$ complexation strategy enhances substrate solubility and is beneficial with more polar substrates facing isolation challenges (vide infra).

This strategy was evaluated with four basic amine-containing substrates containing pharmaceutically common motifs. The linear 3° amine and N-methylpiperidine-containing substrates were aminated using HBF$_4$/[Mn$^{III}$(ClPc)] 4 to afford 27 (Scheme 1e, 50% yield) and 28 (57% yield), respectively. Pyridine, the most prevalent heteroaromatic in pharmaceuticals, was also tolerated using the HBF$_4$ protonation strategy. A useful yield was observed for 2° benzylic amination in a pyridyl-substituted tetrahydronaphthalene with no 30 benzylic C—H amination observed, probably due to the steric environment and the strong electron-deactivation of the pyridyl ring upon nitrogen protonation (29, 42% yield, 1:1 d.r.). A primary amine-containing substrate can also be conveniently protected as a BF$_3$ salt and aminated using the [Mn$^{III}$(ClPc)] 4 catalyst to afford a product that can be readily isolated via silica gel chromatography (30, 56% yield), stored as a bench-stable solid and easily deprotected using a hydroxide base or fluoride anion.

Late-Stage Benzylic C—H Amination of Bioactive Molecules

Site-selective intermolecular C—H functionalization processes that may be used at a late stage constitute powerful methods because of their capacity to make atomistic changes that may profoundly impact a molecule's biological and physical properties. The [Mn$^{III}$(ClPc)] 4-catalyzed benzylic C—H amination in such pharmaceutical settings where late-stage amination may be beneficial (Scheme 2a) was evaluated. FKGK11, a group VIA calcium-independent phospholipase A$_2$ inhibitor with a pentafluoroethyl carbonyl moiety, underwent benzylic amination to afford 31 in 51% yield. A retinoic acid receptor agonist analogue with a biaryl moiety underwent benzylic amination to afford 32 in 76% yield, which could be readily deprotected using a Zn/Cu couple to afford the primary amine (33, 88% yield). Analogous to previous substrates, electron-deficient nitrogen is well tolerated: a P-glycoprotein inhibitor containing an imide functionality and a spiropiperidine a receptor agonist precursor containing a 2° amine protected as a trifluoroacetamide were efficiently aminated in excellent yields to afford 34 (84% yield) and 35 (85% yield), respectively. Citalopram, a widely used antidepressant containing a linear 3° amine, was evaluated for late-stage C—H amination with HBF$_4$/[Mn$^{III}$(ClPc)] 4. Benzylic amination product 36 was obtained as a single diastereomer in 71% yield. It is significant to note that no intermolecular C—H amination methods have thus far demonstrated the capacity to preparatively aminate such a broad range of medicinally relevant substrates.

Next, bioactive molecules with multiple benzylic C—H bond sites that differ primarily in their steric environments was evaluated. In a dopamine receptor agonist analogue having both 2° and 3° benzylic sites, the HBF$_4$/[Mn$^{III}$(ClPc)] 4-catalyzed amination protocol was effective at selectively functionalizing the more exposed 2° benzylic position to afford 37 (Scheme 2b, 59% yield, 5:1 d.r.). Remarkably, even a glucocorticoid receptor agonist analogue with two sterically differentiated 2° benzylic sites was selectively aminated at the less hindered site flanked by a methylene, rather than the one adjacent to a quaternary center, to furnish 38 as one regioisomer in 56% yield (8:1 d.r.). Antidepressant sertraline 40 was accessed from 39 via a high-yielding three-step synthetic sequence. Site-selective amination of a 2° benzylic C—H bond in the presence of a sterically encumbered but highly activated 3° dibenzylic C—H bond proceeded in 73% yield (1:1 d.r. of an easily separable mixture of cis and trans diastereomers). N-methylation of the cis diastereomer proceeded quantitatively followed by Tces removal with the Zn/Cu couple (95% yield) to afford sertraline 40. These examples serve to highlight the high sensitivity of this C—H amination method to the steric environments of benzylic C—H bonds.

Scheme 2. Late-stage benzylic C—H amination of bioactive molecules.
a.
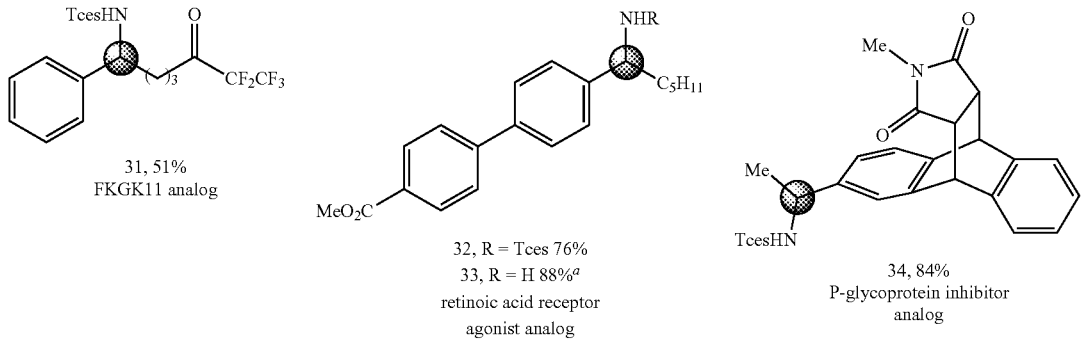
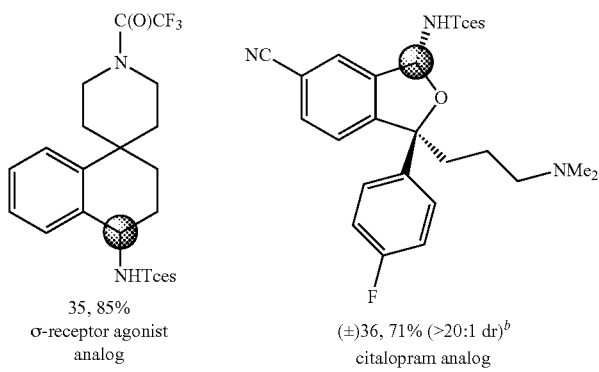
b.
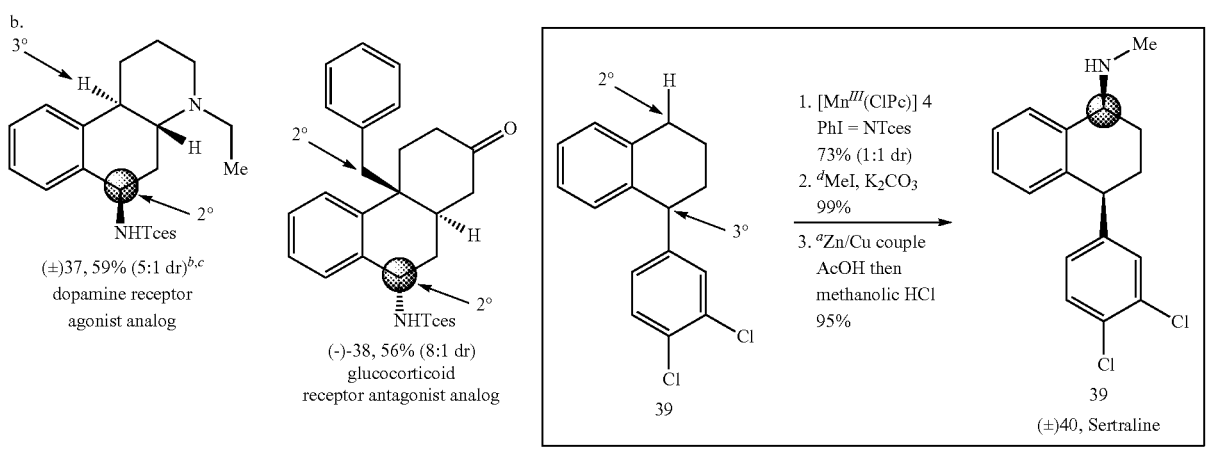
c.
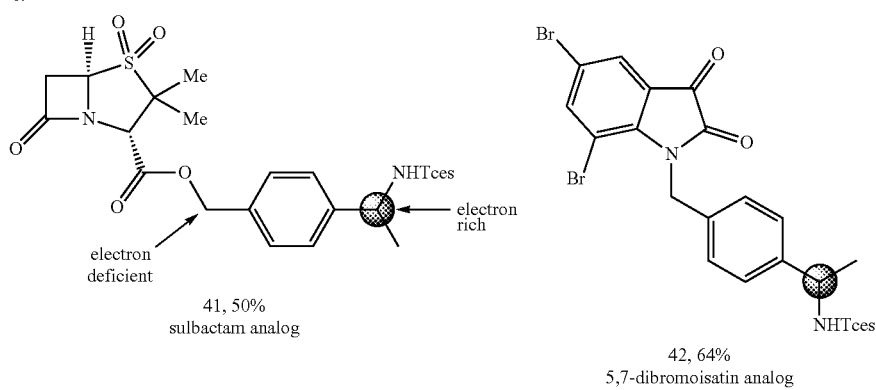

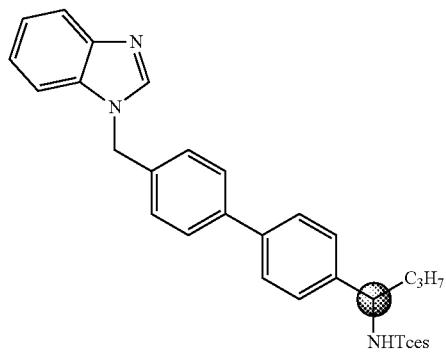

43, 53%[e]
CYP11B1 inhibitor analog a, [Mn[III](ClPc)] 4-catalysed benzylic C—H amination (reaction conditions as in Scheme 1; isolated yields are averages of three runs, diastereomeric ratios are 1:1 unless otherwise noted) selectively installs Tces-protected amines into bioactive molecules that can be converted to primary amines (32→33) b, Bioactive molecules with multiple reactive benzylic C—H bonds are selectively aminated at the most sterically accessible site. c, Bioactive molecules are selectively aminated at the most electron-rich site. [a]Tces deprotection performed using a Zn/Cu couple (10 equiv.), MeOH:AcOH (1:1). After filtration through a celite plug, the concentrated white solid was stirred in methanolic HCl at 40° C. for 12 h to yield the corresponding amine. [b]3 Å molecular sieves (40 mg) used. Substrate protonated with $HBF_4 \cdot OEt_2$ (1.1 equiv.) in $CH_2Cl_2$ prior to amination then deprotonated with 1M NaOH in $CH_2Cl_2$ after amination. [c]3 equiv. of iminoiodinane used. [d]Only the cis-isomer used for alkylation, deprotection. [e]3 Å molecular sieves (40 mg) used. Substrate complexed with $BF_3 \cdot OEt_2$ (1.1 equiv.) in $CH_2Cl_2$ prior to amination and decomplexed with TMEDA in $CH_2Cl_2$.

Bioactive molecules with electronically differentiated 2° benzylic C—H sites, proximal and distal to electron-withdrawing functionality, were evaluated (Scheme 2c). In an alkylated analogue of the antibiotic sulbactam, a 50% yield (1:1 d.r.) of aminated product 41 was isolated at the more electron-rich benzylic site distal from the ester linkage. A 5,7-dibromoisatin analogue, shown to have anti-colon cancer activity, was preferentially aminated at the benzylic site remote from the electron-deficient nitrogen moiety to furnish 42 in 64% yield. The disclosed C—H amination protocol in a CYP11B1 inhibitor analogue with a benzimidazole functionality was evaluated. Use of the $BF_3$ complexation strategy led to an increase in substrate solubility and it was found that amination occurred at the benzylic site remote from the electron-deficient heteroaromatic to furnish 43 in 53% yield. These examples further underscore the sensitivity of [Mn[III](ClPc)] 4-catalyzed benzylic C—H amination to electronics with preparatively meaningful site selectivities being achieved for amination at electron-rich benzylic C—H bonds relative to sites proximal to electron-withdrawing functionality. Such sensitivity to electronics is consistent with an electrophilic metallonitrene intermediate, and inconsistent with a non-electrophilic metalloradical intermediate evoked in Co-mediated intramolecular C—H aminations that demonstrate poor sensitivity to substrate electronics (FIG. 1e, vide infra).

The capacity for the [Mn[III](ClPc)] catalyst to effect late-stage benzylic C—H amination in complex natural product settings (Scheme 3) was explored. The $COCF_3$-leelamine analogue, a diterpene amine with two sterically differentiated 2° and 3° benzylic sites, was selectively aminated at the 2° benzylic site to afford 44 (62% yield, 6:1 dr) as a single regioisomer. The Zn/Cu couple Tces deprotection is chemoselective for the Tces amine in the presence of the $COCF_3$-amine and furnished 45 in 70% yield. The 2,8-dioxabicyclo[3.3.1]nonane skeleton is contained in biflavonoid natural products that exhibit intriguing medicinal properties, including antiviral, anti-inflammatory and anti-tumour properties. Benzylic amination in the presence of this biflavonoid natural product core was achieved to give 46 in 73% yield (1:1 d.r.). Further diversification of the biflavonoid natural product core with a pyridine was performed, and using the $HBF_4$/amination protocol, a 57% yield (1:1 d.r.) of benzylic amination product 47 was ultimately realized. Significantly, the acid-sensitive ketal functionality remains intact under the $HBF_4$ complexation protocol.

Previously, low yields or highly complex mixtures of products were furnished from the C—H azidation of estrone analogues (FIG. 1f). A formylated OAc-estradiol analogue and a structurally analogous pyridyl-containing abiraterone analogue, both with two potential amination sites (20 and 3° benzylic C(sp³)-H bonds) (Scheme 3) was evaluated. In both cases, highly site-selective 20 benzylic amination (3° benzylic amination was not observed) in synthetically useful yields (65% yield (1.6:1 d.r.) for 48; 51% yield (1.6:1 d.r.) for 49) was observed. In the case of the pyridyl-containing steroid, complexation with $BF_3$ was found to be beneficial in generating a $BF_3$-pyridine complex soluble in 1,2-dichloroethane. These examples further underscore the ability of the [Mn[III](ClPc)] 4 catalyst to discriminate between small differences in the steric environments of benzylic sites.

Previous efforts to diversify the 3° amine-containing alkaloid dextromethorphan using a rhodium nitrene provided amination at the 3° amine and the methyl group adjacent to the 3° amine (FIG. 1c). It was postulated that base-metal nitrene-catalyzed amination at a benzylic site remote from the 3° amine would be possible after irreversible protonation of dextromethorphan with $HBF_4$, as the protonated 3° amine renders the nearby C—H bonds electron-deficient. Gratifyingly, the protonated dextromethorphan analogue was aminated in 44% yield (1:1 d.r.) at the benzylic site most remote from the 3° amine (Scheme 3).

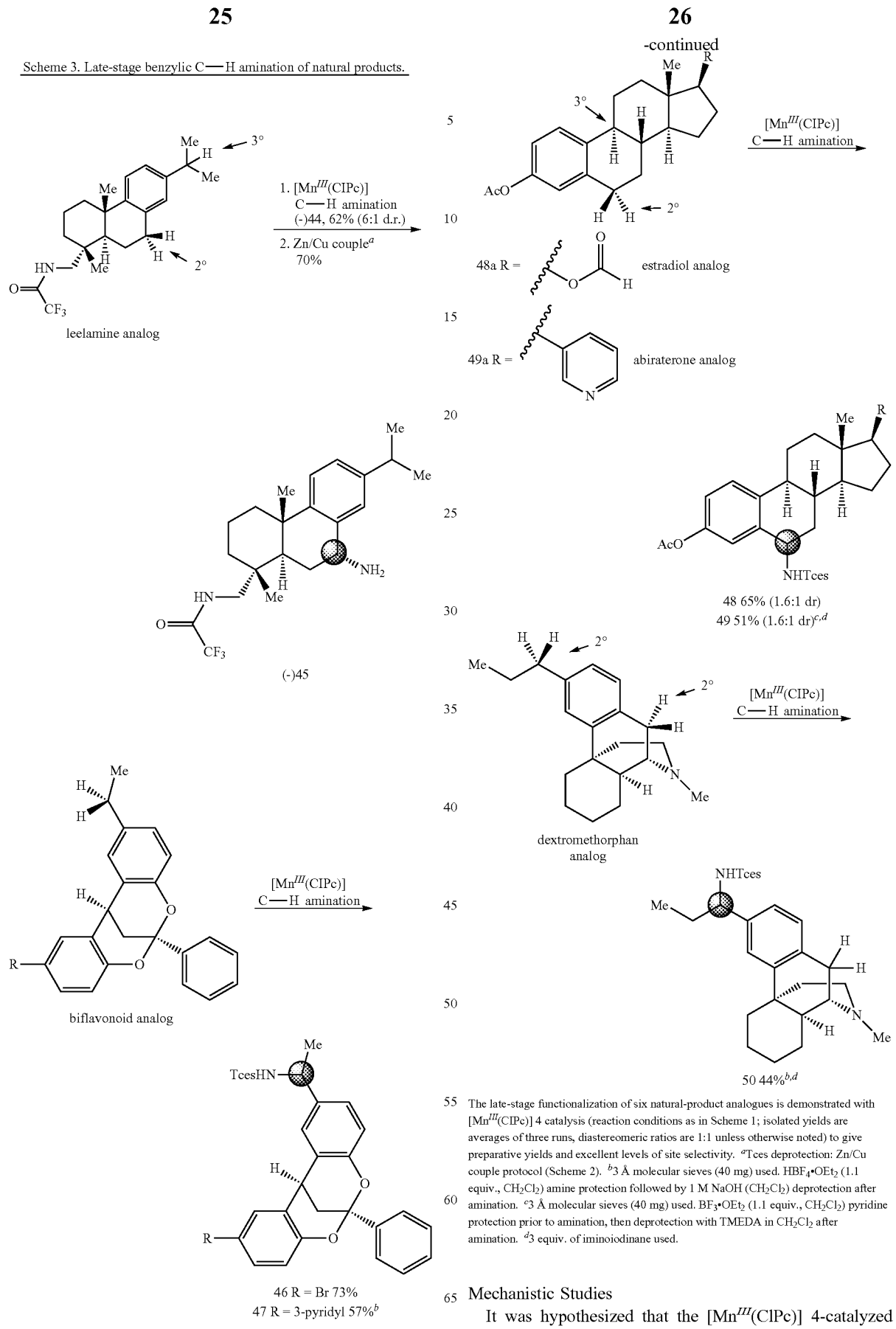

The late-stage functionalization of six natural-product analogues is demonstrated with [Mn$^{III}$(ClPc)] 4 catalysis (reaction conditions as in Scheme 1; isolated yields are averages of three runs, diastereomeric ratios are 1:1 unless otherwise noted) to give preparative yields and excellent levels of site selectivity. [a]Tces deprotection: Zn/Cu couple protocol (Scheme 2). [b]3 Å molecular sieves (40 mg) used. HBF$_4$·OEt$_2$ (1.1 equiv., CH$_2$Cl$_2$) amine protection followed by 1 M NaOH (CH$_2$Cl$_2$) deprotection after amination. [c]3 Å molecular sieves (40 mg) used. BF$_3$·OEt$_2$ (1.1 equiv., CH$_2$Cl$_2$) pyridine protection prior to amination, then deprotection with TMEDA in CH$_2$Cl$_2$ after amination. [d]3 equiv. of iminoiodinane used.

Mechanistic Studies

It was hypothesized that the [Mn$^{III}$(ClPc)] 4-catalyzed intermolecular benzylic C—H amination reaction proceeds via formation of an electrophilic metallonitrene followed by a rate-determining C—H cleavage step to afford a benzylic radical that undergoes rebound from the Mn-imido intermediate to form the benzylic aminated product (Scheme 4a). Whereas in the intramolecular [Mn$^{III}$($^t$BuPc)]-catalyzed C—H amination, a step prior to C—H cleavage, such as iminoiodinane formation, was found to be partially rate-determining, it was envisioned that preforming the iminoiodinane would now render C—H cleavage the rate-determining step.

To assess this hypothesis, the intermolecular kinetic isotope effect (KIE) was measured to evaluate the effect of C—H cleavage on the overall reaction rate and compared to the intramolecular KIE that directly probes the C—H cleavage step (Scheme 4b). Initial rates measured on parallel reactions with substrates 1 and 1-d$_2$ gave a primary KIE of 2.5±0.2. This value closely matched the intramolecular competition KIE of 3.0±0.1 measured on monodeuterated substrate 51, suggesting that C—H cleavage is probably the rate-determining step of this intermolecular benzylic C—H amination. The intramolecular competition KIE is similar to those obtained with other base-metal phthalocyanine catalysts (Mn and Fe) that catalyze intramolecular benzylic C—H aminations (KIE=4.2 and 4.8, respectively), but is appreciably lower than that reported for the cobalt porphyrins that catalyze intramolecular allylic C—H aminations (KIE=6.2). Therefore, although these data support the hypothesis that [Mn$^{III}$(ClPc)]4 proceeds through a stepwise mechanism, C—H bond breakage appears to occur to a much lesser extent in the transition structure than with Co porphyrin catalysis where such a stepwise mechanism has also been evoked.

Next evaluated was the proposed rebound step of the Mn-imido with the substrate benzylic radical intermediate (Scheme 4c). C—H amination at a defined benzylic stereocenter in 52 proceeds with complete erosion in stereochemistry with [Mn$^{III}$(ClPc)] 4, supporting the intermediacy of a stabilized carbon-centered radical. Importantly, intramolecular C—H amination with [Mn$^{III}$(ClPc)] 4 at a defined aliphatic stereocenter in 54 proceeds with complete stereoretention, as has been reported previously with [Mn$^{III}$($^t$BuPc)]. These results support a stepwise mechanism and suggest that the rate of the rebound step is dependent on the stability of the carbon-centered radical intermediate. The nature of the aminating species to distinguish between an electrophilic metallonitrene that has been suggested for rhodium, manganese and iron catalysis versus a non-electrophilic metalloradical intermediate evoked in cobalt catalysis was sought (Scheme 4d). In intramolecular C—H amination studies, rhodium-, manganese- and iron-mediated C—H aminations preferred the more electron-rich C—H site, whereas cobalt-mediated C—H aminations were relatively insensitive to electronics and exhibited site selectivity based primarily on differences in bond dissociation energies (BDEs, FIG. 1e). This was directly probed by examining [Mn$^{III}$(ClPc)] 4-catalyzed C—H amination in substrate 56, which has two benzylic sites that are electronically distinct and have different BDEs (Scheme 4d). [Mn$^{III}$(ClPc)] 4 demonstrates a strong preference for amination at the more electron-rich benzylic site having the higher BDE versus the electron-deficient benzylic site a to a carbonyl having a lower BDE, furnishing 57 in 52% isolated yield with 17:1 site-selectivity (57:58). This outcome contrasts site-selectivity trends reported with non-electrophilic metalloradical-mediated cobalt reactions that preferentially aminate even highly electron-deficient C—H bonds a to carbonyls because of their low BDEs (FIG. 1e). Collectively, the data suggest that Mn phthalocyanine-catalyzed benzylic C—H aminations proceed through a stepwise mechanism via electrophilic metallonitrene intermediates where C—H bond cleavage is tightly regulated at the metal center and occurs preferentially at the most electron-rich and sterically accessible site.

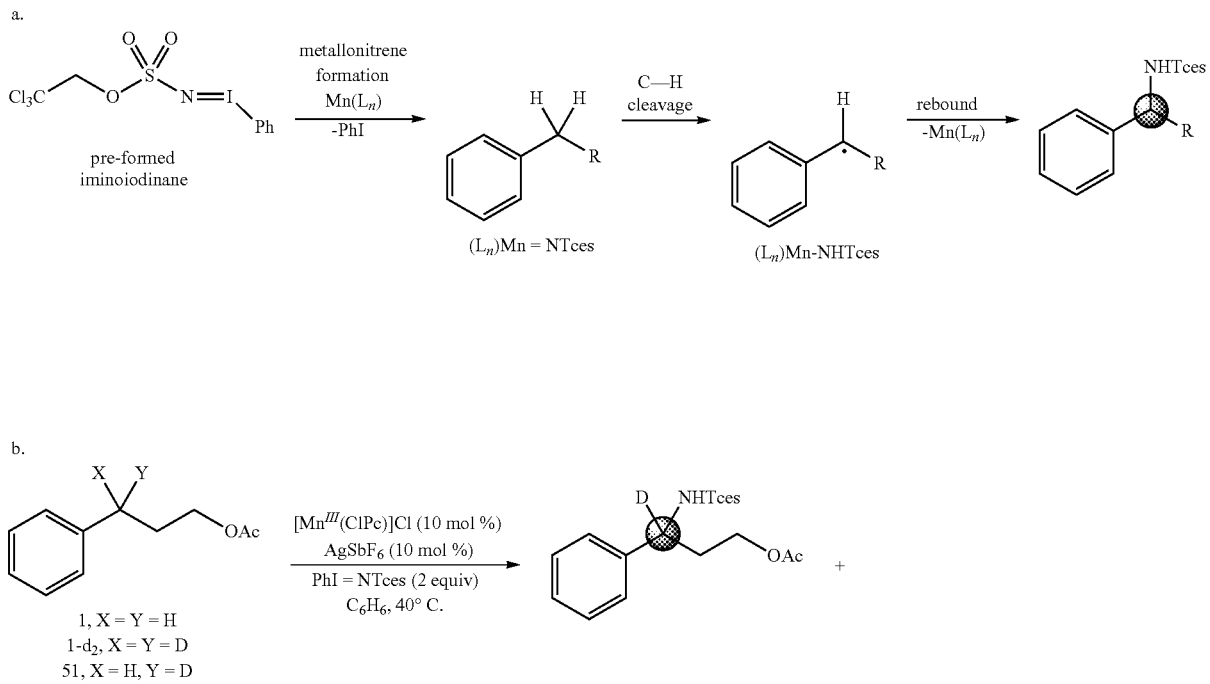

Scheme 4. Mechanism of [Mn$^{III}$(ClPc)]-catalysed benzylic C—H amination.

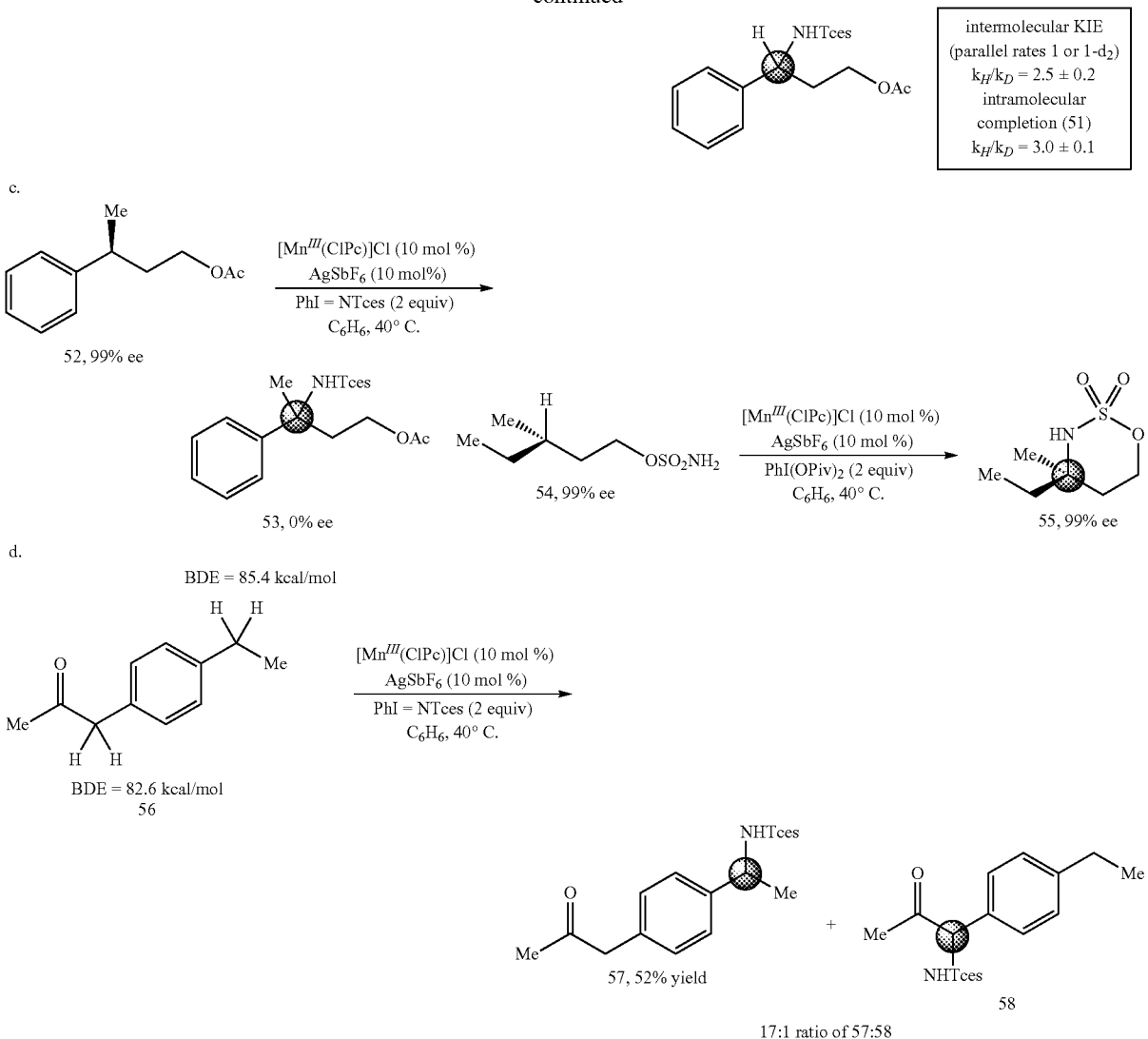

a, Proposed stepwise mechanism for [Mn$^{III}$(ClPc)]- catalysed benzylic C—H amination. b, The C—H cleavage step is the rate-determining step. The intermolecular KIE, evaluating the effect of C—H cleavage on the overall reaction rates, closely matches the intramolecular KIE that directly probes the C—H cleavage step. c, Intermolecular rebound of the Mn-imido with a stablized benzylic radical proceeds with racemization of stereogenic centers. Intramolecular rebound with an aliphatic carbon-centered radical proceeds with complete retention of stereochemistry. d, Site-selectivity of [Mn$^{III}$(ClPc)]-catalyzed C—H amination is probed in a substrate containing two 2° benzylic C(sp$^3$)—H sites that differ electronically and in BDEs. The high site selectivity for the most electron-rich site having a higher BDE suggests that the reaction proceeds via an electrophilic metallonitrene intermediate. The 17:1 ratio of 57:58 was measured by HPLC.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Methods

General Information

The following commercially obtained reagents were used as received: Mn(II)Cl$_2$ (99.995%-Mn, Strem), tetrachlorophthalonitrile (≥96%, TCI), PhI(OAc)$_2$ (Sigma-Aldrich or Oakwood Chemicals), Mn(OAc)$_2$ (Sigma-Aldrich) and powdered 3 Å and 5 Å molecular sieves (Sigma-Aldrich). 2,2,2-trichloroethyl sulfamate was synthesized according to a previously reported procedure (J. Am. Chem. Soc. 2007, 129, 562) and is also commercially available (Sigma-Aldrich). Anhydrous solvents were purified by passage through a bed of activated alumina immediately prior to use (Glass Countour, Laguna Beach, Calif.). Chloroform-d was stored over 3 Å molecular sieves. Thin-layer chromatography (TLC) was conducted with E. Merck silica gel 60 F254 pre-coated plates (0.25 mm) and visualized with UV and Cerium-ammonium-molybdate and potassium permanganate stains. Flash chromatography was performed using American International ZEOprep 60 ECO silica gel (230-400 mesh).

¹H-NMR spectra were recorded on a Varian Unity-400 (400 MHz), Varian VXR 500 (500 MHz), Varian Inova-500 (500 MHz), Varian Unity-500 (500 MHz) or Carver-Bruker 500 (500 MHz) spectrometer and are reported in ppm using solvent as an internal standard (CDCl₃ at 7.26 ppm). Data reported as: s=singlet, d=doublet, t=triplet, q=quartet, p=pentet, sxt=sextet, hept=septet, oct=octet, non=nonet, m=multiplet, br=broad, app=apparent; coupling constant(s) in Hz; integration. Proton-decoupled ¹³C-NMR spectra were recorded on a Varian Unity-400 (400 MHz), Varian Unity-500 (125 MHz) or Carver-Bruker 500 (125 MHz) spectrometer and are reported in ppm using solvent as an internal standard (CDCl₃ at 77.16 ppm). ¹⁹F spectra were recorded on a Varian VXR 500 (470 MHz), Varian Unity-500 (470 MHz) or Carver-Bruker 500 (470 MHz) and are reported in ppm using FCCl₃ (0 ppm) as an external standard. Labeled solvent impurities were calculated out when reporting isolated yields. High-resolution mass spectra were obtained at the University of Illinois Mass Spectrometry Laboratory. Electrospray ionization (ESI) spectra were performed on a Waters Q-Tof µLtima spectrometer, and electron ionization (EI) and field desorption (FD) spectra were performed on a Micromass 70-VSE spectrometer. X-ray crystallographic analysis was carried out by Dr. Toby Woods and Dr. Danielle Gray at the University of Illinois George L. Clark X-Ray Facility.

General Procedures

A general procedure for the manganese-catalyzed benzylic amination is as follows. A Teflon stir bar and 5 Å powdered molecular sieves (40 mg) were added in a 10 ml round-bottom flask, which was sealed with a Suba Seal rubber septum, placed under vacuum, flame-dried for 45 s to activate the molecular sieves, cooled under a purged and completely air-free argon balloon and wrapped in foil to exclude light. Once cooled, solvent (0.40 ml, 0.5 M to substrate) and substrate (0.20 mmol, 1 equiv.) were added and stirred for 10 min. Manganese(III) perchlorophthalocyanine chloride 3 (23.1 mg, 0.020 mmol, 0.1 equiv.) and silver hexafluoroantimonate (6.9 mg, 0.020 mmol, 0.1 equiv.) were weighed in a foil-wrapped 1-dram vial in the glove box and sealed with a Teflon cap. The vial was removed from the glove box and the contents added directly to the round-bottom flask while maintaining an argon atmosphere, then stirred for 10 min at room temperature. In a 1-dram vial open to air, 2,2,2-trichloroethyl (phenyl-λ3-iodanylidene)sulfamate (172.2 mg, 0.40 mmol, 2 equiv.) was weighed and added directly to the round-bottom flask while maintaining an argon atmosphere. The Suba Seal rubber septum was replaced by a polyethylene cap, sealed tightly, and placed in a 40° C. oil bath for 8 h with stirring. Upon reaction completion, the reaction was filtered through a 1 inch silica gel plug using diethyl ether or ethyl acetate as the eluent. The crude material was concentrated and dry-loaded directly onto a silica gel column.

A general procedure for the manganese-catalyzed benzylic amination of basic nitrogen-containing substrates is as follows. In a 1-dram vial equipped with a stir bar, the nitrogen-containing substrate (0.20 mmol, 1 equiv.) and methylene chloride (DCM) (0.8 ml) were added. Tetrafluoroboric acid diethyl ether complex (HBF₄.OEt₂) (30.2 µl, 35.6 mg, 0.22 mmol, 1.1 equiv.) or boron trifluoride diethyl etherate (BF₃.OEt₂) (27.2 µl, 31.2 mg, 0.22 mmol, 1.1 equiv.) was added dropwise while stirring at room temperature. The reaction mixture was stirred for 1 h. Upon reaction completion, the stir bar was removed, and the mixture was concentrated in vacuo and placed on vacuum overnight. A 10 ml round-bottom flask containing 3 Å powdered molecular sieves (40 mg) and a Teflon stir bar was set up and flame-dried according to the general procedure given above. To the 1-dram vial carrying the protonated substrate was added 0.2 ml of anhydrous 1,2-dichloroethane (DCE). The resulting solution or suspension was added into the round-bottom flask containing the 3 Å molecular sieves. This process was repeated twice with 0.1 ml DCE each time to ensure complete transfer.

The amination reaction was then set up according to the general procedure given above. The reaction was then placed in a 40° C. oil bath for 15 h with stirring. Upon completion, the flask was removed from the oil bath. Sodium hydroxide solution (1 M, 3 ml) and CH₂Cl₂ (3 ml) were added and the reaction mixture was vigorously stirred for 15 min (for HBF₄ deprotection) or 4 h (for BF₃ deprotection of amines), and the layers were separated. The aqueous layer was extracted with CH₂Cl₂ (3×5 ml). The organic layers were combined, dried over anhydrous potassium carbonate, filtered, and concentrated via rotary evaporation. The crude material was purified by flash chromatography to afford the aminated product. For deprotection of BF₃ in pyridine and benzimidazole containing substrates, tetramethylethylenediamine (TMEDA) (150 µl, 116 mg, 1.0 mmol, 5 equiv.) was added instead of NaOH, followed by CH₂Cl₂ (1 ml). The resulting mixture was stirred for 4 h and loaded directly onto a silica column.

Example 2. Catalyst and Iminoiodinane Synthesis

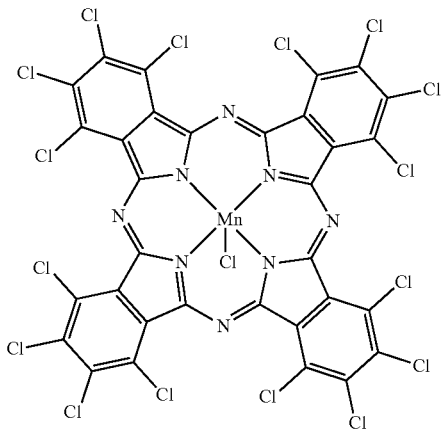

Manganese (III) Perchloro-Phthalocyanine Chloride
[3]

In a 200 mL flame-dried round bottom flask under argon containing a Teflon stir bar and equipped with a water cooled condenser was added consecutively tetrachlorophthalonitrile (3.99 g, 15.00 mmol, 4 equiv), anhydrous Manganese (II) Chloride (472 mg, 3.75 mmol, 1 equiv), freshly distilled 1-Hexanol (45 mL, 0.33M) and 1,8-diazabicyclo[5.4.0]undec-7-ene (2.243 mL, 15.00 mmol, 4 equiv). The flask was placed in a 160° C. silicon oil bath and stirred for 8 h. Upon reaction completion, the flask was removed from the oil bath, allowed to cool to room temperature and cooled for 10 minutes in an ice bath. The contents were poured directly onto a glass fritted Buchner funnel and the solid washed consecutively and three times each with 5% HCl (aq) (3×20 mL), water (3×20 mL), and ethanol (3×40 mL). During the washes, the solid was broken up with a spatula to give a powdered turquoise solid after the last ethanol wash. The solid was collected and placed under vacuum at room temperature for 24 hours to remove any residual solvent to give a turquoise powdery solid (4.12 g, 95% yield) and transferred into the glove box for permanent storage. Manganese (II) perchlorophthalocyanine has been previously reported but there are no reports of the manganese (III) perchlorophthalocyanine chloride catalyst.

UV-Vis (1-Chloronaphthalene, $\lambda_{max}$=nm, $\varepsilon$=$M^{-1}cm^{-1}$): 770 ($\varepsilon$=84968), 691 ($\varepsilon$=20629), 525 ($\varepsilon$=10675), 400 ($\varepsilon$=23658), 356 ($\varepsilon$=25245).

IR (ATR, $cm^{-1}$): 3124, 2927, 2856, 1644, 1564, 1467, 1427, 1385, 1310, 1272, 1203, 1152, 1130, 1095, 1039, 954, 931, 763, 746, 734, 598, 572, 497.

MS (MALDI) (DHB Matrix): m/z calculated for $C_{32}Cl_{17}MnN_8$ [M−Cl]$^+$: 1110.464, found 1110.507.

UV-Vis Studies:

In a 25 mL volumetric flask, 2.0 mg (0.0017 mmol) of manganese (III) perchlorophthalocyanine chloride was taken up in 1-chloronaphthalene to make a 25 mL solution (69 μM). 100 μL of this solution was diluted to 1 mL (6.9 μM) in a 1 mL volumetric flask. A UV-Vis was taken from 1100-350 nm in a quartz cuvette (path length=1 cm).

Synthesis of the Perchlorophthalocyanine Ligand then Insertion of the Metal

The ligand was synthesized using a known literature procedure and characterized (Synlett, 2003, 13, 2083). The manganese metal was inserted into the ligand and tested in the intermolecular benzylic C—H amination protocol to validate the identity of the catalyst made from the phthalonitrile.

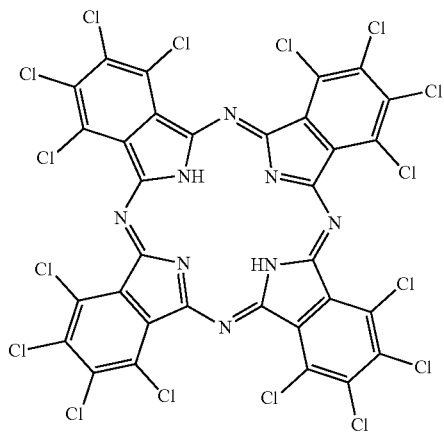 [SMILES: Clc1c(Cl)c(Cl)c2c(c1Cl)-c1nc-2nc2[nH]c(nc3nc(nc4[nH]c(n1)c1c(Cl)c(Cl)c(Cl)c(Cl)c41)-c1c(Cl)c(Cl)c(Cl)c(Cl)c1-3)c1c(Cl)c(Cl)c(Cl)c(Cl)c21]

1,2,3,4,8,9,10,11,15,16,17,18,22,23,24,25-hexadecachlorophthalocyanine [S1]

Accordingly, in a 50 mL sealed tube vessel, tetrachlorophthalic anhydride (1.56 g, 5.44 mmol, 1 equiv), hexamethyldisilazane (5.74 mL, 27.2 mmol, 5 equiv), p-toluenesulfonic acid-$H_2O$ (103.5 mg, 0.544 mmol, 0.1 equiv), and N,N-dimethylformamide (0.42 mL, 5.44 mmol, 1 equiv) were added and the vessel sealed, heated to 150° C. and stirred overnight behind a blast shield. The reaction was brought to room temperature and then opened. The green solid was broken up and washed with MeOH (50 mL). The solid was then dissolved in concentrated $H_2SO_4$ (40 mL), stirred for 5 minutes then poured into a 250 mL Erlenmeyer flask containing ice water (about 120 mL ice water volume). The precipitate that crashes out of solution was collected and further washed with $H_2O$ then MeOH. The green solid was transferred to a Soxhlet thimble and extracted using MeOH (150 mL) for 2 days. The solid remaining in the thimble (250 mg, 0.23 mmol, 17% yield) was collected and used in the next step.

$^{13}C$ NMR (126 MHz, DMF): δ 165.65, 139.56, 130.57, 129.50.

IR (ATR, $cm^{-1}$): 3460, 3385, 3313, 2920, 1741, 1706, 1649, 1601, 1564, 1430, 1380, 1367, 1356, 1339, 1315, 1275, 1189, 1131, 1085, 1043, 921, 862, 747, 655.

MS (MALDI) (No Matrix): m/z calculated for $C_{32}H_3Cl_{16}N_8$ [M+H]$^+$: 1058.550, found 1058.304.

Manganese (III) Perchloro-Phthalocyanine Chloride [3]

Synthesized from S1 using a previously reported method (Nat. Chem., 2015, 7, 987). In a new, flame-dried 25 mL round bottom flask containing a new Teflon stir bar (free of trace metal impurities) under a $N_2$ atmosphere were added 1,2,3,4,8,9,10,11,15,16,17,18,22,23,24,25-hexadecachlorophthalocyanine S1 (110 mg, 0.103 mmol, 1 equiv), Mn(OAc)$_2$ (17.8 mg, 0.103 mmol, 1 equiv) and N,N-dimethylformamide (6 mL). The reaction was stirred for 12 h at 60° C. Upon reaction completion, $H_2O$ (10 mL) was added to crash out the catalyst and the catalyst was filtered then washed subsequently with 1M HCl, brine, $H_2O$ then MeOH. The dark green solid was transferred to a Soxhlet thimble and extracted using Soxhlet extraction for 2 days using MeOH (40 mL). The remaining solid in the thimble was collected (50 mg, 0.43 mmol, 40% yield) and tested for intermolecular benzylic C—H amination reactivity using 3-phenylpropyl acetate using the exact conditions in Table 1 entry 9 to yield 3-phenyl-3-(((2,2,2-trichloroethoxy)sulfonyl)amino)propyl acetate 2 (52 mg, 0.129 mmol, 64% yield).

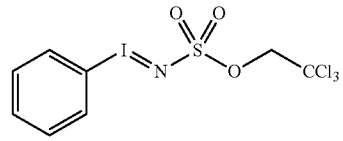

2,2,2-trichloroethyl (phenyl-$\lambda^3$-iodanylidene)sulfamate [S2]

In a flame-dried 100 mL round bottom flask under nitrogen was added 2,2,2-trichloroethyl sulfamate (2.0 g, 8.75 mmol, 1 equiv), (diacetoxyiodo)benzene (2.82 g, 8.75 mmol, 1 equiv) and anhydrous methanol (35 mL, 0.25M). The contents were stirred to dissolve most of the (diacetoxyiodo)benzene and then cooled to 0° C. in an ice-water bath. Once cooled, potassium hydroxide (1.23 g, 21.88 mmol, 2.5 equiv) was added as pellets. The reaction was stirred for 30 minutes at 0° C. and then 7.5 hours at room temperature. Upon reaction completion, the contents were transferred to a separatory funnel containing 100 mL of water. Dichloromethane (100 mL) was added and the contents vigorously shaken to remove all excess potassium hydroxide (very important). The layers were separated and the aqueous layer was further extracted with dichloromethane (2×100 mL). The combined organic extracts were washed with water (1×100 mL), shaking vigorously to remove any trace potassium hydroxide, and transferred directly to a 500 mL round bottom flask and the solvent removed by rotary evaporation at room temperature (do not exceed 30° C. as the iminoiodinane will not perform optimally) to give a slightly yellow solid. The contents were transferred to a 100 mL round bottom flask using 20 mL of methanol and the solvent was removed by rotary evaporation leaving a slightly yellow solid. The contents were azeotroped once with 20 mL of benzene and placed under vacuum for an additional 20 minutes to give a slightly yellow solid. The solid was triturated with diethyl ether (5×10 mL) while breaking up any solid chunks into a powdery solid. After vacuum drying for one hour an off-white powdery solid was obtained (1.78 g, 47% yield) and used as is. The contents were capped with a polyethylene cap and stored in the freezer. The iminoiodinane is stable for at least 3 months in the freezer. This procedure was adapted from a previously reported procedure (J. Org. Chem. 1999, 64, 5304) but deviates significantly in several steps and the above described procedure should be followed for best results.

$^1$H NMR (499 MHz, Methanol-$d_4$): δ 8.22-8.11 (d, J=7.4 Hz, 0.6H), 8.10-7.96 (m, 1.4H), 7.68 (t, J=7.5 Hz, 0.3H), 7.64-7.46 (m, 2.7H), 4.68 (s, 1.4H), 4.29 (s, 0.6H).

$^{13}$C NMR (126 MHz, Methanol-$d_4$): δ 136.3, 133.4, 133.3, 132.3, 132.2, 132.0, 122.6, 95.3, 79.0, 78.9.

HRMS (ESI-TOF MS ES-): m/z calculated for $C_8H_7Cl_4NIO_3S$ [M+Cl]$^-$: 463.7945, found 463.7939.

Example 3. General Amination Procedures and Optimization Data for Table 1

General Procedure a for Reaction Optimization Studies (In Situ Formation of Iminoiodinane, Entries 1-4, 15):

In a 10 mL round bottom flask was added 5 Å powdered molecular sieves (40 mg) and a Teflon stir bar. The flask was sealed with a Suba Seal rubber septum, placed under vacuum, flame-dried for 45 seconds to activate the molecular sieves, cooled under argon and wrapped in foil to exclude light. Once cooled, solvent (0.40 mL, 0.5 M to substrate), commercial 3-phenylpropyl acetate 1 (35.6 mg, 0.20 mmol, 1 equiv), and 2,2,2-trichloroethyl sulfamate (54.8 mg, 0.24 mmol, 1.2 equiv) were added and stirred for 10 minutes. Catalyst (0.020 mmol, 0.1 equiv) and silver hexafluoroantimonate (6.9 mg, 0.020 mmol, 0.1 equiv) were weighed in a foil wrapped 1 dram vial in the glove box and sealed with a Teflon cap. The vial was removed from the glove box and the contents added directly to the round bottom flask while maintaining an argon atmosphere. In a 1 dram vial open to air, di-(pivaloyloxy)iodobenzene (162.4 mg, 0.40 mmol, 2 equiv) was weighed and added directly to the round bottom flask while maintaining an argon atmosphere. The Suba Seal rubber septum was replaced by a polyethylene cap, sealed tightly and stirred for 8 hours at room temperature. Upon reaction completion, the reaction was filtered through a 1-inch silica gel plug using diethyl ether the eluent. The solvent was evaporated and a crude $^1$H NMR was obtained using mesitylene (9.3 μL, 0.067 mmol, 0.33 equiv) as an internal standard to obtain the $^1$H NMR yield.

General Procedure B for Reaction Optimization Studies (Pre-Formed Iminoiodinane, Entries 5-14).

In a 10 mL round bottom flask was added 5 Å powdered molecular sieves (40 mg) and a Teflon stir bar. The flask was sealed with a Suba Seal rubber septum, placed under vacuum, flame-dried for 45 seconds to activate the molecular sieves, cooled under a purged and completely air-free argon balloon and wrapped in foil to exclude light. Once cooled, solvent (0.40 mL, 0.5 M to substrate) and 3-phenylpropyl acetate 1 (35.6 mg, 0.20 mmol, 1 equiv) were added and stirred for 10 minutes. Catalyst (0.020 mmol, 0.1 equiv) and silver hexafluoroantimonate (6.9 mg, 0.020 mmol, 0.1 equiv) were weighed in a foil wrapped 1 dram vial in the glove box and sealed with a Teflon cap. The vial was removed from the glove box and the contents added directly to the round bottom flask and stirred for 10 minutes while maintaining an argon atmosphere. In a 1 dram vial open to air, 2,2,2-trichloroethyl (phenyl-λ$^3$-iodanylidene)sulfamate (172.2 mg, 0.40 mmol, 2 equiv) was weighed and added directly to the round bottom flask while maintaining an argon atmosphere. The Suba Seal rubber septum was replaced by a polyethylene cap, sealed tightly and stirred for 8 hours at the given temperature. Upon reaction completion, the reaction was filtered through a 1 inch silica gel plug using diethyl ether as the eluent. The solvent was evaporated and a crude $^1$H NMR in $CDCl_3$ was obtained using mesitylene (9.3 μL, 0.067 mmol, 0.33 equiv) as an internal standard to obtain the $^1$H NMR yield. The crude material was then concentrated and dry-loaded directly onto a silica gel column. Flash chromatography using gradient elution (500 mL of 100% dichloromethane (removes excess $NH_2Tces$) then 300 mL of 2% diethyl ether in 98% dichloromethane followed by 300 mL of 5% diethyl ether in 95% dicholoromethane) gave the pure product as a white solid with slight discoloration.

Entry 1.

According to the general procedure A for optimization studies, 5 Å powdered molecular sieves (40 mg), 3-phenylpropyl acetate (35.6 mg, 0.20 mmol, 1 equiv), $C_6H_6$ (0.40 mL, 0.5M), [FePc]Cl (12.1 mg, 0.020 mmol, 0.1 equiv), $AgSbF_6$ (6.9 mg, 0.020 mmol, 0.1 equiv), $NH_2Tces$ (54.8 mg, 0.24 mmol, 1.2 equiv) and PhI(OPiv)$_2$ (162.4 mg, 0.40 mmol, 2 equiv) were combined in a 10 mL round-bottom flask and stirred for 8 h at room temperature.

Run 1 (0% yield by $^1$H NMR yield, 100% rsm by $^1$H NMR).

Run 2 (0% yield by $^1$H NMR yield, 100% rsm by $^1$H NMR).

Run 3 (0% yield by $^1$H NMR yield, 100% rsm by $^1$H NMR).

Entry 2.

According to the general procedure A for optimization studies, 5 Å powdered molecular sieves (40 mg), 3-phenylpropyl acetate (35.6 mg, 0.20 mmol, 1 equiv), $C_6H_6$ (0.40 mL, 0.5M), [MnPc]Cl (12.1 mg, 0.020 mmol, 0.1 equiv), $AgSbF_6$ (6.9 mg, 0.020 mmol, 0.1 equiv), $NH_2Tces$ (54.8 mg, 0.24 mmol, 1.2 equiv) and PhI(OPiv)$_2$ (162.4 mg, 0.40 mmol, 2 equiv) were combined in a 10 mL round-bottom flask and stirred for 8 h at room temperature.

Run 1 (trace yield by $^1$H NMR, 95% rsm by $^1$H NMR).

Run 2 (trace yield by $^1$H NMR, 97% rsm by $^1$H NMR).

Run 3 (trace yield by $^1$H NMR, 95% rsm by $^1$H NMR).

Entry 3.

According to the general procedure A for optimization studies, 5 Å powdered molecular sieves (40 mg) magnesium oxide (17.7 mg, 0.44 mmol, 2.2 equiv), 3-phenylpropyl acetate (35.6 mg, 0.20 mmol, 1 equiv), $C_6H_6$ (0.40 mL, 0.5M), [MnPc]Cl (12.1 mg, 0.020 mmol, 0.1 equiv), $AgSbF_6$ (6.9 mg, 0.020 mmol, 0.1 equiv), $NH_2Tces$ (54.8 mg, 0.24 mmol, 1.2 equiv) and PhI(OPiv)$_2$ (162.4 mg, 0.40 mmol, 2 equiv) were combined in a 10 mL round-bottom flask and stirred for 8 h at room temperature.

Run 1 (trace yield by ¹H NMR, 95% rsm by ¹H NMR).
Run 2 (trace yield by ¹H NMR, 96% rsm by ¹H NMR).
Run 3 (trace yield by ¹H NMR, 95% rsm by ¹H NMR).
Entry 4.

According to the general procedure A for optimization studies, 5 Å powdered molecular sieves (40 mg), 3-phenylpropyl acetate (35.6 mg, 0.20 mmol, 1 equiv), $C_6H_6$ (0.40 mL, 0.5M), [Mn($^t$BuPc)]Cl (16.5 mg, 0.020 mmol, 0.1 equiv), $AgSbF_6$ (6.9 mg, 0.020 mmol, 0.1 equiv), $NH_2Tces$ (54.8 mg, 0.24 mmol, 1.2 equiv) and $PhI(OPiv)_2$ (162.4 mg, 0.40 mmol, 2 equiv) were combined in a 10 mL round-bottom flask and stirred for 8 h at room temperature.
Run 1 (trace yield by ¹H NMR, 95% rsm by ¹H NMR).
Run 2 (trace yield by ¹H NMR, 98% rsm by ¹H NMR).
Run 3 (trace yield by ¹H NMR, 90% rsm by ¹H NMR).
Entry 5.

According to the general procedure A for optimization studies, 5 Å powdered molecular sieves (40 mg), 3-phenylpropyl acetate (35.6 mg, 0.20 mmol, 1 equiv), $C_6H_6$ (0.40 mL, 0.5M), Co(TPP) (13.4 mg, 0.020 mmol, 0.1 equiv), $NH_2Tces$ (54.8 mg, 0.24 mmol, 1.2 equiv) and $PhI(OPiv)_2$ (162.4 mg, 0.40 mmol, 2 equiv) were combined in a 10 mL round-bottom flask and stirred for 8 h at room temperature.
Run 1 (0% yield by ¹H NMR, 100% rsm by ¹H NMR).
Run 2 (0% yield by ¹H NMR, 97% rsm by ¹H NMR).
Run 3 (0% yield by ¹H NMR, 99% rsm by ¹H NMR).
Entry 5.

According to the general procedure A for optimization studies, 5 Å powdered molecular sieves (40 mg), 3-phenylpropyl acetate (35.6 mg, 0.20 mmol, 1 equiv), $C6H_6$ (0.40 mL, 0.5M), Co(TPP) (13.4 mg, 0.020 mmol, 0.1 equiv) and 2,2,2-trichloroethoxycarbonyl azide (87.4 mg, 0.40 mmol, 2 equiv) were combined in a 10 mL round-bottom flask and stirred for 8 h at room temperature.
Run 1 (0% yield by ¹H NMR, 86% rsm by ¹H NMR).
Run 2 (0% yield by ¹H NMR, 90% rsm by ¹H NMR).
Run 3 (0% yield by ¹H NMR, 88% rsm by ¹H NMR).
Entry 6.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), [FePc]Cl (12.1 mg, 0.020 mmol, 0.1 equiv), $AgSbF_6$ (6.9 mg, 0.020 mmol, 0.1 equiv) and PhI=NTces (172.2 mg, 0.40 mmol, 2 equiv) were combined in a 10 mL round-bottom flask and stirred for 8 h at room temperature.
Run 1 (9% ¹H NMR yield, 72% rsm by ¹H NMR).
Run 2 (8% ¹H NMR yield, 92% rsm by ¹H NMR).
Run 3 (7 mg, 0.017 mmol, 9% isolated yield, 90% rsm by ¹H NMR).
Entry 7.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), [Mn(BuPc)]Cl (16.5 mg, 0.020 mmol, 0.1 equiv), $AgSbF_6$ (6.9 mg, 0.020 mmol, 0.1 equiv) and PhI=NTces (172.2 mg, 0.40 mmol, 2 equiv) were combined in a 10 mL round-bottom flask and stirred for 8 h at room temperature.
Run 1 (10% ¹H NMR yield, 86% rsm by ¹H NMR).
Run 2 (9% ¹H NMR yield, 91% rsm by ¹H NMR).
Run 3 (10 mg, 0.025 mmol, 12% isolated yield, 88% rsm by ¹H NMR).
Entry 8.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), [MnPc]Cl (12.1 mg, 0.020 mmol, 0.1 equiv), $AgSbF_6$ (6.9 mg, 0.020 mmol, 0.1 equiv) and PhI=NTces (172.2 mg, 0.40 mmol, 2 equiv) were combined in a 10 mL round-bottom flask and stirred for 8 h at room temperature.
Run 1 (14% ¹H NMR yield, 86% rsm by ¹H NMR).
Run 2 (16% ¹H NMR yield, 80% rsm by ¹H NMR).
Run 3 (14 mg, 0.035 mmol, 17% isolated yield, 83% rsm by ¹H NMR).
Entry 9.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), manganese (III) perchlorophthalocyanine chloride (23.1 mg, 0.020 mmol, 0.1 equiv), $AgSbF_6$ (6.9 mg, 0.020 mmol, 0.1 equiv) and PhI=NTces (172.2 mg, 0.40 mmol, 2 equiv) were combined in a 10 mL round-bottom flask and stirred for 8 h at room temperature.
Run 1 (60% ¹H NMR yield, 40% rsm by ¹H NMR).
Run 2 (60% ¹H NMR yield, 37% rsm by ¹H NMR).
Run 3 (43 mg, 0.106 mmol, 53% isolated yield, 45% rsm by ¹H NMR).
Entry 10.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), manganese (III) perchlorophthalocyanine chloride (23.1 mg, 0.020 mmol, 0.1 equiv), $AgSbF_6$ (6.9 mg, 0.020 mmol, 0.1 equiv) and PhI=NTces (172.2 mg, 0.40 mmol, 2 equiv) were combined in a 10 mL round-bottom flask and stirred for 8 h at 40° C.
Run 1 (53 mg, 0.131 mmol, 66% isolated yield, 33% rsm by ¹H NMR).
Run 2 (54 mg, 0.133 mmol, 67% isolated yield, 33% rsm by ¹H NMR).
Run 3 (57 mg, 0.141 mmol, 71% isolated yield, 29% rsm by ¹H NMR).
Entry 11.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), manganese (III) perchlorophthalocyanine chloride (11.5 mg, 0.010 mmol, 0.05 equiv), $AgSbF_6$ (3.4 mg, 0.010 mmol, 0.05 equiv) and PhI=NTces (172.2 mg, 0.40 mmol, 2 equiv) were combined in a 10 mL round-bottom flask and stirred for 8 h at 40° C.
Run 1 (55% ¹H NMR yield, 45% rsm by ¹H NMR).
Run 2 (50% ¹H NMR yield, 50% rsm by ¹H NMR).
Run 3 (38 mg, 0.094 mmol, 47% isolated yield, 53% rsm by ¹H NMR).
Entry 12.

According to the general procedure B for optimization studies, 5 Å powdered molecular sieves (40 mg), 3-phenylpropyl acetate (35.6 mg, 0.20 mmol, 1 equiv), $C_6H_6$ (0.40 mL, 0.5M), manganese (III) perchlorophthalocyanine chloride (23.1 mg, 0.020 mmol, 0.1 equiv), $AgSbF_6$ (6.9 mg, 0.020 mmol, 0.1 equiv) and PhI=NTces (86.1 mg, 0.20 mmol, 1 equiv) were combined in a 10 mL round-bottom flask and stirred for 8 h at 40° C.
Run 1 (42% ¹H NMR yield, 58% rsm by ¹H NMR).
Run 2 (40% ¹H NMR yield, 60% rsm by ¹H NMR).
Run 3 (34 mg, 0.084 mmol, 42% isolated yield, 56% rsm by ¹H NMR).
Entry 13.

According to the general procedure B for optimization studies, 3 Å powdered molecular sieves (40 mg), 3-phenylpropyl acetate (35.6 mg, 0.20 mmol, 1 equiv), 1,2-dichloroethane (0.40 mL, 0.5M), manganese (III) perchlorophthalocyanine chloride (23.1 mg, 0.020 mmol, 0.1 equiv), AgSbF$_6$ (6.9 mg, 0.020 mmol, 0.1 equiv) and PhI=NTces (172.2 mg, 0.40 mmol, 2 equiv) were combined in a 10 mL round-bottom flask and stirred for 8 h at 40° C.

Run 1 (61% $^1$H NMR yield, 26% rsm by $^1$H NMR).

Run 2 (59% $^1$H NMR yield, 24% rsm by $^1$H NMR).

Run 3 (49 mg, 0.121 mmol, 60% isolated yield, 22% rsm by $^1$H NMR).

Entry 14.

According to the general procedure B for optimization studies, 5 Å powdered molecular sieves (40 mg), 3-phenyl-propyl acetate (35.6 mg, 0.20 mmol, 1 equiv), C$_6$H$_6$ (0.40 mL, 0.5M), manganese (III) perchlorophthalocyanine chloride (23.1 mg, 0.020 mmol, 0.1 equiv) PhI=NTces (172.2 mg, 0.40 mmol, 2 equiv) were combined in a 10 mL round-bottom flask and stirred for 8 h at 40° C.

Run 1 (52% $^1$H NMR yield, 48% rsm by $^1$H NMR).

Run 2 (55% $^1$H NMR yield, 36% rsm by $^1$H NMR).

Run 3 (40 mg, 0.099 mmol, 50% isolated yield, 46% rsm by $^1$H NMR).

Entry 15.

According to the general procedure B for optimization studies, 5 Å powdered molecular sieves (40 mg), 3-phenyl-propyl acetate (35.6 mg, 0.20 mmol, 1 equiv), C$_6$H$_6$ (0.40 mL, 0.5M), AgSbF$_6$ (6.9 mg, 0.020 mmol, 0.1 equiv) and PhI=NTces (172.2 mg, 0.40 mmol, 2 equiv) were combined in a 10 mL round-bottom flask and stirred for 8 h at 40° C.

Run 1 (0% yield by $^1$H NMR yield, 100% rsm by $^1$H NMR).

Run 2 (0% a yield by $^1$H NMR yield, 100% rsm by $^1$H NMR).

Run 3 (0% a yield by $^1$H NMR yield, 100% rsm by $^1$H NMR).

Entry 16.

According to the general procedure B for optimization studies, 5 Å powdered molecular sieves (40 mg), 3-phenyl-propyl acetate (35.6 mg, 0.20 mmol, 1 equiv), C$_6$H$_6$ (0.40 mL, 0.5M), Co(TPP) (13.4 mg, 0.020 mmol, 0.1 equiv) and PhI=NTces (172.2 mg, 0.40 mmol, 2 equiv) were combined in a 10 mL round-bottom flask and stirred for 8 h at 40° C.

Run 1 (2% yield by $^1$H NMR yield, 98% rsm by $^1$H NMR).

Run 2 (0% yield by $^1$H NMR yield, 96% rsm by $^1$H NMR).

Run 3 (0% yield by $^1$H NMR yield, 90% rsm by $^1$H NMR).

Entry 17.

According to the general procedure A for optimization studies, 5 Å powdered molecular sieves (40 mg), 3-phenyl-propyl acetate (35.6 mg, 0.20 mmol, 1 equiv), C$_6$H$_6$ (0.40 mL, 0.5M), manganese (III) perchlorophthalocyanine chloride (23.1 mg, 0.020 mmol, 0.1 equiv), AgSbF$_6$ (6.9 mg, 0.020 mmol, 0.1 equiv), NH$_2$Tces (54.8 mg, 0.24 mmol, 1.2 equiv) and PhI(OPiv)$_2$ (162.4 mg, 0.40 mmol, 2 equiv) were combined in a 10 mL round-bottom flask and stirred for 8 h at 40° C.

Run 1 (trace yield by $^1$H NMR yield, 90% rsm by $^1$H NMR).

Run 2 (trace yield by $^1$H NMR yield, 86% rsm by $^1$H NMR).

Run 3 (trace yield by $^1$H NMR yield, 84% rsm by $^1$H NMR).

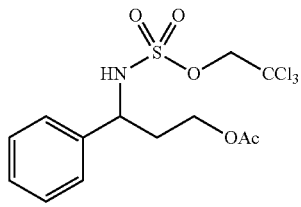

3-phenyl-3-(((2,2,2-trichloroethoxy)sulfonyl)amino) propyl acetate [2]

According to the general amination procedure A, 5 Å powdered molecular sieves (40 mg), commercial 3-phenyl-propyl acetate 1 (35.6 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as a slightly yellow solid.

Run 1 (53 mg, 0.131 mmol, 66% yield).

Run 2 (54 mg, 0.133 mmol, 67% yield).

Run 3 (57 mg, 0.141 mmol, 71% yield).

Average overall yield: 68% yield±2.6.

$^1$H NMR (500 MHz, Chloroform-d): δ 7.40-7.35 (m, 2H), 7.34-7.29 (m, 3H), 5.73 (d, J=7.7 Hz, 1H), 4.68 (q, J=7.4 Hz, 1H), 4.32 (d, J=10.8 Hz, 1H), 4.27 (d, J=10.8 Hz, 1H), 4.18-4.13 (m, 1H), 4.05-4.00 (m, 1H), 2.32-2.25 (m, 1H), 2.18-2.11 (m, 1H), 2.04 (s, 3H).

$^{13}$C NMR (126 MHz, CDCl$_3$): δ 171.2, 139.7, 129.2, 128.6, 126.7, 93.3, 78.1, 61.1, 56.9, 35.6, 21.0.

HRMS (ESI-TOF MS ES+): m/z calculated for C$_{13}$H$_{16}$NO$_5$SCl$_3$Na [M+Na]$^+$: 425.9712, found 425.9706.

Example 4. Experimental Procedures and Compound Characterization for Scheme 1

General Amination Procedure B for Benzylic Amination:

In a 10 mL round bottom flask, 5 Å powdered molecular sieves (40 mg) and a Teflon stir bar were added. The flask was sealed with a Suba Seal rubber septum, placed under vacuum, flame-dried for 45 seconds to activate the molecular sieves, cooled under a purged and completely air-free argon balloon and wrapped in foil to exclude light. Once cooled, solvent (0.40 mL, 0.5 M to substrate) and substrate (0.20 mmol, 1 equiv) were added and stirred for 10 minutes. [Mn$^{III}$(ClPc)]Cl (23.1 mg, 0.020 mmol, 0.1 equiv) and silver hexafluoroantimonate (6.9 mg, 0.020 mmol, 0.1 equiv) were weighed in a foil wrapped 1 dram vial in the glove box and sealed with a Teflon cap. The vial was removed from the glove box and the contents added directly to the round bottom flask while maintaining an argon atmosphere then stirred for 10 minutes at room temperature. In a 1 dram vial open to air, 2,2,2-trichloroethyl (phenyl-$\lambda^3$-iodanylidene) sulfamate (172.2 mg, 0.40 mmol, 2 equiv) was weighed and added directly to the round bottom flask while maintaining an argon atmosphere. The Suba Seal rubber septum was replaced by a polyethylene cap, sealed tightly and placed in a 40° C. oil bath for 8 hours with stirring. Upon reaction completion, the reaction was filtered through a 1-inch silica gel plug using diethyl ether or ethyl acetate as the eluent. The crude material was concentrated and dry-loaded directly onto a silica gel column.

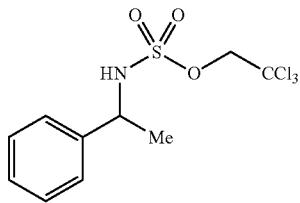

2,2,2-trichloroethyl (1-phenylethyl)sulfamate [5]

According to the general amination procedure B, 5 Å powdered molecular sieves (40 mg), ethyl benzene S3 (21.2 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was dry loaded onto a silica gel column. Flash chromatography using gradient elution (100 mL of 100% hexanes then 300 mL of 5% ethyl acetate in 95% hexanes followed by 600 mL of 7.5% ethyl acetate in 90% hexanes) gave the pure product as a yellow oil.

Run 1 (48 mg, 0.144 mmol, 72% yield).
Run 2 (48 mg, 0.144 mmol, 72% yield).
Run 3 (48 mg, 0.144 mmol, 72% yield).
Average overall yield: 72% yield±0.0.

$^1$H NMR (500 MHz, Chloroform-d): δ 7.41-7.34 (m, 4H), 7.34-7.30 (m, 1H), 5.15 (s, 1H), 4.73 (p, J=6.5 Hz, 1H), 4.41 (s, 2H), 1.63 (d, J=6.6 Hz, 3H).

$^{13}$C NMR (126 MHz, CDCl$_3$): δ 141.5, 129.1, 128.4, 126.4, 93.4, 78.2, 55.1, 23.0.

HRMS (ESI-TOF MS ES−): m/z calculated for C$_{10}$H$_{11}$NO$_3$SCl$_3$ [M−H]$^-$: 329.9525, found 329.9514.

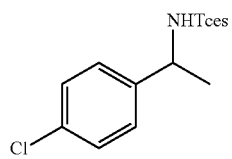

2,2,2-trichloroethyl (1-(4-chlorophenyl)ethyl)sulfamate [6]

According to the general amination procedure B, 5 Å powdered molecular sieves (40 mg), 1-chloro-4-ethylbenzene S4 (28.1 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (80 mL), the solvent was concentrated and the crude brown oil was loaded onto a silica gel column. Flash chromatography using gradient elution (100 mL of 100% hexanes then 700 mL of 5% ethyl acetate in 95% hexanes) gave the pure product as a yellow oil.

Run 1 (41.0 mg, 0.112 mmol, 56% yield).
Run 2 (42.3 mg, 0.115 mmol, 58% yield).
Run 3 (41.9 mg, 0.114 mmol, 57% yield).
Average overall yield: 57% yield±1.0.

$^1$H NMR (500 MHz, CDCl$_3$): δ 7.35 (d, J=8.5 Hz, 1H), 7.30 (d, J=8.5 Hz, 2H), 4.91 (br s, 1H), 4.73 (p, J=6.7 Hz, 1H), 4.51 (d, J=10.8 Hz, 1H), 4.48 (d, J=10.8 Hz, 1H), 1.61 (d, J=6.9 Hz, 3H).

$^{13}$C NMR (126 MHz, CDCl$_3$): δ 139.97, 134.22, 129.26, 127.82, 93.39, 78.25, 54.41, 22.94.

HRMS (ESI-TOF MS ES+): m/z calculated for C$_{10}$H$_{11}$NO$_3$NaSCl$_4$ [M+Na]$^+$: 387.9111, found 387.9117.

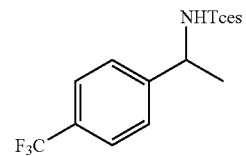

2,2,2-trichloroethyl (1-(4-(trifluoromethyl)phenyl)ethyl)sulfamate [7]

According to the general amination procedure B, 5 Å powdered molecular sieves (40 mg), 1-ethyl-4-(trifluoromethyl)benzene S5 (34.8 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$_3$-iodanylidene)sulfamate (172.2 mg, 0.40 mmol, 2 equiv) were combined in a 10 mL round-bottom flask and stirred for 8-12 h. After silica plug filtration using diethyl ether as the eluent (80 mL), the solvent was concentrated and the crude brown oil was loaded onto a silica gel column. Flash chromatography using gradient elution (800 mL of 5% ethyl acetate in 95% hexanes) gave the pure product as a yellow oil.

Run 1 (22.6 mg, 0.056 mmol, 28% yield).
Run 2 (24.2 mg, 0.060 mmol, 30% yield).
Run 3 (25.6 mg, 0.064 mmol, 32% yield).
Average overall yield: 30% yield±2.0.

$^1$H NMR (500 MHz, CDCl$_3$): δ 7.65 (d, J=8.1 Hz, 1H), 7.49 (d, J=8.1 Hz, 2H), 4.93 (br d, J=6.4 Hz, 1), 4.81 (p, J=6.8 Hz, 1, H), 4.8 (p, J=6.8 Hz, H), 4.51 (d, J=10.9 Hz, 1H), 4.49 (d, J=10.9 Hz, 1H), 1.64 (d, J=6.9 Hz, 3H).

$^{13}$C NMR (126 MHz, CDCl$_3$): δ 145.38, 130.69 (q, J=32.7 Hz), 126.82, 126.13 (q, J=3.7 Hz), 124.00 (q, J=272.2 Hz), 93.34, 78.26, 54.60, 23.06.

$^{19}$F NMR (470 MHz, CDCl$_3$): δ −63.15 (s, 3F).

HRMS (CI+): m/z calculated for C$_{11}$H$_{12}$NO$_3$SCl$_3$F$_3$ [M+H]$^+$: 399.95560, found 399.95510.

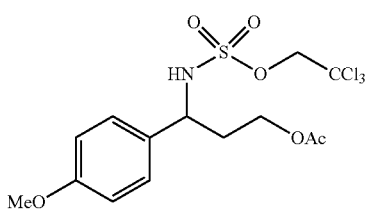

3-(4-methoxyphenyl)-3-(((2,2,2-trichloroethoxy)sulfonyl)amino)propyl acetate [8]

According to the general procedure B, 5 Å powdered molecular sieves (40 mg), 3-(4-methoxyphenyl)propyl acetate S6 (41.7 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (50 mL), the solvent was concentrated and the crude brown oil was dry loaded onto a silica gel column. Flash chromatography on 75 mL of silica using gradient elution (500 mL of 100% dichloromethane then 200 mL of 1% diethyl ether in 99% dichloromethane followed by 400 mL of 2% diethyl ether in 98% dichloromethane then 400 ml of 5% diethyl ether in 95% dichloromethane) gave the pure product as a white solid.

Run 1 (60.9 mg, 0.140 mmol, 70% yield).
Run 2 (56.5 mg, 0.130 mmol, 65% yield).
Run 3 (57.0 mg, 0.131 mmol, 66% yield).
Average overall yield: 67% yield±2.6.

$^1$H NMR (500 MHz, CDCl$_3$): δ 7.24 (d, J=8.5 Hz, 2H), 6.89 (d, J=8.5 Hz, 2H), 5.60 (br d, J=7.2 Hz, 1H), 4.63 (q, J=7.2 Hz, 1H), 4.35 (d, J=10.8 Hz, 1H), 4.29 (d, J=10.8 Hz, 1H), 4.13 (dt, J=11.6, 5.9 Hz, 1H), 3.99 (dt, J=11.7, 6.3 Hz, 1H), 3.79 (s, 3H), 2.28 (m, 1H), 2.15-2.08 (m, 1H), 2.04 (s, 3H).

$^{13}$C NMR (126 MHz, CDCl$_3$): δ 171.22, 159.75, 131.61, 127.99, 114.58, 93.38, 78.11, 61.17, 56.36, 55.49, 35.54, 21.02.

HRMS (ESI-TOF MS ES−): m/z calculated for C$_{14}$H$_{17}$Cl$_3$NO$_6$S [M−H]$^-$: 431.9842, found 431.9839.

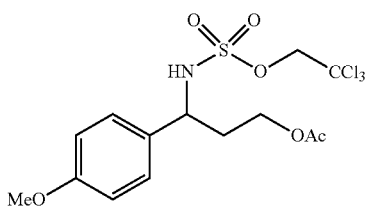

3-(4-bromophenyl)-3-(((2,2,2-trichloroethoxy)sulfonyl)amino)propyl acetate [9]

According to the general procedure B, 5 Å powdered molecular sieves (40 mg), 3-(4-bromophenyl)propyl acetate S7 (51.4 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (50 mL), the solvent was concentrated and the crude brown oil was loaded onto a silica gel column. Flash chromatography with 75 mL of silica using gradient elution (500 mL of 100% dichloromethane then 250 mL of 1% diethyl ether in 99% dichloromethane followed by 250 mL of 2% diethyl ether in 98% dichloromethane) gave the pure product as a white solid.

Run 1 (64.8 mg, 0.106 mmol, 53% yield).
Run 2 (63.0 mg, 0.110 mmol, 55% yield).
Run 3 (63.0 mg, 0.112 mmol, 56% yield).
Average overall yield: 55% yield.

$^1$H NMR (500 MHz, CDCl$_3$): δ 7.51 (d, J=8.4 Hz, 2H), 7.21 (d, J=8.4 Hz, 2H), 5.54 (d, J=7.5 Hz, 1H), 4.67 (q, J=7.3 Hz, 1H), 4.44 (d, J=10.8 Hz, 1H), 4.40 (d, J=10.8 Hz, 1H), 4.15 (ddd, J=11.9, 6.8, 5.2 Hz, 1H), 4.04 (ddd, J=11.8, 7.0, 5.2 Hz, 1H), 2.29-2.21 (m, 1H), 2.18-2.09 (m, 1H), 2.05 (s, 3H).

$^{13}$C NMR (126 MHz, CDCl$_3$): δ 171.17, 138.77, 132.48, 128.53, 122.70, 93.40, 78.25, 61.04, 56.54, 35.61, 21.13.

HRMS (ESI-TOF MS ES+): m/z calculated for C$_{13}$H$_{15}$NO$_5$NaSCl$_3$Br [M+Na]$^+$: 503.8818, found 503.8807.

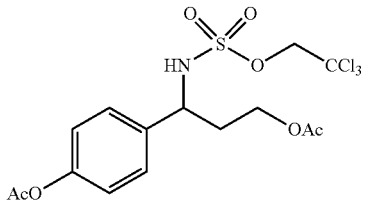

4-(3-acetoxy-1-(((2,2,2-trichloroethoxy)sulfonyl)amino)propyl)phenyl acetate [10]

According to the general procedure B, 5 Å powdered molecular sieves (40 mg), 3-(4-acetoxyphenyl)propyl acetate S8 (47.3 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (50 mL), the solvent was concentrated and the crude brown oil was dry loaded onto a silica gel column. Flash chromatography on 75 mL silica using gradient elution (500 mL of 100% dichloromethane then 200 mL of 2% diethyl ether in 98% dichloromethane followed by 400 mL of 4% diethyl ether in 96% dichloromethane then 400 ml of 8% diethyl ether in 92% dichloromethane) gave the product as a white solid with a minor impurity that was considered when calculating yield by the addition of mesitylene as an internal standard in the $^1$H NMR.

Run 1 (53.7 mg, 0.116 mmol, 58% yield).
Run 2 (53.7 mg, 0.116 mmol, 58% yield).
Run 3 (51.8 mg, 0.112 mmol, 56% yield).
Average overall yield: 57% yield±1.1.

$^1$H NMR (500 MHz, CDCl$_3$): δ 7.34 (d, J=8.5 Hz, 2H), 7.09 (d, J=8.5 Hz, 2H), 5.75 (d, J=6.9 Hz, 1H), 4.68 (q, J=7.1 Hz, 1H), 4.40 (d, J=10.8 Hz, 1H), 4.35 (d, J=10.8 Hz, 1H), 4.16 (ddd, J=11.9, 7.1, 5.2 Hz, 1H), 4.03 (ddd, J=11.8, 6.8, 5.1 Hz, 1H), 2.30 (s, 3H), 2.28-2.20 (m, 1H), 2.13 (dtd, J=14.0, 6.8, 5.0 Hz, 1H), 2.03 (s, 3H).

$^{13}$C NMR (126 MHz, CDCl$_3$): δ 171.18, 169.53, 150.70, 137.29, 127.88, 122.38, 93.33, 78.13, 61.03, 56.34, 35.56, 21.26, 21.00.

HRMS (ESI– TOF MS ES–): m/z calculated for C$_{15}$H$_{18}$Cl$_3$NO$_7$SNa [M+Na]$^+$: 483.9767, found 483.9775.

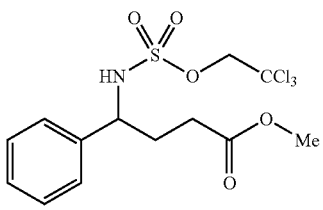

Methyl 4-phenyl-4-(((2,2,2-trichloroethoxy)sulfonyl)amino)butanoate [11]

According to the general procedure B, 5 Å powdered molecular sieves (40 mg), methyl 4-phenylbutanoate S9 (35.6 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as a clear and yellow oil.

Run 1 (57 mg, 0.141 mmol, 70% yield).
Run 2 (52 mg, 0.128 mmol, 64% yield).
Run 3 (53 mg, 0.131 mmol, 65% yield).
Average overall yield: 66% yield±3.2.

$^1$H NMR (500 MHz, Chloroform-d): δ 7.40-7.35 (m, 2H), 7.35-7.28 (m, 3H), 5.94 (d, J=7.4 Hz, 1H), 4.57 (q, J=7.3 Hz, 1H), 4.33 (d, J=10.8 Hz, 1H), 4.28 (d, J=10.8 Hz, 1H), 3.68 (s, 3H), 2.51-2.37 (m, 2H), 2.25 (dq, J=14.7, 7.4 Hz, 1H), 2.12 (dq, J=13.7, 6.7 Hz, 1H).

$^{13}$C NMR (126 MHz, CDCl$_3$): δ 174.3, 140.1, 129.2, 128.5, 126.7, 93.4, 78.1, 59.2, 52.2, 31.8, 30.8.

HRMS (ESI-TOF MS ES+): m/z calculated for C$_{13}$H$_{16}$NO$_5$SCl$_3$Na [M+Na]$^+$: 425.9712, found 425.9710.

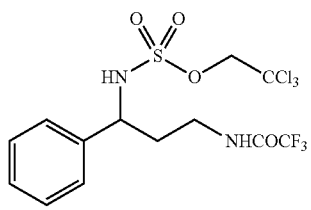

2,2,2-trichloroethyl (1-phenyl-3-(2,2,2-trifluoroacetamido)propyl)sulfamate [12]

According to the general amination procedure B, 5 Å powdered molecular sieves (40 mg), 2,2,2-trifluoro-N-(3-phenylpropyl)acetamide S10 (46.2 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as a light yellow solid.

Run 1 (61 mg, 0.133 mmol, 67% yield).
Run 2 (66 mg, 0.144 mmol, 72% yield).
Run 3 (61 mg, 0.133 mmol, 67% yield).
Average overall yield: 69% yield±2.9.

$^1$H NMR (500 MHz, Chloroform-d): δ 7.42-7.36 (m, 2H), 7.36-7.31 (m, 3H), 6.75 (s, 1H), 5.41 (d, J=8.1 Hz, 1H), 4.57 (q, J=7.7 Hz, 1H), 4.45 (d, J=10.8 Hz, 1H), 4.31 (d, J 10.8 Hz, 1H), 3.74-3.66 (m, 1H), 3.42-3.34 (m, 1H), 2.22-2.15 (m, 2H).

$^{13}$C NMR (126 MHz, CDCl$_3$): δ 157.9 (q, J=36.2 Hz), 139.6, 129.4, 128.9, 126.6, 115.8 (q, J=287.4 Hz), 93.1, 78.1, 57.2, 37.1, 35.5.

$^{19}$F NMR (470 MHz, Chloroform-d): δ −76.44.

HRMS (ESI-TOF MS ES+): m/z calculated for C$_{13}$H$_{14}$N$_2$O$_4$SCl$_3$F$_3$Na [M+Na]$^+$: 478.9590, found 478.9555.

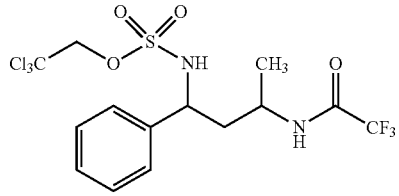

2,2,2-trichloroethyl (1-phenyl-3-(2,2,2-trifluoroacetamido)butyl)sulfamate [13]

According to the general procedure B, 5 Å powdered molecular sieves (40 mg), 2,2,2-trifluoro-N-(4-phenylbutan-2-yl)acetamide S11 (49.1 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was concentrated and the crude brown oil was loaded onto a silica gel column. Flash chromatography on 75 mL silica using gradient elution (500 mL of 100% dichloromethane then 200 mL of 1% diethyl ether in 99% dichloromethane followed by 400 mL of 2% diethyl ether in 98% dichloromethane) gave the pure product as a white solid in a 1:1 diasteromeric mixture. This compound was characterized as a mixture of diastereomers.

Run 1 (61 mg, 0.130 mmol, 65% yield).
Run 2 (58.5 mg, 0.124 mmol, 62% yield).
Run 3 (64.2 mg, 0.136 mmol, 68% yield).
Average overall yield: 65% yield±3.0 (1:1 d.r.).

$^1$H NMR (500 MHz, CDCl$_3$) (mixture of diastereomers): δ 7.42-7.29 (m, 5H), 6.57-6.48 (m, 1H), 6.24 (d, J=7.3 Hz, 0.5H), 5.91 (d, J=7.9 Hz, 0.5H), 4.62-4.51 (m, 1H), 4.33 (d, J=10.8 Hz, 0.5H), 4.32 (d, J=10.8 Hz, 0.5H), 4.21 (d, J=10.8 Hz, 0.5H), 4.18 (d, J=10.8 Hz, 0.5H), 4.15-3.99 (m, 1H), 2.31 (dt, J=14.6, 7.4 Hz, 0.5H), 2.21 (t, J=7.0 Hz, 0.5H), 1.95 (dt, J=13.9, 6.7 Hz, 1H), 1.33 (d, J=6.7 Hz, 1.5H), 1.29 (d, J=6.7 Hz, 1.5H).

$^{13}$C NMR (126 MHz, CDCl$_3$) (mixture of diastereomers): δ157.08 (q, J$_{CF}$=37.2 Hz), 156.96 (q, J$_{CF}$=37.3 Hz), 139.85, 139.29, 129.46, 129.38, 128.95, 128.82, 126.75, 126.63, 115.77 (q, J$_{CF}$=287.4 Hz), 115.75 (q, J$_{CF}$=287.9 Hz), 93.20, 93.18, 78.12, 78.09, 56.80, 56.72, 44.43, 44.27, 43.07, 41.91, 20.03, 19.97.

$^{19}$F NMR (471 MHz, CDCl$_3$): δ −75.92, −75.98. (diastereomers).

HRMS (ESI-TOF MS ES+): m/z calculated for C$_{14}$H$_{20}$Cl$_3$F$_3$N$_3$O$_4$S [M+NH$_4$]$^+$: 488.0192, found 488.0197.

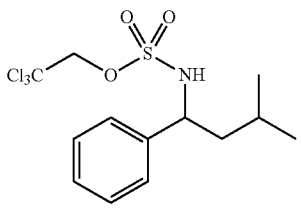

2,2,2-trichloroethyl
(3-methyl-1-phenylbutyl)sulfamate [14]

According to the general procedure B, 5 Å powdered molecular sieves (40 mg), isopentylbenzene S12 (29.7 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (50 mL), the solvent was concentrated and the crude brown oil was dry loaded onto a silica gel column. Flash chromatography using gradient elution (100 mL of 100% hexanes then 400 mL of 5% ethyl acetate in 95% hexanes followed by 200 mL of 10% ethyl acetate in 90% hexanes) gave the pure product as a colorless oil.

Run 1 (37.2 mg, 0.099 mmol, 50% yield).
Run 2 (41.2 mg, 0.110 mmol, 55% yield).
Run 3 (41.2 mg, 0.110 mmol, 55% yield).
Average overall yield: 53% yield±2.9.

$^1$H NMR (500 MHz, CDCl$_3$): δ 7.41-7.23 (m, 5H), 5.15 (br d, J=7.2 Hz, 1H), 4.57 (q, J=7.6 Hz, 1H), 4.26 (d, J=10.8 Hz, 1H), 4.22 (d, J=10.8 Hz, 1H), 1.80 (dt, J=14.5, 7.5 Hz, 1H), 1.67 (dt, J=13.9, 7.2 Hz, 1H), 1.62-1.51 (m, 1H), 0.94 (d, J=6.6 Hz, 6H).

$^{13}$C NMR (126 MHz, CDCl$_3$): δ 140.96, 129.14, 128.37, 126.78, 93.36, 78.10, 57.97, 46.29, 24.88, 22.56, 22.32.

HRMS (ESI− TOF MS ES−): m/z calculated for C$_{13}$H$_{17}$Cl$_3$NO$_3$S [M−H]$^-$: 371.9995, found 371.9991.

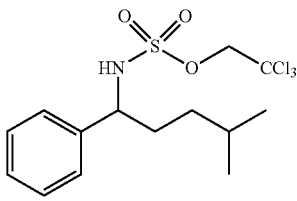

2,2,2-trichloroethyl
(4-methyl-1-phenylpentyl)sulfamate [15]

According to the general procedure B, 5 Å powdered molecular sieves (40 mg), (4-methylpentyl)benzene S13 (32.5 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (50 mL), the solvent was concentrated and the crude brown oil was dry loaded onto a silica gel column. Flash chromatography on 75 mL of silica using gradient elution (100 mL of 100% hexanes then 300 mL of 5% ethyl acetate in 95% hexanes followed by 600 mL of 10% ethyl acetate in 90% hexanes) gave the pure product as a colorless oil.

Run 1 (47 mg, 0.120 mmol, 60% yield).
Run 2 (45.1 mg, 0.116 mmol, 58% yield).
Run 3 (45.2 mg, 0.116 mmol, 58% yield).
Average overall yield: 59% yield±1.2.

$^1$H NMR (500 MHz, CDCl$_3$): δ 7.41-7.27 (m, 5H), 4.97 (br d, J=7.3 Hz, 1H), 4.46 (q, J=7.5 Hz, 1H), 4.32 (d, J=10.8 Hz, 1H), 4.28 (d, J=10.8 Hz, 1H), 1.99-1.89 (m, 1H), 1.87-1.76 (m, 1H), 1.61-1.48 (m, 1H), 1.33-1.19 (m, 1H), 1.16-1.02 (m, 1H), 0.86 (d, J=6.6 Hz, 6H).

$^{13}$C NMR (126 MHz, CDCl$_3$): δ 140.74, 129.13, 128.39, 126.78, 93.39, 78.13, 60.03, 35.14, 35.00, 27.88, 22.62, 22.52.

HRMS (ESI− TOF MS ES+): m/z calculated for C$_{14}$H$_{19}$Cl$_3$NO$_3$S [M−H]$^-$: 386.0157, found 386.0145.

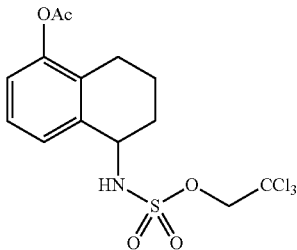

5-(((2,2,2-trichloroethoxy)sulfonyl)amino)-5,6,7,8-tetrahydronaphthalen-1-yl acetate [16]

According to the general amination procedure B, 5 Å powdered molecular sieves (40 mg), 5,6,7,8-tetrahydronaphthalen-1-yl acetate S14 (38.0 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ³-iodanylidene) sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (100 mL of 100% hexanes then 300 mL of 5% acetone in 95% hexanes followed by 600 mL of 7.5% acetone in 92.5% hexanes) gave the pure product as a clear and yellow oil.

Run 1 (56 mg, 0.134 mmol, 67% yield).
Run 2 (60 mg, 0.144 mmol, 72% yield).
Run 3 (58 mg, 0.139 mmol, 70% yield).
Average overall yield: 70% yield±2.5.

$^1$H NMR (500 MHz, CDCl$_3$): δ 7.42 (d, J=7.8 Hz, 1H), 7.28-7.21 (m, 1H), 7.00-6.93 (m, 1H), 5.05 (d, J=7.8 Hz, 1H), 4.82-4.76 (m, 1H), 4.67 (s, 2H), 2.62 (dt, J=17.4, 5.7 Hz, 1H), 2.51 (dt, J=17.3, 7.1 Hz, 1H), 2.30 (s, 3H), 2.12-2.05 (m, 2H), 1.89-1.80 (m, 2H).

$^{13}$C NMR (126 MHz, CDCl$_3$): δ 169.4, 149.0, 136.5, 130.4, 127.2, 127.2, 121.8, 93.7, 78.2, 53.3, 29.8, 23.0, 20.9, 18.2.

HRMS (ESI-TOF MS ES+): m/z calculated for C$_{14}$H$_{16}$NO$_5$SCl$_3$Na [M+Na]$^+$: 437.9712, found 437.9707.

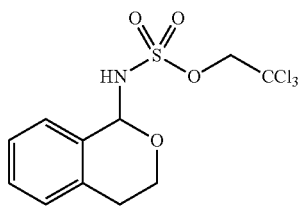

2,2,2-trichloroethyl isochroman-1-ylsulfamate [17]

According to the general amination procedure B, 5 Å powdered molecular sieves (40 mg), isochroman S15 (46.2 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ³-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was dry loaded onto a silica gel column. Flash chromatography using gradient elution (100 mL of 100% hexanes then 300 mL of 5% ethyl acetate in 95% hexanes followed by 600 mL of 10% ethyl acetate in 90% hexanes) gave the pure product as a yellow solid.

Run 1 (44 mg, 0.122 mmol, 61% yield).
Run 2 (41 mg, 0.114 mmol, 57% yield).
Run 3 (45 mg, 0.125 mmol, 62% yield)
Average overall yield: 60% yield±2.6.

$^1$H NMR: (500 MHz, Chloroform-d): δ 7.33-7.22 (m, 3H), 7.15 (d, J=7.3 Hz, 1H), 6.06 (d, J=8.3 Hz, 1H), 5.77 (d, J=8.3 Hz, 1H), 4.80 (d, J=10.9 Hz, 1H), 4.73 (d, J=10.8 Hz, 1H), 4.06-4.01 (m, 2H), 3.00-2.91 (m, 1H), 2.79-2.72 (m, 1H).

$^{13}$C NMR (126 MHz, CDCl$_3$): δ 134.7, 131.7, 129.1, 129.0, 127.1, 127.0, 93.6, 80.6, 78.6, 59.8, 27.7.

HRMS (ESI-TOF MS ES-): m/z calculated for C$_{11}$H$_{11}$NO$_4$SCl$_3$ [M-H]$^-$: 357.9474, found 357.9467.

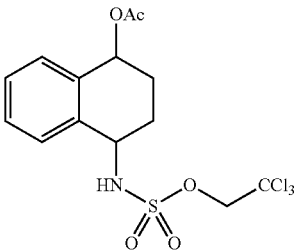

4-(((2,2,2-trichloroethoxy)sulfonyl)amino)-1,2,3,4-tetrahydronaphthalen-1-yl acetate [18]

According to the general amination procedure B, 5 Å powdered molecular sieves (40 mg), 1,2,3,4-tetrahydronaphthalen-1-yl acetate S16 (38.0 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ³-iodanylidene) sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as a white solid in equal amounts of inseparable diastereomers.

Run 1 (50 mg, 0.120 mmol, 60% yield).
Run 2 (52 mg, 0.124 mmol, 62% yield).
Run 3 (48 mg, 0.115 mmol, 58% yield).
Average overall yield: 60% yield±2.0 (1:1 d.r.).

$^1$H NMR (500 MHz, Chloroform-d) (mixture of diastereomers): δ 7.59 (d, J=7.4 Hz, 0.5H), 7.53 (d, J=7.4 Hz, 0.5H), 7.40-7.35 (m, 1H), 7.35-7.30 (m, 2H), 5.99 (t, J=4.4 Hz, 0.5H), 5.92 (t, J=5.2 Hz, 0.5H), 5.05 (d, J=8.0 Hz, 0.5H), 4.94-4.88 (m, 0.5H), 4.88-4.83 (m, 0.5H), 4.76 (td, J=7.9, 5.1 Hz, 0.5H), 4.70 (s, 1H), 4.69 (s, 1H) 2.40-2.31 (m, 0.5H), 2.31-2.22 (m, 0.5H), 2.22-2.10 (m, 2.5H), 2.09 (s, 1.5H), 2.07 (s, 1.5H), 2.02-1.95 (m, 0.5H).

$^{13}$C NMR (126 MHz, CDCl$_3$) (mixture of diastereomers): δ 170.8, 170.7, 135.7, 135.4, 135.2, 135.1, 129.9, 129.6, 129.5, 129.4, 129.3, 129.1, 128.9, 128.5, 93.7, 93.6, 78.3, 78.2, 69.4, 68.7, 53.5, 52.9, 26.9, 26.0, 25.8, 24.9, 21.5, 21.4.

HRMS (ESI-TOF MS ES+): m/z calculated for C$_{14}$H$_{16}$NO$_5$SCl$_3$Na [M+Na]$^+$: 437.9712, found 437.9704.

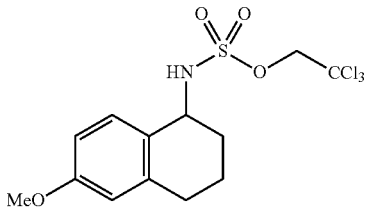

2,2,2-trichloroethyl (6-methoxy-1,2,3,4-tetrahydronaphthalen-1-yl)sulfamate [19]

According to the general procedure B, 5 Å powdered molecular sieves (40 mg), 6-methoxy-1,2,3,4-tetrahydronaphthalene S17 (32.5 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$^{3-}$iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was concentrated and the crude brown oil was dry loaded onto a silica gel column. Flash chromatography using gradient elution (400 mL of 5% ethyl acetate in hexane followed by 400 mL of 10% ethyl acetate in hexanes) gave the pure product as well as the imine by-product as off-white solids.

Run 1 (46.5 mg, 0.120 mmol, 60% yield+imine (10.2 mg, 0.026 mmol, 13% yield)).

Run 2 (47.3 mg, 0.122 mmol, 61% yield+imine (10.0 mg, 0.026 mmol, 13% yield)).

Run 3 (41 mg, 0.106 mmol, 53% yield+imine (7.0 mg, 0.014 mmol, 9% yield)).

Average overall yield: 58% yield+4.4.

$^1$H NMR (500 MHz, CDCl$_3$): δ 7.39 (d, J=8.6 Hz, 1H), 6.76 (dd, J=8.6, 2.7 Hz, 1H), 6.61 (d, J=2.7 Hz, 1H), 4.83 (d, J=7.7 Hz, 1H), 4.76-4.72 (m, 1H), 4.67 (s, 2H), 3.78 (s, 3H), 2.79 (dt, J=17.0, 5.4 Hz, 1H), 2.76-2.66 (m, 1H), 2.16-2.09 (m, 1H), 2.08-2.01 (m, 1H), 1.89-1.79 (m, 2H).

$^{13}$C NMR (126 MHz, CDCl$_3$): δ 159.35, 139.22, 130.69, 126.75, 113.77, 113.12, 93.75, 78.18, 55.40, 53.19, 30.46, 29.31, 18.90.

HRMS (ESI– TOF MS ES–): m/z calculated for C$_{13}$H$_{15}$Cl$_3$NO$_4$S [M–H]$^-$: 385.9787, found 385.9784.

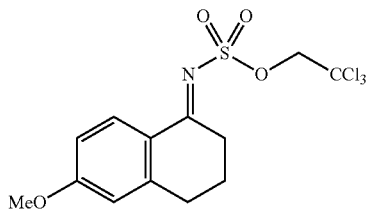

2,2,2-trichloroethyl-(6-methoxy-3,4-dihydronaphthalen-1(2H)-ylidene)sulfamate [S18]

Isolated as part of the oxidation reaction of 6-methoxy-1,2,3,4-tetrahydronaphthalene.

$^1$H NMR (500 MHz, CDCl$_3$): δ 8.17 (d, J=8.9 Hz, 1H), 6.84 (dd, J=9.0, 2.6 Hz, 1H), 6.71 (d, J=2.4 Hz, 1H), 4.84 (s, 2H), 3.88 (s, 3H), 3.26-3.20 (m, 2H), 2.89 (t, J=6.1 Hz, 2H), 2.04 (dq, J=7.1, 6.1 Hz, 2H).

$^{13}$C NMR (126 MHz, CDCl$_3$): δ 182.65, 165.06, 147.98, 130.66, 124.36, 114.17, 113.11, 93.61, 79.28, 55.77, 33.21, 29.96, 22.55.

HRMS (ESI– TOF MS ES+): m/z calculated for C$_{13}$H$_{15}$Cl$_3$NO$_4$ [M+H]$^+$: 385.9787, found 385.9778.

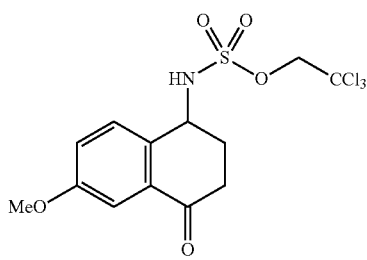

2,2,2-trichloroethyl (6-methoxy-4-oxo-1,2,3,4-tetrahydronaphthalen-1-yl)sulfamate [20]

According to the general procedure B, 5 Å powdered molecular sieves (40 mg), (4-methylpentyl)benzene S19 (35.2 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was concentrated and the crude brown oil was loaded onto a silica gel column. Flash chromatography on 75 mL of silica using gradient elution (500 mL of 100% dichloromethane then 200 mL of 1% diethyl ether in 99% dichloromethane followed by 200 mL of 2% diethyl ether in dichloromethane and then 200 mL of 5% diethyl ether in 95% dichloromethane) gave the pure product as a colorless oil.

Run 1 (42.7 mg, 0.106 mmol, 53% yield).

Run 2 (41.0 mg, 0.102 mmol, 51% yield).

Run 3 (40.3 mg, 0.100 mmol, 50% yield).

Average overall yield: 51% yield+1.5.

$^1$H NMR (500 MHz, CDCl$_3$): δ 7.53 (d, J=8.6 Hz, 1H), 7.41 (d, J=2.8 Hz, 1H), 7.14 (dd, J=8.5, 2.8 Hz, 1H), 5.43 (br d, J=7.8 Hz, 1H), 4.91 (td, J=7.1, 4.0 Hz, 1H), 4.71 (d, J=10.9 Hz, 1H), 4.69 (d, J=10.9 Hz, 1H), 3.82 (s, 3H), 2.86 (ddd, J=17.6, 9.3, 4.6 Hz, 1H), 2.65 (ddd, J=17.7, 7.6, 4.6 Hz, 1H), 2.48 (ddt, J=13.6, 9.0, 4.3 Hz, 1H), 2.41-2.32 (m, 1H).

$^{13}$C NMR (126 MHz, CDCl$_3$): δ 196.64, 160.15, 133.38, 133.11, 129.80, 122.43, 109.96, 93.59, 78.26, 55.77, 52.77, 34.73, 29.77.

HRMS (ESI– TOF MS ES+): m/z calculated for C$_{13}$H$_{15}$Cl$_3$NO$_5$S [M+H]$^+$: 401.9737, found 401.9727.

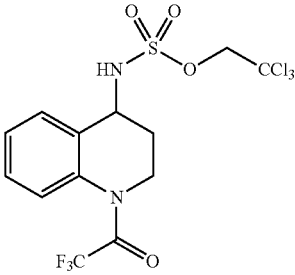

2,2,2-trichloroethyl (1-(2,2,2-trifluoroacetyl)-1,2,3,4-tetrahydroquinolin-4-yl)sulfamate [21]

According to the general amination procedure B, 5 Å powdered molecular sieves (40 mg), 1-(3,4-dihydroquinolin-1(2H)-yl)-2,2,2-trifluoroethan-1-one S20 (46.0 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (50 mL), the solvent was concentrated and the crude brown oil was dry loaded onto a silica gel column. Flash chromatography on 75 mL silica using gradient elution (100 mL of 100% hexanes then 400 mL of 5% ethyl acetate in 95% hexanes followed by 200 mL of 10% ethyl acetate in 90% hexanes) gave the pure product as a white solid.

Run 1 (71.1 mg, 0.156 mmol, 78% yield).
Run 2 (68.3 mg, 0.150 mmol, 75% yield).
Run 3 (69.3 mg, 0.152 mmol, 76% yield).
Average overall yield: 76% yield+1.5.

$^1$H NMR (500 MHz, CDCl$_3$ at 50° C.): δ 7.68 (d, J=7.5 Hz, 1H), 7.55 (d, J=7.6 Hz, 1H), 7.34 (t, J=7.55 Hz, 1H), 7.28 (t, J=7.4 Hz, 1H), 5.35 (d, J=7.5 Hz, 1H), 4.85 (q, J=6.3 Hz, 1H), 4.70-4.64 (m, 2H), 3.90 (t, J=5.9 Hz, 2H), 2.44 (dq, J=12.3, 6.0 Hz, 1H), 2.33 (dq, J=11.8, 5.9 Hz, 1H).

$^{13}$C NMR (126 MHz, CDCl$_3$ at 50° C.): δ 156.16 (q, J=36.3 Hz), 136.86, 129.25, 129.10, 128.75, 127.42, 124.71, 116.63 (q, J$_{CF}$=288.3 Hz), 93.68, 78.45, 51.05, 42.80, 31.35.

$^{19}$F NMR (471 MHz, DMSO at 23° C.): δ −68.19, −75.08 (rotational isomers).

HRMS (ESI− TOF MS ES+): m/z calculated for C$_{13}$H$_{16}$C$_{13}$F$_3$N$_3$O$_4$S [M+NH$_4$]$^+$: 471.9879, found 471.9880.

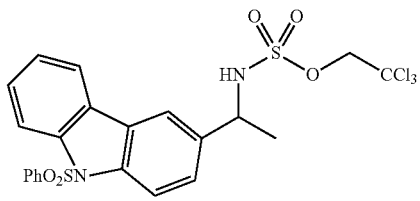

2,2,2-trichloroethyl (1-(9-(phenylsulfonyl)-9H-carbazol-3-yl)ethyl)sulfamate [22]

According to the general amination procedure B, 5 Å powdered molecular sieves (40 mg), 3-ethyl-9-(phenylsulfonyl)-9H-carbazole S21 (67.1 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as an orange solid.

Run 1 (70 mg, 0.125 mmol, 62% yield).
Run 2 (74 mg, 0.132 mmol, 66% yield).
Run 3 (75 mg, 0.133 mmol, 67% yield).
Average overall yield: 65% yield+2.6.

$^1$H NMR (500 MHz, Chloroform-d): δ 8.30 (dd, J=9.9, 8.5 Hz, 2H), 7.93-7.86 (m, 2H), 7.81 (dd, J=8.5, 1.3 Hz, 2H), 7.54-7.44 (m, 3H), 7.41-7.31 (m, 3H), 5.12 (d, J=7.1 Hz, 1H), 4.90 (p, J=6.9 Hz, 1H), 4.48 (d, J=10.8 Hz, 1H), 4.45 (d, J=10.8 Hz, 1H), 1.70 (d, J=6.8 Hz, 3H).

$^{13}$C NMR (126 MHz, CDCl$_3$): δ 138.8, 138.0, 137.9, 137.3, 134.1, 129.3, 128.0, 126.9, 126.6, 126.0, 125.7, 124.3, 120.3, 118.1, 115.5, 115.2, 93.4, 78.2, 55.0, 23.2.

HRMS (ESI-TOF MS ES+): m/z calculated for C$_{22}$H$_{19}$N$_2$O$_5$S$_2$Cl$_3$Na [M+Na]$^+$: 582.9699, found 582.9702.

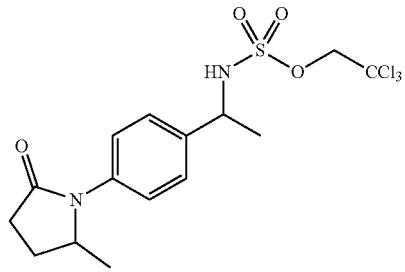

2,2,2-trichloroethyl (1-(4-(2-methyl-5-oxopyrrolidin-1-yl)phenyl)ethyl)sulfamate [23]

According to the general amination procedure B, 5 Å powdered molecular sieves (40 mg), 1-(4-ethylphenyl)-5-methylpyrrolidin-2-one S22 (40.7 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was concentrated and the crude brown oil was loaded onto a silica gel column. Flash chromatography on 75 mL silica using gradient elution (500 mL of 100% dichloromethane then 200 mL of 5% diethyl ether in 95% dichloromethane followed by 400 mL of 10% diethyl ether in 90% dichloromethane and then 200 mL of 20% diethyl ether in 80% dichloromethane and finally 400 mL of 50% diethyl ether in 50% dichloromethane) gave the pure product as an off-white oil in a 1:1 diastereomeric mixture. This compound was characterized as a mixture of diastereomers.

Run 1 (56.0 mg, 0.130 mmol, 65% yield).
Run 2 (53.3 mg, 0.124 mmol, 62% yield).
Run 3 (52.0 mg, 0.121 mmol, 61% yield).
Average overall yield: 63% yield±2.1 (1:1 d.r.).

$^1$H NMR (500 MHz, CDCl$_3$) (mixture of diastereomers): δ 7.41-7.34 (m, 4H), 5.64 (d, J=7.5 Hz, 0.5H), 5.61 (d, J=7.4 Hz, 0.5H), 4.71 (dq, J=6.9 Hz, 0.5H), 4.71 (dq, J=6.9 Hz, 0.5H), 4.47 (d, J=10.8 Hz, 0.5H), 4.47 (d, J=10.8 Hz, 0.5H), 4.43 (d, J=10.8 Hz, 1H), 4.36-4.25 (m, 1H), 2.71-2.62 (m, 1H), 2.60-2.51 (m, 1H), 2.43-2.34 (m, 1H), 1.82-1.71 (m, 1H), 1.60 (d, J=6.5 Hz, 1.5H), 1.58 (d, J=6.5 Hz, 1.5H), 1.26 (d, J=6.2 Hz, 1.5H), 1.24 (d, J=6.2 Hz, 1.5H).

$^{13}$C NMR (126 MHz, CDCl$_3$) (mixture of diastereomers): δ 174.92, 139.59, 139.52, 137.03, 136.98, 127.15, 127.06, 124.28, 124.21, 93.59, 93.57, 78.05, 55.87, 55.85, 54.38, 54.34, 31.46, 26.71, 26.69, 23.24, 22.92, 20.21.

HRMS: (ESI− TOF MS ES+): m/z calculated for C$_{15}$H$_{20}$N$_2$O$_4$SCl$_3$ [M+H]$^+$: 429.0209, found 429.0209.

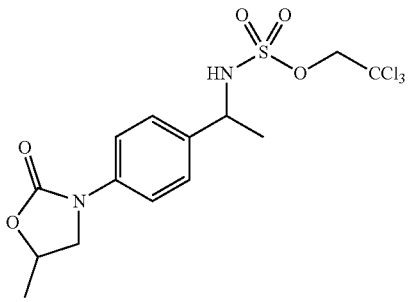

2,2,2-trichloroethyl (1-(4-(5-methyl-2-oxooxazolidin-3-yl)phenyl)ethyl)sulfamate [24]

According to the general amination procedure B, 5 Å powdered molecular sieves (40 mg), 3-(4-ethylphenyl)-5-methyloxazolidin-2-one S23 (41.1 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)[3]-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was concentrated and the crude brown oil was loaded onto a silica gel column. Flash chromatography on 75 mL silica using gradient elution (500 mL of 100% dichloromethane then 200 mL of 1% diethyl ether in 99% dichloromethane followed by 400 mL of 2% diethyl ether in 98% dichloromethane and then 200 mL of 5% diethyl ether in 95% dichloromethane) gave the pure product as an off-white solid in a 1:1 diastereomeric mixture.

This compound was characterized as a mixture of diastereomers.

Run 1 (45.0 mg, 0.104 mmol, 52% yield).
Run 2 (44.9 mg, 0.104 mmol, 52% yield).
Run 3 (41.4 mg, 0.096 mmol, 48% yield).
Average overall yield: 51% yield+2.3 (1:1 d.r.).

$^1$H NMR (500 MHz, CDCl$_3$) (mixture of diastereomers): δ 7.50 (d, J=8.7 Hz, 2H), 7.37 (d, J=8.6 Hz, 2H), 5.47 (s, 1H), 4.79 (sxt, J=6.3 Hz, 1H), 4.75-4.66 (m, 1H), 4.50 (d, J=10.8 Hz, 1H), 4.45 (d, J=10.8 Hz, 1H), 4.10 (td, J=8.5, 3.5 Hz, 1H), 3.61 (ddd, J=8.6, 7.1, 2.6 Hz, 1H), 1.60 (d, J=6.9 Hz, 3H), 1.53 (d, J=6.2 Hz, 3H).

$^{13}$C NMR (126 MHz, CDCl$_3$) (mixture of diastereomers): δ 155.15, 138.21, 137.33, 127.19, 118.71, 93.55, 78.21, 69.94, 69.93, 54.43, 52.01, 52.00, 22.92, 22.91, 20.82, 20.80.

HRMS (ESI-TOF MS ES+): m/z calculated for C$_{14}$H$_{18}$N$_2$O$_5$SCl$_3$ [M+H]$^+$: 431.0002, found 431.0006.

General Amination Procedure C for Benzylic C—H Amination of 3° Amines and Pyridines.

To a 1 dram vial equipped with a stir bar were added the nitrogen-containing substrate (0.20 mmol, 1.0 equiv.) and methylene chloride (DCM) (0.8 mL). Tetrafluoroboric acid diethyl ether complex (HBF$_4$.OEt$_2$) (30.2 μL, 35.6 mg, 0.22 mmol, 1.1 equiv.) was added dropwise while stirring. The reaction mixture was stirred for 1 h at room temperature. Upon reaction completion, the stir bar was removed, and the mixture was concentrated in vacuo and placed on vacuum overnight. In a 10 mL round-bottom flask equipped with a stir bar was added 40 mg of powdered 3 Å molecular sieves. The flask was then flame-dried under vacuum for 45 seconds, and refilled with argon using a thrice purged argon-filled balloon. In the 1-dram vial carrying the protonated substrate was added 0.2 mL of anhydrous 1,2-dichloroethane (DCE). The resulting solution or suspension was added into the round-bottom flask containing the 3 Å molecular sieves. This process is repeated 2× with 0.1 mL DCE each time to ensure complete transfer. The reaction flask was then wrapped in aluminum foil and stirred for 10 min, upon which time manganese (III) perchlorophthalocyanine chloride (23.1 mg, 0.02 mmol, 0.10 equiv.) and silver hexafluoroantimonate (AgSbF$_6$) (6.9 mg, 0.02 mmol, 0.10 equiv.) were added while maintaining an argon atmosphere. The mixture was stirred for 10 min, and 2,2,2-trichloroethyl (phenyl-λ$^3$-iodanylidene)sulfamate (PhI=NTces) (172.2 mg, 0.40 mmol, 2.0 equiv.) was added while maintaining an argon atmosphere. The septum was replaced by a polyethylene yellow cap, and the flask was placed into 40° C. oil bath and stirred for 15 h. Upon completion, the flask was removed from the oil bath. Sodium hydroxide solution (1M, 3 mL) and DCM (3 mL) were then added. The reaction mixture was vigorously stirred for 15 min, and the layers were separated. The aqueous layer was extracted with CH$_2$Cl$_2$ (3×5 mL). The organic layers were combined, dried over anhydrous potassium carbonate, filtered and concentrated via rotary evaporation. The crude material was purified by flash chromatography to afford the aminated product. (Note: Significant ketone byproduct formation and yield decrease were observed when an aged bottle of HBF$_4$.OEt$_2$ was used, possibly due to water absorption and/or decomposition).

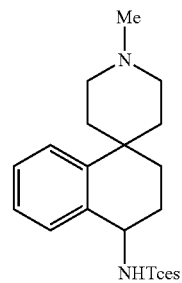

2,2,2-trichloroethyl (1'-methyl-3,4-dihydro-2H-spiro[naphthalene-1,4'-piperidin]-4-yl)sulfamate [26]

According to the general amination procedure C, 1'-methyl-3,4-dihydro-2H-spiro[naphthalene-1,4'-piperidine] 25 (64.6 mg, 0.30 mmol, 1.0 equiv.) in CH$_2$Cl$_2$ (1.2 mL) was protonated with HBF$_4$.OEt$_2$ (45.3 μL, 53.4 mg, 0.33 mmol, 1.1 equiv.), reacted with manganese (III) perchlorophthalocyanine chloride (34.6 mg, 0.030 mmol, 0.10 equiv.), AgSbF$_6$ (10.3 mg, 0.030 mmol, 0.10 equiv.), PhI=NTces (258.3 mg, 0.60 mmol, 2.0 equiv.), and 5 Å molecular sieves (60 mg) in DCE (0.6 mL) for 15 h. Following work-up, the crude material was purified by flash chromatography (50 mL basic Al$_2$O$_3$Brockmann grade III, gradient elution 25% EtOAc/Hex (4 column volumes)→0%→1%→2%→3% MeOH/CH$_2$Cl$_2$ (2 column volumes each)), staining with KMnO$_4$ to afford the product as a green oil. To remove the minimal co-eluding manganese catalyst, the product was re-dissolved in CH$_2$Cl$_2$ (10 mL) and extracted with 3M HCl (2×10 mL) and water (2×10 mL). The aqueous layers were combined and basified with 50% NaOH, extracted with CH$_2$Cl$_2$ (3×10 mL). The organic layers were combined, dried over K$_2$CO$_3$, and concentrated via rotary evaporation to afford the pure product as a white solid. The remaining organic layer after the acid wash was also basified and extracted likewise to afford the product as a white solid with discoloration.

Run 1 (78.9 mg, 0.18 mmol, 60% yield; 3.1 mg, 0.014 mmol, 5% rsm).
Run 2 (68.4 mg, 0.15 mmol, 52% yield; 9.6 mg, 0.045 mmol, 15% rsm).
Run 3 (81.0 mg, 0.18 mmol, 61% yield; 6.5 mg, 0.030 mmol, 10% rsm).
Average overall yield: 58% (10% rsm)+4.9.

$^1$H NMR (500 MHz, CDCl$_3$): δ 7.49 (d, J=7.6 Hz, 1H), 7.43 (d, J=7.8 Hz, 1H), 7.29 (t, J=7.4 Hz, 1H), 7.21 (t, J=7.4 Hz, 1H), 4.73 (t, J=5.3 Hz, 1H), 4.69 (s, 2H), 2.69 (d, J=11.4

Hz, 1H), 2.66 (d, J=11.4 Hz, 1H), 2.31 (s, 3H), 2.27-2.17 (m, 2H), 2.17-1.94 (m, 4H), 1.90 (app t, J=5.8 Hz, 2H), 1.51 (t, J=12.9 Hz, 2H).

$^{13}$C NMR (126 MHz, CDCl$_3$): δ 145.61, 134.79, 129.01, 128.81, 127.35, 126.66, 93.83, 78.10, 54.20, 51.57, 46.45, 38.26, 37.62, 34.82, 29.83, 26.24, 25.95.

HRMS (ESI-TOF MS ES−): m/z calculated for C$_{17}$H$_{24}$C$_{13}$N$_2$O$_3$S [M+H]$^+$: 441.0573, found 441.0565.

Scheme 1e, Entry 1: Reaction without HBF$_4$ protection and base workup. Run 1 (0 mg, 0 mmol, 0% yield; 30.4 mg, 0.141 mmol, 47% rsm).

Scheme 1e, Entry 3: Reaction with BF$_3$ protection (40.7 µL, 46.8 mg, 0.33 mmol, 1.1 equiv.) and base workup (1M NaOH, 5 mL, 4 h). Run 1 (64.8 mg, 0.147 mmol, 49% yield; 1.9 mg, 0.0090 mmol, 3% rsm). Run 2 (70.3 mg, 0.159 mmol, 53% yield; 1.3 mg, 0.0060 mmol, 2% rsm).

Average overall yield: 51% (2% rsm).

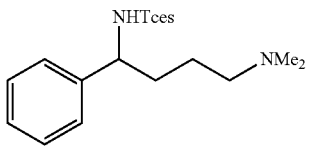

2,2,2-trichloroethyl (4-(dimethylamino)-1-phenylbutyl)sulfamate [27]

According to the general amination procedure C, N,N-dimethyl-4-phenylbutan-1-amine S24 (35.5 mg, 0.20 mmol, 1.0 equiv.) was protonated with HBF$_4$.OEt$_2$ (30.2 µL, 35.6 mg, 0.22 mmol, 1.1 equiv.), reacted with manganese (III) perchlorophthalocyanine chloride (34.6 mg, 0.030 mmol, 0.15 equiv.), AgSbF$_6$ (10.3 mg, 0.030 mmol, 0.15 equiv.), PhI=NTces (258.3 mg, 0.60 mmol, 3.0 equiv.), and 5 Å molecular sieves (40 mg) in DCE (0.4 mL). PhI=NTces was added in one portion. Following work-up, the crude material was purified by flash chromatography (50 mL basic Al$_2$O$_3$Brockmann grade III, gradient elution 30% EtOAc/Hex (4 column volumes)→0%→1%→2%→3% MeOH/CH$_2$Cl$_2$ (2 column volumes each)), staining with KMnO$_4$. The resulting solid was redissolved in acetonitrile, and the undissolved green solid was removed. The solution was concentrated via rotary evaporation to afford the product as a light yellow oil.

Run 1 (40.5 mg, 0.10 mmol, 50% yield; 4.7 mg, 0.027 mmol, 13% rsm).
Run 2 (39.2 mg, 0.097 mmol, 49% yield; 3.8 mg, 0.021 mmol, 11% rsm).
Run 3 (41.0 mg, 0.10 mmol, 51% yield; 2.4 mg, 0.014 mmol, 7% rsm).

Average overall yield: 50% (10% rsm)+1.0.

$^1$H NMR (500 MHz, CDCl$_3$): δ 7.39-7.30 (m, 4H), 7.24 (d, J=6.9 Hz, 1H), 4.56 (t, J=4.6 Hz, 1H), 4.38 (d, J=11.2 Hz, 1H), 4.35 (d, J=11.3 Hz, 1H), 2.46 (dt, J=11.4, 4.9 Hz, 1H), 2.34 (s, 6H), 2.34-2.27 (m, 1H), 2.10-2.00 (m, 2H), 1.58 (p, J=4.8 Hz, 2H).

$^{13}$C NMR (126 MHz, CDCl$_3$): δ 141.99, 128.54, 127.33, 126.64, 94.16, 77.70, 59.66, 57.57, 44.63, 37.76, 23.03.

HRMS (ESI-TOF MS ES+): m/z calculated for C$_{14}$H$_{22}$C$_{13}$N$_2$O$_3$S [M+H]$^+$: 403.0417, found 403.0409.

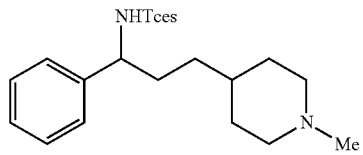

2,2,2-trichloroethyl (3-(1-methylpiperidin-4-yl)-1-phenylpropyl)sulfamate [28]

According to the general amination procedure C, 1-methyl-4-(3-phenylpropyl)piperidine S25 (43.5 mg, 0.20 mmol, 1.0 equiv.) was protonated with HBF$_4$.OEt$_2$ (30.2 µL, 35.6 mg, 0.22 mmol, 1.1 equiv.), reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 5 Å molecular sieves (40 mg) in DCE (0.4 mL). After 2 h of reaction, another batch of PhI=NTces (86.1 mg, 0.20 mmol, 1.0 equiv.) was quickly added to the reaction mixture. The reaction was further stirred for 13 h. Following work-up, the crude material was purified by flash chromatography (50 mL basic Al$_2$O$_3$Brockmann grade III, gradient elution 30% EtOAc/Hex (4 column volumes)→0%→1%→2%→3% MeOH/CH$_2$Cl$_2$ (2 column volumes each)), staining with KMnO$_4$ to afford the product as a white solid with green discoloration.

Run 1 (53.9 mg, 0.12 mmol, 61% yield; 7.1 mg, 0.033 mmol, 16% rsm).
Run 2 (47.4 mg, 0.11 mmol, 53% yield; 7.6 mg, 0.035 mmol, 17% rsm).
Run 3 (51.0 mg, 0.11 mmol, 57% yield; 8.0 mg, 0.037 mmol, 18% rsm).

Average overall yield: 57% (17% rsm)+4.0.

$^1$H NMR (500 MHz, CDCl$_3$): δ 7.36 (d, J=7.2 Hz, 2H), 7.33-7.27 (m, 3H), 4.46 (t, J=7.4 Hz, 1H), 4.33 (d, J=10.8 Hz, 1H), 4.29 (d, J=10.8 Hz, 1H), 2.81 (d, J=11.4 Hz, 2H), 2.21 (s, 3H), 2.02-1.90 (m, 1H), 1.90-1.78 (m, 3H), 1.62 (d, J=9.2 Hz, 2H), 1.40-1.28 (m, 1H), 1.28-1.14 (m, 4H).

$^{13}$C NMR (126 MHz, CDCl$_3$): δ 140.75, 129.12, 128.39, 126.78, 93.47, 78.07, 59.91, 56.00, 46.53, 35.00, 34.25, 32.96, 32.38, 32.31.

HRMS (ESI-TOF MS ES+): m/z calculated for C$_{17}$H$_{26}$C$_{13}$N$_2$O$_3$S [M+H]$^+$: 443.0730, found 443.0727.

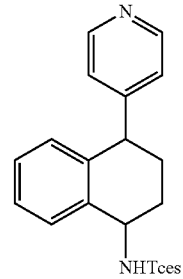

2,2,2-trichloroethyl (4-(pyridin-4-yl)-1,2,3,4-tetrahydronaphthalen-1-yl)sulfamate [29]

According to the general amination procedure C, 4-(1,2,3,4-tetrahydronaphthalen-1-yl)pyridine S26 (41.9 mg, 0.20 mmol, 1.0 equiv.) was protonated with HBF$_4$.OEt$_2$ (30.2 µL, 35.6 mg, 0.22 mmol, 1.1 equiv.), reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL). After 2 h of reaction, another batch of PhI=NTces (86.1 mg, 0.20 mmol, 1.0 equiv.) was quickly added to the reaction mixture. The reaction was further stirred for 13 h. Following work-up, the crude material was purified by flash chromatography (50 mL silica, gradient elution 20%→40%→60%→80% EtOAc/hexanes (2 column volumes each)) to afford the product as a white solid with green discoloration as a mixture of diastereomers.

Run 1 (38.4 mg, 0.088 mmol, 44% yield, 1:1 d.r.; 0.8 mg, 0.004 mmol, 2% rsm).

Run 2 (35.6 mg, 0.082 mmol, 41% yield, 1:1 d.r.; 6.7 mg, 0.032 mmol, 16% rsm).

Run 3 (35.6 mg, 0.082 mmol, 41% yield, 1:1 d.r.; 2.9 mg, 0.014 mmol, 7% rsm).

Average overall yield: 42% (8% rsm)+1.7, (1:1 d.r.).

$^1$H NMR (400 MHz, CDCl$_3$) (mixture of diastereomers): δ 8.34 (m, 2H), 7.63 (dd, J=7.7, 3.9 Hz, 1H), 7.30 (td, J=7.6, 3.5 Hz, 1H), 7.24-7.18 (m, 1H), 6.94 (m, 2H), 6.82 (m, 1H), 6.65 (d, J=7.7 Hz, 0.5H), 6.02 (d, J=7.8 Hz, 0.5H), 4.93-4.83 (m, 1H), 4.71 (s, 1H), 4.69 (s, 1H), 4.16 (t, J=6.1 Hz, 0.5H), 4.05 (d, J=6.0 Hz, 0.5H), 2.39-2.28 (m, 0.5H), 2.24-2.07 (m, 2H), 2.07-1.94 (m, 1H), 1.88 (dt, J=13.7, 7.0 Hz, 0.5H).

$^{13}$C NMR (101 MHz, CDCl$_3$) (mixture of diastereomers): δ 156.21, 155.88, 149.07, 148.85, 137.81, 137.51, 135.73, 135.55, 130.39, 130.10, 129.85, 129.36, 128.63, 127.86, 127.78, 124.44, 124.25, 93.81, 93.77, 78.07, 78.02, 60.57, 53.15, 44.79, 44.12, 28.41, 28.31, 28.04, 27.47

HRMS (ESI-TOF MS ES+): m/z calculated for C$_{17}$H$_{18}$Cl$_3$N$_2$O$_3$S [M+H]$^+$: 435.0104, found 435.0104.

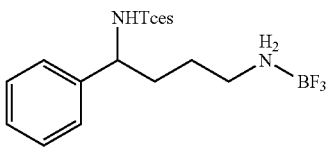

2,2,2-trichloroethyl (4-amino-1-phenylbutyl)sulfamate boron trifluoride complex [30]

Prepared according to the general amination procedure B. 4-phenylbutan-1-amine boron trifluoride complex S27 (43.4 mg, 0.20 mmol, 1.0 equiv.) was reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 5 Å molecular sieves (40 mg) in DCE (0.4 mL) for 15 h. The crude material was purified by flash chromatography (50 mL silica, gradient elution CH$_2$Cl$_2$ (12 column volumes) →10%→20%→30%→40% EtOAc/Hex (4 column volumes each)), staining with ninhydrin to afford the product as a white solid with slight discoloration.

Run 1 (48.7 mg, 0.11 mmol, 55% yield; 11.4 mg, 0.053 mmol, 26% rsm).

Run 2 (54.4 mg, 0.12 mmol, 61% yield; 11.3 mg, 0.052 mmol, 26% rsm).

Run 3 (46.9 mg, 0.11 mmol, 53% yield; 12.8 mg, 0.059 mmol, 30% rsm).

Average overall yield: 56% (27% rsm)+4.1.

$^1$H NMR (500 MHz, CD$_3$CN): δ 7.43-7.35 (m, 4H), 7.35-7.29 (m, 1H), 6.64 (d, J=8.4 Hz, 1H), 4.57 (br s, 2H), 4.44 (q, J=8.2 Hz, 1H), 4.39 (d, J=11.0 Hz, 1H), 4.20 (d, J=11.0 Hz, 1H), 2.76 (p, J=7.1 Hz, 2H), 1.93-1.86 (m, 1H), 1.83-1.75 (m, 1H), 1.75-1.65 (m, 1H), 1.58-1.47 (m, 1H).

$^{13}$C NMR (101 MHz, CD$_3$CN): δ 142.19, 129.69, 128.86, 127.65, 94.22, 78.48, 59.76, 41.21, 34.61, 25.88.

$^{19}$F NMR (470 MHz, CD$_3$CN): δ −151.91 (dd, J=32.4, 15.9 Hz, 3F)

HRMS (ESI-TOF MS ES−): m/z calculated for C$_{12}$H$_{16}$BCl$_3$F$_3$N$_2$O$_3$S [M−H]$^+$: 440.9992, found 440.9984.

Example 5. Experimental Procedures and Compound Characterization for Scheme 2

General Procedures:

In Scheme 2 the general procedure B for benzylic amination was followed for non-basic nitrogen containing substrates and the general procedure C for benzylic amination was followed for substrates containing basic nitrogen functionality.

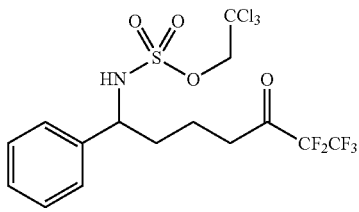

2,2,2-trichloroethyl (6,6,7,7,7-pentafluoro-5-oxo-1-phenylheptyl)sulfamate [31]

According to the general amination procedure B, 5 Å powdered molecular sieves (40 mg), 1,1,1,2,2-pentafluoro-7-phenylheptan-3-one S28 (56.0 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was dry loaded onto a silica gel column. Flash chromatography using gradient elution (100 mL of 100% hexanes then 300 mL of 5% ethyl acetate in 95% hexanes followed by 600 mL of 10% ethyl acetate in 90% hexanes) gave the pure product as a yellow solid.

Run 1 (53 mg, 0.105 mmol, 52% yield).

Run 2 (53 mg, 0.105 mmol, 52% yield).

Run 3 (50 mg, 0.099 mmol, 49% yield).

Average overall yield: 51% yield+1.7.

$^1$H NMR (500 MHz, Chloroform-d): δ 7.39 (dd, J=8.1, 6.5 Hz, 2H), 7.37-7.33 (m, 1H), 7.32-7.28 (m, 2H), 5.16 (d, J=7.7 Hz, 1H), 4.51 (q, J=7.4 Hz, 1H), 4.36 (d, J=10.8 Hz, 1H), 4.30 (d, J=10.8 Hz, 1H), 2.78 (t, J=6.9 Hz, 2H), 2.05-1.94 (m, 1H), 1.93-1.83 (m, 1H), 1.83-1.72 (m, 1H), 1.69-1.55 (m, 1H).

$^{13}$C NMR (126 MHz, CDCl$_3$): δ 194.0 (t, J=26.7 Hz), 139.9, 129.3, 128.7, 126.7, 117.9 (qt, J=286.6, 34.0 Hz), 106.9 (tq, J=266.8, 37.9 Hz), 93.3, 78.2, 59.3, 36.7, 35.6, 19.0.

$^{19}$F NMR (470 MHz, Chloroform-d): δ −82.33, −123.79.

HRMS (ESI-TOF MS ES−): m/z calculated for C$_{15}$H$_{14}$NO$_4$SCl$_3$ [M−H]$^-$: 503.9629, found 503.9612.

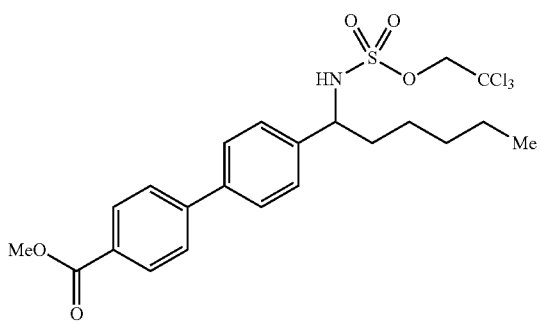

Methyl 4'-(1-(((2,2,2-trichloroethoxy)sulfonyl)amino)hexyl)-[1,1'-biphenyl]-4-carboxylate [32]

According to the general amination procedure B, 5 Å powdered molecular sieves (40 mg), methyl 4'-hexyl-[1,1'-biphenyl]-4-carboxylate S29 (59.3 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)[3]-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was dry loaded onto a silica gel column. Flash chromatography using gradient elution (100 mL of 100% hexanes then 300 mL of 5% ethyl acetate in 95% hexanes followed by 600 mL of 10% ethyl acetate in 90% hexanes) gave the pure product as a white solid.

Run 1 (82 mg, 0.157 mmol, 78% yield).
Run 2 (83 mg, 0.159 mmol, 79% yield).
Run 3 (75 mg, 0.143 mmol, 72% yield).
Average overall yield: 76% yield+3.8.

$^1$H NMR (500 MHz, Chloroform-d): δ 8.10 (d, J=7.8 Hz, 2H), 7.61 (dd, J=8.1, 6.0 Hz, 4H), 7.41 (d, J=7.8 Hz, 2H), 5.61 (d, J=7.4 Hz, 1H), 4.55 (q, J=7.3 Hz, 1H), 4.37 (d, J=10.8 Hz, 1H), 4.33 (d, J=10.8 Hz, 1H), 3.94 (s, 3H), 2.04-1.90 (m, 1H), 1.90-1.79 (m, 1H), 1.46-1.34 (m, 1H), 1.34-1.23 (m, 5H), 0.87 (d, J=7.4 Hz, 3H).

$^{13}$C NMR (126 MHz, CDCl$_3$): δ 167.2, 145.0, 140.9, 139.9, 130.3, 129.1, 127.9, 127.4, 127.1, 93.4, 78.1, 59.4, 52.4, 37.0, 31.4, 25.8, 22.5, 14.1.

HRMS (ESI-TOF MS ES+): m/z calculated for C$_{22}$H$_{27}$NO$_5$SCl$_3$ [M+H]$^+$: 522.0676, found 522.0668.

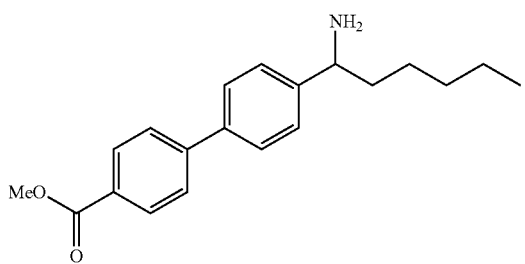 [SMILES: CCCCCC(N)c1ccc(-c2ccc(C(=O)OC)cc2)cc1]

Methyl 4'-(1-aminohexyl)-[1,1'-biphenyl]-4-carboxylate [33]

The reaction was performed according to a previously reported procedure above. In a 50 mL round bottom flask under N$_2$ containing a Teflon stir bar was added methyl 4'-(1-(((2,2,2-trichloroethoxy)sulfonyl)amino)hexyl)-[1,1'-biphenyl]-4-carboxylate 32 (205 mg, 0.39 mmol, 1 equiv), Zn/Cu couple (256 mg, 3.92 mmol, 10 equiv), and 1:1 MeOH:AcOH (12 mL). The reaction was vigorously stirred for 48 h then filtered through celite, using methanol to rinse the filter cake and concentrated. To the resulting solid was added methanolic HCl (prepared from mixing 1.22 mL acetyl chloride and 16 mL of MeOH) and the reaction heated to 40° C. for 12 h under N$_2$. Upon reaction completion, 50 mL of EtOAc was added at room temperature and the solution was washed with K$_2$CO$_3$ (1×15 mL). Additional EtOAc (2×50 mL) was used to extract the resulting aqueous layer. The organic layers were combined and dried over K$_2$CO$_3$, filtered, and concentrated. No further purification was necessary for the resulting white solid (108 mg, 88% yield).

$^1$H NMR (400 MHz, Chloroform-d): δ 8.09 (d, J=8.3 Hz, 2H), 7.63 (d, J=8.6 Hz, 2H), 7.58 (d, J=8.2 Hz, 2H), 7.40 (d, J=8.2 Hz, 2H), 3.97-3.91 (m, 4H), 2.74 (br s, 2H), 1.80-1.63 (m, 2H), 1.38-1.14 (m, 6H), 0.85 (t, J=6.7 Hz, 3H).

$^{13}$C NMR (101 MHz, CDCl$_3$): δ 167.0, 145.7, 145.3, 138.7, 130.1, 128.8, 127.4, 127.1, 126.9, 56.0, 52.2, 39.1, 31.8, 26.2, 22.6, 14.1.

HRMS (ESI-TOF MS ES+): m/z calculated for C$_{20}$H$_{26}$NO$_2$ [M+H]$^+$: 312.1964, found 312.1964.

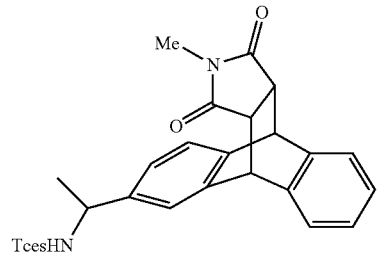

rac-2,2,2-trichloroethyl (1-((9S,10R,11R,15S)-13-methyl-12,14-dioxo-9,10-dihydro-9,10-[3,4]epipyrroloanthracen-2-yl)ethyl)sulfamate [34]

Prepared according to the general amination procedure B. rac-(9S,10R,11R,15S)-2-ethyl-13-methyl-9,10-dihydro-9,10-[3,4]epipyrroloanthracene-12,14-dione S30 (63.5 mg, 0.20 mmol, 1.0 equiv.) was reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 5 Å molecular sieves (40 mg) in benzene (0.4 mL) for 10 h. The crude reaction mixture was directly purified by flash chromatography (50 mL silica, 20%→30%→40%→50% EtOAc/Hex (2 column volumes each)) to afford the product as a white solid with slight discoloration as a mixture of diastereomers.

Run 1 (84.8 mg, 0.156 mmol, 78% yield, 1:1 d.r.).
Run 2 (95.8 mg, 0.176 mmol, 88% yield, 1:1 d.r.).
Run 3 (93.7 mg, 0.172 mmol, 86% yield, 1:1 d.r.).
Average overall yield: 84% yield+5.3, (1:1 d.r.).

¹H NMR (500 MHz, CDCl₃): δ 7.39-7.33 (m, 2H), 7.30-7.23 (m, 2H), 7.18 (dd, J=5.3, 3.2 Hz, 2H), 7.13 (d, J=7.6 Hz, 1H), 5.15 (br s, 1H), 4.82-4.74 (m, 2H), 4.65 (app dq, J=14.2, 7.0 Hz, 1H), 4.45-4.35 (m, 2H), 3.20 (app s, 2H), 2.50 (s, 3H), 1.54 (app t, J=6.4 Hz, 3H)

¹³C NMR (126 MHz, CDCl₃): δ 177.16, 177.08, 176.99, 176.98, 141.13, 141.10, 141.08, 141.06, 140.83, 140.75, 139.46, 138.76, 138.64, 127.03, 127.02, 126.99, 126.98, 125.41, 125.37, 125.33, 124.85, 124.47, 124.44, 124.42, 123.25, 122.30, 93.39, 93.36, 78.11, 54.72, 54.69, 46.99, 46.95, 45.73, 45.65, 45.29, 24.46, 24.43, 23.43, 22.98.

HRMS (ESI-TOF MS ES+): m/z calculated for C₂₃H₂₁Cl₃N₂O₅SNa [M+Na]⁺: 565.0134, found 565.0135.

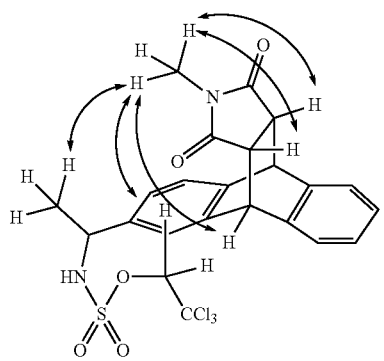

For NOESY Stereochemistry was assigned based on ¹H NMR and NOESY 1D NMR methods.

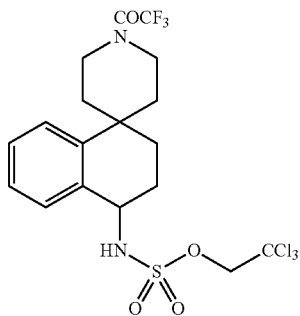

2,2,2-trichloroethyl (1'-(2,2,2-trifluoroacetyl)-3,4-dihydro-2H-spiro[naphthalene-1,4'-piperidin]-4-yl)sulfamate [35]

According to the general amination procedure B, 5 Å powdered molecular sieves (40 mg), 1-(3,4-dihydro-2H-spiro[naphthalene-1,4'-piperidin]-1'-yl)-2,2,2-trifluoroethan-1-one S31 (59.5 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-)λ³-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as a light yellow solid.

Run 1 (87 mg, 0.166 mmol, 83% yield).
Run 2 (89 mg, 0.170 mmol, 85% yield).
Run 3 (92 mg, 0.176 mmol, 88% yield).
Average overall yield: 85% yield+2.5.

¹H NMR (500 MHz, Chloroform-d): δ 7.48 (dd, J=7.7, 3.5 Hz, 1H), 7.37-7.29 (m, 2H), 7.27-7.23 (m, 1H), 5.26 (d, J=7.4 Hz, 0.5H), 5.22 (d, J=7.4 Hz, 0.5H), 4.78-4.73 (m, 1H), 4.67 (app s, 2H), 4.46 (app t, J=14.8 Hz, 1H), 3.95 (t, J=16.0 Hz, 1H), 3.41 (app q, J=11.9 Hz, 1H), 3.00 (q, J=11.7 Hz, 1H), 2.18-1.98 (m, 5H), 1.99-1.87 (m, 1H), 1.70 (d, J=13.8 Hz, 2H).

¹³C NMR (101 MHz, CDCl₃): δ 155.7 (q, J=35.7 Hz), 143.7, 134.4, 134.3, 129.4, 129.3, 129.2, 129.1, 127.3, 127.1, 116.7 (q, J=287.9 Hz), 93.7, 78.1, 53.9, 53.8, 42.2, 39.9, 39.8, 38.7, 37.6, 37.6, 36.5, 35.6, 25.9, 25.8, 25.7.

¹⁹F NMR (470 MHz, Chloroform-d): δ −69.20 (d, J=7.6 Hz).

HRMS (ESI-TOF MS ES−): m/z calculated for C₁₈H₁₉N₂O₄SCl₃F₃ [M−H]⁻: 521.0083, found 521.0079.

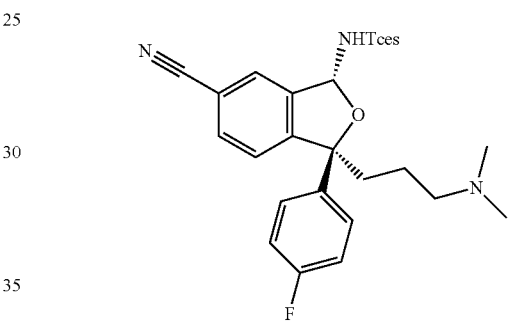

trans-2,2,2-trichloroethyl (6-cyano-3-(3-(dimethylamino)propyl)-3-(4-fluorophenyl)-1,3-dihydroisobenzofuran-1-yl)sulfamate [(±)36]

According to the general amination procedure C, 1-(3-(dimethylamino)propyl)-1-(4-fluorophenyl)-1,3-dihydroisobenzofuran-5-carbonitrile (±)S32 (64.9 mg, 0.20 mmol, 1.0 equiv.) in CH₂Cl₂ (1.2 mL) was protonated with HBF₄·OEt₂ (30.2 μL, 35.6 mg, 0.22 mmol, 1.1 equiv.), reacted with manganese (III) perchlorophthalocyanine chloride (23.1 mg, 0.020 mmol, 0.10 equiv.), AgSbF₆ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL) for 15 h. Upon reaction completion, the reaction mixture was partitioned between 1M NaOH (3 mL) and CH₂Cl₂ (3 mL). The aqueous layer was extracted with CH₂Cl₂ (3×5 mL). The organic layers were combined, dried over anhydrous MgSO₄, condensed in vacuo, and purified by flash chromatography (50 mL basic Al₂O₃ Brockmann grade III, gradient elution 30% EtOAc/Hex (4 column volumes)→0%→1%→2%→3% MeOH/CH₂Cl₂ (2 column volumes each)). The resulting solid was re-dissolved in acetonitrile, and the undissolved green solid was removed. The solution was concentrated via rotary evaporation. The resulting oil was re-dissolved in CH₂Cl₂ and concentrated via rotary evaporation to afford the product as a white solid with slight discoloration. The relative configuration was determined by NOESY and crystallography data.

Run 1 (77.7 mg, 0.141 mmol, 71% yield, >20:1 d.r.).
Run 2 (78.2 mg, 0.142 mmol, 71% yield, >20:1 d.r.).
Run 3 (77.2 mg, 0.140 mmol, 70% yield, >20:1 d.r.).
Average overall yield: 71% (0% rsm)±0.6, (>20:1 d.r.).

¹H NMR (500 MHz, CDCl₃): δ 11.89 (br s, 1H), 8.00 (s, 1H), 7.56-7.47 (m, 3H), 7.14 (d, J=7.6 Hz, 1H), 7.07 (t, J=8.6 Hz, 2H), 6.73 (s, 1H), 4.66 (d, J=10.9 Hz, 1H), 4.53 (d, J=10.9 Hz, 1H), 3.28 (dt, J=11.4, 5.9 Hz, 1H), 2.71 (s, 6H), 2.65-2.59 (m, 1H), 2.48-2.39 (m, 1H), 2.38-2.29 (m, 1H), 1.85-1.66 (m, 2H).

¹³C NMR (126 MHz, CDCl₃): δ 162.40 (d, J=247.4 Hz), 149.62, 142.09, 137.49, 132.63, 128.17, 126.99 (d, J=8.1 Hz), 121.83, 118.56, 115.94 (d, J=21.3 Hz), 112.48, 95.32, 90.96, 90.19, 77.78, 57.00, 42.88, 37.08, 20.67.

¹⁹F NMR (470 MHz, CDCl₃): δ -114.82 (s, 1F).

HRMS (ESI-TOF MS ES+): m/z calculated for C₂₂H₂₄Cl₃N₃O₄FS [M+H]⁺: 550.0537, found 550.0537.

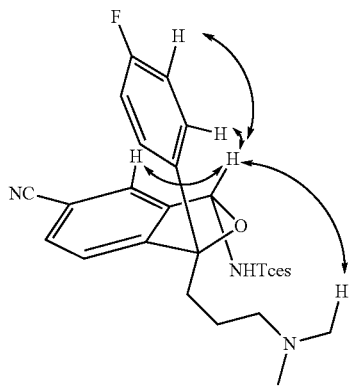

For COSY and NOESY Stereochemistry was assigned based on ¹H NMR and NOESY 1D NMR methods.

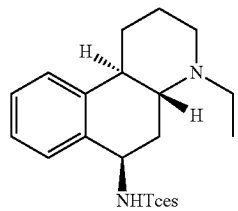

2,2,2-trichloroethyl (trans-4-ethyl-1,2,3,4,4a,5,6,10b-octahydrobenzo[f]quinolin-6-yl)sulfamate [(±) 37]

According to the general procedure C, trans-4-ethyl-1,2,3,4,4a,5,6,10b-octahydrobenzo[/]quinoline (±)S33 (43.1 mg, 0.20 mmol, 1.0 equiv.) was protonated with HBF₄.OEt₂ (30.2 μL, 35.6 mg, 0.22 mmol, 1.1 equiv.), reacted with manganese (III) perchlorophthalocyanine chloride (23.1 mg, 0.020 mmol, 0.10 equiv.), AgSbF₆ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL). After 2 h of reacting, another batch of PhI=NTces (86.1 mg, 0.20 mmol, 1.0 equiv.) was quickly added to the reaction mixture. The reaction was further stirred for 13 h. Following work-up, the crude material was purified by flash chromatography (50 mL basic Al₂O₃ Brockmann grade III, gradient elution 30% EtOAc/Hex (4 column volumes)→0%→1%→2%→ 3% MeOH/CH₂Cl₂ (2 column volumes each)), staining with KMnO₄ to afford the product as a white solid with green discoloration as a mixture of diastereomers. The relative configuration was determined by NOESY and crystallography data.

Run 1 (53.6 mg, 0.121 mmol, 61% yield, 5:1 d.r.).
Run 2 (53.8 mg, 0.122 mmol, 61% yield, 6:1 d.r.).
Run 3 (49.3 mg, 0.112 mmol, 56% yield, 5:1 d.r.; 4.3 mg, 0.020 mmol, 10% rsm).
Average overall yield: 59% (3% rsm)±2.9, (5:1 dr).

Data for Major Diastereomer (±)37:

¹H NMR (500 MHz, CDCl₃): δ 7.48 (dd, J=7.6, 1.2 Hz, 1H), 7.35 (d, J=7.7 Hz, 1H), 7.31 (td, J=7.7, 1.5 Hz, 1H), 7.26 (td, J=7.3, 1.1 Hz, 1H), 4.98 (dd, J=4.2, 2.7 Hz, 1H), 4.74 (d, J=10.9 Hz, 1H), 4.72 (d, J=10.9 Hz, 1H), 3.05 (dt, J=11.4, 3.0 Hz, 1H), 2.95 (dq, J=14.4, 7.2 Hz, 1H), 2.75 (dt, J=13.5, 2.3 Hz, 1H), 2.70 (dq J=14.0, 6.7 Hz, 1H), 2.60-2.49 (m, 2H), 2.36-2.25 (m, 2H), 1.92-1.86 (m, 1H), 1.86-1.78 (m, 2H), 1.37 (qd, J=12.7, 3.9 Hz, 1H), 1.08 (t, J=7.2 Hz, 3H).

¹³C NMR (101 MHz, CDCl₃): δ 139.92, 133.19, 129.69, 128.93, 127.08, 126.09, 93.72, 78.08, 57.90, 53.50, 52.36, 46.90, 42.47, 33.28, 29.18, 25.57, 9.64.

HRMS (ESI-TOF MS ES+): m/z calculated for C₁₇H₂₄Cl₃N₂O₃S [M+H]⁺: 441.0573, found 441.0567.

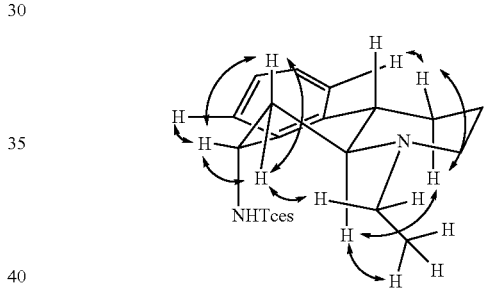

For COSY and NOESY Stereochemistry was assigned based on ¹H NMR, COSY, and NOESY 1D NMR methods.

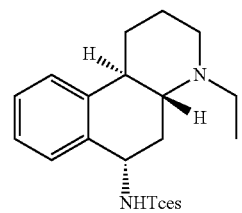

Data for Minor Diastereomer (±)S34:

¹H NMR (500 MHz, CDCl₃): δ 7.61 (d, J=6.9 Hz, 1H), 7.32 (t, J=7.1 Hz, 1H), 7.28 (d, J=6.7 Hz, 1H), 7.27-7.24 (m, 1H), 4.92 (dd, J=11.2, 6.1 Hz, 1H), 4.74 (d, J=10.8 Hz, 1H), 4.70 (d, J=10.8 Hz, 1H), 3.01 (d, J=11.5 Hz, 1H), 2.99-2.95 (m, 1H), 2.92 (dt, J=14.3, 7.1 Hz, 1H), 2.68 (dq, J=13.9, 7.3 Hz, 2H), 2.48 (dd, J=12.6, 2.6 Hz, 1H), 2.30-2.19 (m, 2H), 1.89-1.76 (m, 2H), 1.63 (q, J=11.7 Hz, 1H), 1.19 (qd, J=12.7, 4.2 Hz, 1H), 1.03 (t, J=7.1 Hz, 3H).

HRMS (ESI-TOF MS ES+): m/z calculated for C₁₇H₂₄Cl₃N₂O₃S [M+H]⁺: 441.0573, found 441.0566.

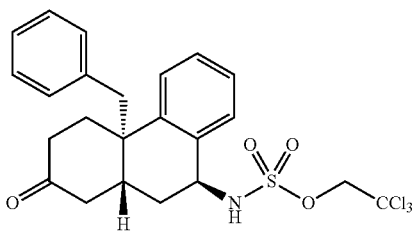

(−)2,2,2-trichloroethyl ((4aS,9S,10aR)-4a-benzyl-2-oxo-1,2,3,4,4a,9,10,10a-octahydrophenanthren-9-yl)sulfamate [38]

According to the general amination procedure B, 5 Å powdered molecular sieves (40 mg), (4aS,10aR)-4a-benzyl-3,4,4a,9,10,10a-hexahydrophenanthren-2(1H)-one (−)S35 (58.1 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and the crude brown oil was dry loaded onto a silica gel column. Flash chromatography using gradient elution (500 mL of 100% dichloromethane then 300 mL of 2% diethyl ether in 98% dichloromethane followed by 300 mL of 5% diethyl ether in 95% dicholoromethane) gave the pure product as a white solid. The relative configuration was determined by crystallography data.

Run 1 (55 mg, 0.106 mmol, 53% yield, 8:1 dr).
Run 2 (60 mg, 0.116 mmol, 58% yield, 8:1 dr).
Run 3 (60 mg, 0.116 mmol, 58% yield, 7:1 dr).
Average overall yield: 56% yield+2.9, (8:1 dr).

Data for Major Diastereomer (−)38:

$^1$H NMR (500 MHz, Chloroform-d): δ 7.52 (d, J=7.4 Hz, 1H), 7.27-7.24 (t, J=7.3 Hz, 1H), 7.21-7.16 (m, 1H), 7.15-7.08 (m, 2H), 7.00 (t, J=7.3 Hz, 1H), 6.55 (d, J=7.2 Hz, 2H), 6.44-6.39 (m, 1H), 5.37 (d, J=6.9 Hz, 1H), 4.87 (ddd, J=6.0, 5.0, 1.2 Hz, 1H), 4.68 (s, 2H), 3.14 (d, J=13.3 Hz, 1H), 2.89-2.79 (m, 1H), 2.74 (d, J=13.4 Hz, 1H), 2.67 (t, J=14.7 Hz, 1H), 2.60-2.50 (m, 2H), 2.46-2.34 (m, 2H), 2.29 (td, J=13.7, 5.4 Hz, 1H), 2.06 (dt, J=14.6, 2.0 Hz, 1H), 1.68-1.59 (m, 1H).

$^{13}$C NMR (101 MHz, CDCl$_3$): δ 210.4, 142.4, 136.7, 133.3, 130.9, 130.5, 128.0, 127.9, 127.7, 127.6, 126.8, 93.7, 78.1, 53.1, 43.8, 40.1, 38.4 38.2, 37.0, 33.7, 32.2.

HRMS (ESI-TOF MS ES+): m/z calculated for C$_{23}$H$_{24}$NO$_4$SCl$_3$Na [M+Na]$^+$: 538.0389, found 538.0379.

[α]$_D^{24}$=−92.7° (c=1.0, CHCl$_3$).

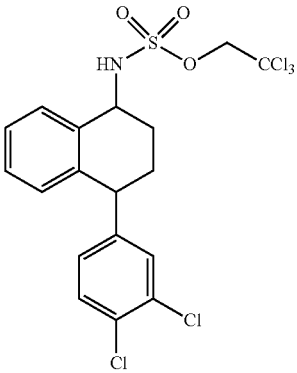

2,2,2-trichloroethyl (4-(3,4-dichlorophenyl)-1,2,3,4-tetrahydronaphthalen-1-yl)sulfamate [S36]

According to the general amination procedure B, 5 Å powdered molecular sieves (40 mg), 1-(3,4-dichlorophenyl)-1,2,3,4-tetrahydronaphthalene 39 (55.4 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was removed by rotary evaporation and the crude brown oil was dry loaded onto a silica gel column. Flash chromatography using gradient elution (400 mL of 5% ethyl acetate in hexane followed by 400 mL of 10% ethyl acetate in hexanes) gave the pure product as an off-white solid as a 1:1 mixture of separable diastereomers.

Run 1 (72.7 mg, 0.144 mmol, 72% yield).
Run 2 (74.7 mg, 0.148 mmol, 74% yield).
Run 3 (73.5 mg, 0.146 mmol, 73% yield).
Average overall yield: 73% yield+1.0 (1:1 d.r.).

Characterized as Two Diastereomers:
D1 (Syn):

$^1$H NMR (500 MHz, CDCl$_3$): δ 7.44 (d, J=7.7 Hz, 1H), 7.21 (d, J=8.2 Hz, 1H), 7.11 (t, J=7.5 Hz, 1H), 7.07-6.99 (m, 2H), 6.65 (d, J=7.7 Hz, 1H), 6.59 (dd, J=8.0, 2.1 Hz, 1H), 4.68 (q, J=5.6 Hz, 1H), 4.55-4.47 (m, 3H), 3.58 (dd, J=8.7, 5.6 Hz, 1H), 1.99-1.91 (m, 1H), 1.78-1.69 (m, 2H), 1.65-1.54 (m, 1H).

$^{13}$C NMR (126 MHz, CDCl$_3$): δ 146.31, 139.02, 134.95, 132.74, 130.75, 130.70, 130.66, 130.28, 129.69, 128.91, 128.25, 127.71, 93.68, 78.22, 53.48, 44.79, 28.66, 28.26.

HRMS (ESI− TOF MS ES+): m/z calculated for C$_{18}$H$_{16}$Cl$_5$NO$_3$SNa [M+Na]$^+$: 523.9191, found 523.9200.

D2 (Anti):

$^1$H NMR (500 MHz, CDCl$_3$): δ 7.61 (d, J=7.0 Hz, 1H), 7.34 (d, J=8.3 Hz, 1H), 7.30 (td, J=7.9, 1.5 Hz, 1H), 7.21 (td, J=7.4, 1.4 Hz, 1H), 7.10 (d, J=2.1 Hz, 1H), 6.87 (d, J=7.7 Hz, 1H), 6.83 (dd, J=8.2, 2.1 Hz, 1H), 4.93-4.89 (m, 2H), 4.71 (s, 2H), 4.15 (t, J=6.0 Hz, 1H), 2.35-2.20 (m, 2H), 2.05-1.95 (m, 1H), 1.87 (dddd, J=12.9, 8.3, 6.5, 2.0 Hz, 1H).

$^{13}$C NMR (126 MHz, CDCl$_3$): δ 146.34, 138.60, 135.31, 132.63, 130.65, 130.59, 130.53, 128.99, 128.80, 128.47, 128.12, 127.82, 93.69, 78.26, 53.66, 44.04, 29.06, 27.78.

HRMS (ESI-TOF MS ES+): m/z calculated for C$_{18}$H$_{16}$Cl$_5$NO$_3$S [M+NaCl]$^+$: 558.3 found 557.9.

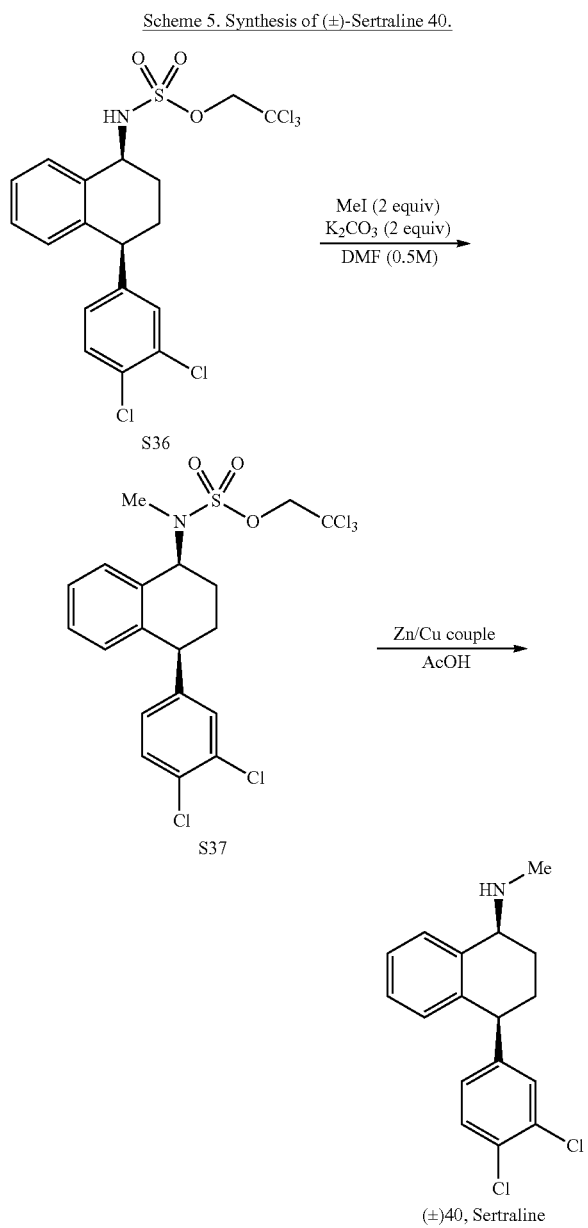

Scheme 5. Synthesis of (±)-Sertraline 40.

Part 1:

The aminated product S36 was weighed out in a vial and added to a flame dried round bottom under argon (68.7 mg, 0.14 mmol) along with DMF (0.3 mL, 0.5M) and K$_2$CO$_3$ (37.6 mg, 0.27 mmol, 2 equiv.) and the reaction was stirred at room temperature for 5 minutes. The reaction was cooled to 0° C. and MeI (29.1 mg, 0.205 mmol, 1.5 equiv.) was added dropwise. The reaction was brought to room temperature and stirred for 2 h (monitored by TLC). Upon reaction completion, water (10 mL) and DCM (10 mL) was added to the round bottom. The phases were separated and the aqueous layer was extracted with DCM (2×20 mL). The combined organic layers were washed with water (2×20 mL), dried over Na$_2$SO$_4$, filtered and concentrated using rotary evaporation to give the crude product S37 in quantitative yield. This was carried directly to the next step without further purification.

Part 2:

The reaction was performed according to a previously reported procedure above. In a 25 mL round bottom flask under N$_2$ containing a Teflon stir bar was added rac-2,2,2-trichloroethyl ((1S,4S)-4-(3,4-dichlorophenyl)-1,2,3,4-tetra-hydronaphthalen-1-yl)sulfamate S37 (70.5 mg, 0.136 mmol, 1 equiv), Zn/Cu couple (96 mg, 1.36 mmol, 10 equiv), and 1:1 MeOH:AcOH (4.3 mL). The reaction was vigorously stirred for 48 h then filtered through celite, using methanol to rinse the filter cake and concentrated using rotary evaporation. To the resulting solid was added methanolic HCl (prepared from mixing 0.41 mL acetyl chloride and 5.4 mL of MeOH) and the reaction heated to 40° C. for 12 h under N$_2$. Upon reaction completion, 20 mL of EtOAc was added at room temperature and the solution was washed with K$_2$CO$_3$ (1×10 mL). Additional EtOAc (2×20 mL) was used to extract the resulting aqueous layer. The organic layers were combined and dried over K$_2$CO$_3$, filtered, and concentrated. Silica gel flash chromatography using gradient elution (0-10% methanol in dichloromethane) gave the pure product 40 as a white solid (39.5 mg, 0.129 mmol, 95% yield).

Characterization Matched the Reported Characterization for the (±)-Syn-Diastereomer.

$^1$H NMR (500 MHz, CDCl$_3$): δ 7.43-7.40 (m, 1H), 7.35 (d, J=8.2 Hz, 1H), 7.28 (d, J=2.1 Hz, 1H), 7.21 (t, J=7.4 Hz, 1H), 7.13 (td, J=7.5, 1.4 Hz, 1H), 7.00 (dd, J=8.3, 2.1 Hz, 1H), 6.81 (d, J=7.8 Hz, 1H), 3.99 (dd, J=9.3, 5.5 Hz, 1H), 3.83 (t, J=4.3 Hz, 1H), 3.35 (br s, 1H), 2.55 (s, 3H), 2.17-1.96 (m, 3H), 1.93-1.82 (m, 1H).

$^{13}$C NMR (126 MHz, CDCl$_3$): δ 147.21, 139.01, 137.90, 132.43, 130.89, 130.48, 130.29, 130.06, 129.50, 128.45, 127.79, 126.88, 57.29, 45.43, 33.73, 28.43, 25.36.

HRMS (ESI-TOF MS ES+): m/z calculated for C$_{17}$H$_{18}$NCl$_2$ [M+H]$^+$: 306.0816, found 306.0817.

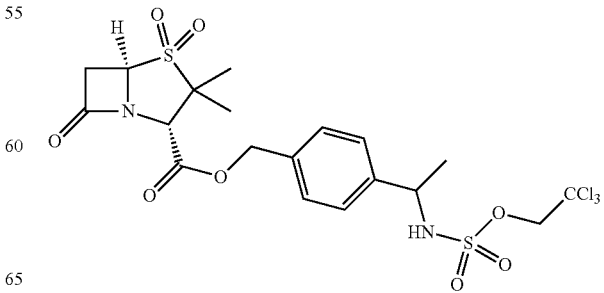

4-(1-(((2,2,2-trichloroethoxy)sulfonyl)amino)ethyl) benzyl (2S,5R)-3,3-dimethyl-7-oxo-4-thia-1-azabicyclo[3.2.0]heptane-2-carboxylate 4,4-dioxide [41]

According to the general amination procedure B, 5 Å powdered molecular sieves (40 mg), 4-ethylbenzyl (2S,5R)-3,3-dimethyl-7-oxo-4-thia-1-azabicyclo[3.2.0]heptane-2-carboxylate 4,4-dioxide S38 (70.3 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was removed by rotary evaporation and the crude brown oil was dry loaded onto a silica gel column. Flash chromatography on 75 mL silica using gradient elution (400 mL of 20% ethyl acetate in hexane followed by 400 mL of 40% ethyl acetate in hexanes) gave the pure product as a yellow oil in an equal mixture of diastereomers.

Run 1 (57.8 mg, 0.100 mmol, 50% yield).
Run 2 (56.6 mg, 0.098 mmol, 49% yield).
Run 3 (59.0 mg, 0.102 mmol, 51% yield).
Average overall yield: 50% yield±1.0 (1:1 d.r.).
$^1$H NMR (500 MHz, CDCl$_3$): δ 7.41-7.33 (m, 4H), 5.27 (br s, 1H), 5.22 (d, J=12.2 Hz, 1H), 5.18 (d, J=12.1 Hz, 1H), 4.74 (p, J=7.0 Hz, 1H), 4.63-4.58 (m, 1H), 4.48 (d, J=10.9 Hz, 1H), 4.45 (d, J=10.9 Hz, 1H), 4.41 (s, 1H), 3.52-3.40 (m, 2H), 1.61 (d, J=6.8 Hz, 3H), 1.56 (s, 3H), 1.32 (s, 3H).
$^{13}$C NMR (126 MHz, CDCl$_3$): δ 171.05, 166.98, 142.61, 134.34, 129.42, 126.87, 93.42, 78.17, 67.79, 63.29, 62.90, 61.21, 54.59, 38.42, 23.07, 20.31, 18.72.
HRMS (ESI-TOF MS ES+): m/z calculated for C$_{19}$H$_{24}$Cl$_3$N$_2$O$_8$S$_2$ [M+H]$^+$: 577.0015, found 577.0040.

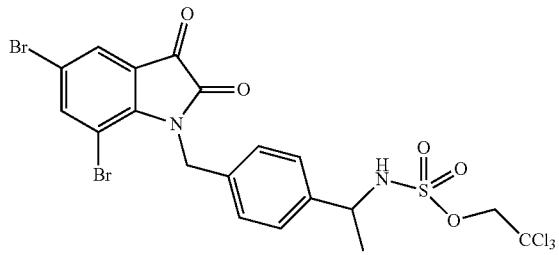

2,2,2-trichloroethyl (1-(4-((5,7-dibromo-2,3-dioxoindolin-1 yl)methyl)phenyl)ethyl) sulfamate [42]

According to the general procedure B, 5 Å powdered molecular sieves (40 mg), 5,7-dibromo-1-(4-ethylbenzyl) indoline-2,3-dione S39 (84.6 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was removed by rotary evaporation and the crude brown oil was dry loaded onto a silica gel column. Flash chromatography on 75 mL silica using gradient elution (200 mL of 10% ethyl acetate in hexane followed by 400 mL of 20% ethyl acetate in hexanes, then 400 mL of 40% ethyl acetate in hexanes) gave the pure product as an orange solid.

Run 1 (84.4 mg, 0.130 mmol, 65% yield).
Run 2 (81.8 mg, 0.126 mmol, 63% yield).
Run 3 (81.8 mg, 0.126 mmol, 63% yield).
Average overall yield: 64% yield+1.2.
$^1$H NMR (500 MHz, CDCl$_3$): δ 7.82 (d, J=2.0 Hz, 1H), 7.72 (d, J=2.0 Hz, 1H), 7.34 (d, J=8.0 Hz, 2H), 7.26 (d, J=8.0 Hz, 2H), 5.40 (s, 2H), 5.19 (br d, J=7.3 Hz, 1H), 4.71 (dq, J=13.6, 7.1 Hz, 1H), 4.44 (d, J=10.9 Hz, 1H), 4.40 (d, J=11.0 Hz, 1H), 1.60 (d, J=6.8 Hz, 3H).
$^{13}$C NMR (126 MHz, CDCl$_3$): δ 181.28, 158.48, 146.62, 145.50, 141.25, 135.84, 127.80, 127.25, 126.95, 121.53, 117.50, 105.31, 93.42, 78.18, 54.57, 44.48, 23.00.
HRMS (ESI- TOF MS ES+): m/z calculated for C$_{19}$H$_{15}$N$_2$O$_5$SCl$_3$Br$_2$Na [M+Na]$^+$: 668.8032, found 668.8028.

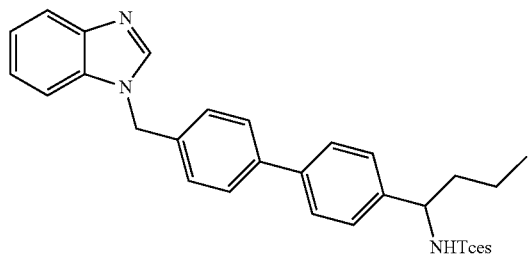

2,2,2-trichloroethyl (1-(4'-((1H-benzo[d]imidazol-1-yl)methyl)-[1,1'-biphenyl]-4-yl)butyl)sulfamate [43]

To a 1 dram vial equipped with a stir bar were added 1-((4'-butyl-[1,1'-biphenyl]-4-yl)methyl)-1H-benzo[d]imidazole S40 (68.1 mg, 0.20 mmol, 1.0 equiv.) and methylene chloride (DCM) (0.8 mL). Boron trifluoride diethyl ether complex (BF$_3$OEt$_2$) (27.2 μL, 31.2 mg, 0.22 mmol, 1.1 equiv.) was added dropwise while stirring. The reaction mixture was stirred for 1.5 h at room temperature. Upon reaction completion, the stir bar was removed, and the mixture was concentrated in vacuo and placed on vacuum overnight. The resulting white foamy solid was reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL), according to the general amination procedure A. The reaction was stirred for 15 h in 40° C. oil bath. Upon completion, the flask was taken out of oil bath. Tetramethylethylenediamine (TMEDA) (150 μL, 116 mg, 1.0 mmol, 5.0 equiv.) was added, and DCM (1 mL) was used to wash off the solid remaining on the wall. The reaction mixture was further stirred for 4 h for complete removal of the BF$_3$ protection. The resulting mixture was directly loaded onto a flash column and purified (50 mL silica, gradient elution 20%→30%→40% (4 column volumes each) →50%→60%→70% (2 column volumes each)→80% EtOAc/hexanes (6 column volumes)) to afford the product as a white solid with slight green discoloration.

Run 1 (57.9 mg, 0.102 mmol, 51% yield; 3.5 mg, 0.010 mmol, 5% rsm).
Run 2 (66.2 mg, 0.117 mmol, 58% yield; 5.4 mg, 0.016 mmol, 8% rsm).
Run 3 (57.2 mg, 0.101 mmol, 50% yield; 3.0 mg, 0.0088 mmol, 4% rsm)

Average overall yield: 53% (6% rsm)±4.4.

$^1$H NMR (500 MHz, CDCl$_3$): δ 8.00 (s, 1H), 7.85 (dd, J=6.8, 1.6 Hz, 1H), 7.53 (d, J 6.5 Hz, 2H), 7.51 (d, J=6.5 Hz, 2H), 7.37 (d, J=8.2 Hz, 2H), 7.35-7.31 (m, 1H), 7.31-7.27 (m, 2H), 7.25 (d, J=8.8 Hz, 2H), 5.54 (d, J=7.4 Hz, 1H), 5.41 (s, 2H), 4.57 (q, J=7.4 Hz, 1H), 4.37 (d, J=10.8 Hz, 1H), 4.34 (d, J=10.8 Hz, 1H), 2.02-1.92 (m, 1H), 1.90-178 (m, 1H), 1.47-1.28 (m, 2H), 0.95 (t, J=7.4 Hz, 3H).

$^{13}$C NMR (126 MHz, CDCl$_3$): δ 144.03, 143.38, 140.71, 140.35, 140.22, 134.84, 134.06, 127.82, 127.73, 127.70, 127.39, 123.35, 122.56, 120.60, 110.19, 93.45, 78.09, 59.18, 48.70, 39.13, 19.44, 13.76.

HRMS (ESI-TOF MS ES+): m/z calculated for C$_{26}$H$_{27}$N$_3$O$_3$SCl$_3$ [M+H]$^+$: 566.0839, found 566.0837.

Example 6. Experimental Procedures and Compound Characterization for Scheme 3

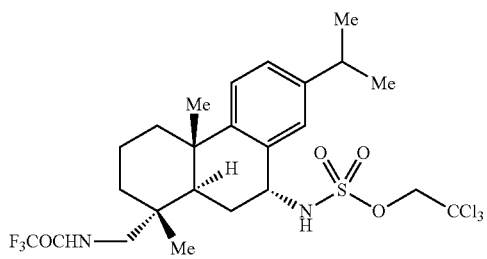

(−)2,2,2-trichloroethyl ((1R,4aS,9R,10aR)-7-isopropyl-1,4a-dimethyl-1-((2,2,2-trifluoroacetamido) methyl)-1,2,3,4,4a,9,10,10a-octahydrophenanthren-9-yl)sulfamate [(−)44]

According to the general amination procedure B, 5 Å powdered molecular sieves (40 mg), 2,2,2-trifluoro-N-(((1R,4aS,10aR)-7-isopropyl-1,4a-dimethyl-1,2,3,4,4a,9,10,10a-octahydrophenanthren-1-yl)methyl)acetamide S41 (76.3 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8-12 h. After silica plug filtration using diethyl ether as the eluent (30 mL), the solvent was concentrated and a $^1$H NMR was taken of the crude brown oil to reveal 2 amination products determined to be a mixture of diastereomers at the 2° benzylic C—H bond. The sample was dry loaded onto a silica gel column. Flash chromatography using gradient elution (100 mL of 100% hexanes then 300 mL of 5% ethyl acetate in 95% hexanes followed by 600 mL of 10% ethyl acetate in 90% hexanes) gave the diastereomeric mixture as a slightly yellow solid. The same flash chromatography conditions were used to separate the major diastereomer from the minor diastereomer. The relative configuration was determined by crystallography data.

Run 1 (73 mg, 0.120 mmol, 60% yield, 5:1 d:r).
Run 2 (78 mg, 0.128 mmol, 64% yield, 6:1 d:r).
Run 3 (76 mg, 0.125 mmol, 63% yield, 6:1 d:r).
Average overall yield: 62% yield+2.1, (6:1 d:r).

$^1$H NMR (500 MHz, CDCl$_3$): δ 7.29-7.16 (m, 3H), 6.70 (t, J=6.6 Hz, 1H), 5.13 (d, J 4.7 Hz, 1H), 4.87 (t, J=4.4 Hz, 1H), 4.78 (s, 2H), 3.41 (dd, J=14.0, 8.5 Hz, 1H), 3.17 (dd, J=13.9, 5.1 Hz, 1H), 2.87 (septet, J=6.9 Hz, 1H), 2.37-2.20 (m, 2H), 2.07-1.95 (m, 1H), 1.90-1.67 (m, 2H), 1.64 (d, J=12.7 Hz, 1H), 1.52-1.42 (m, 1H), 1.38-1.27 (m, 2H), 1.24 (d, J=6.9 Hz, 6H), 1.19 (s, 3H), 0.98 (s, 3H).

$^{13}$C NMR (101 MHz, CDCl$_3$): δ 158.2 (q, J=36.8 Hz), 147.7, 147.6, 131.5, 127.8, 127.7, 125.3, 116.1 (q, J=288.0 Hz), 93.7, 78.1, 54.6, 49.5, 40.1, 38.1, 38.0, 37.9, 35.5, 33.6, 25.9, 24.9, 24.1, 23.9, 19.0, 18.5.

$^{19}$F NMR (470 MHz, CDCl$_3$): δ −76.07.

HRMS (ESI-TOF MS ES+): m/z calculated for C$_{24}$H$_{32}$N$_2$O$_4$SCl$_3$F$_3$Na [M+Na]$^+$: 629.0998, found 629.1002.

[α]$_D^{24}$=−21.6° (c=1.0, CHCl$_3$).

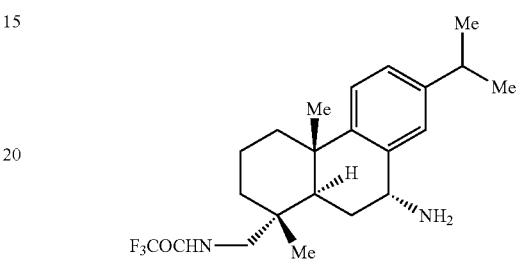

(−)-N-(((1R,4aS,9R,10aR)-9-amino-7-isopropyl-1,4a-dimethyl-1,1,2,3,4,4a,9,10,10a-octahydrophenanthren-1-yl)methyl)-2,2,2-trifluoroacetamide [(−)45]

The reaction was performed according to a previously reported procedure above. In a 50 mL round bottom flask under N$_2$ containing a Teflon stir bar was added 2,2,2-trichloroethyl ((1R,4aS,9R,10aR)-7-isopropyl-1,4a-dimethyl-1-((2,2,2-trifluoroacetamido)methyl)-1,2,3,4,4a,9,10,10a-octahydrophenanthren-9-yl)sulfamate (−)44 (42 mg, 0.069 mmol, 1 equiv), Zn/Cu couple (91 mg, 1.39 mmol, 20 equiv), and 1:1 MeOH:AcOH (4 mL). The reaction was vigorously stirred for 48 h then filtered through celite, using methanol to rinse the filter cake and concentrated using rotary evaporation. To the resulting solid was added methanolic HCl (prepared from mixing 0.44 mL acetyl chloride and 5.5 mL of MeOH) and the reaction heated to 40° C. for 12 h under N$_2$. Upon reaction completion, 20 mL of EtOAc was added at room temperature and the solution was washed with K$_2$CO$_3$ (1×10 mL). Additional EtOAc (2×20 mL) was used to extract the resulting aqueous layer. The organic layers were combined and dried over K$_2$CO$_3$, filtered, and concentrated. Silica gel flash chromatography using gradient elution (0-10% methanol in dichloromethane) gave the pure product as an oily slightly yellow solid (19 mg, 0.048 mmol, 70% yield).

$^1$H NMR (500 MHz, Chloroform-d): δ 8.63 (s, 1H), 7.19 (d, J=8.2 Hz, 1H), 7.11 (dd, J=8.2, 2.0 Hz, 1H), 7.05 (d, J=2.0 Hz, 1H), 4.31-4.19 (m, 1H), 3.64-3.52 (m, 1H), 3.00 (d, J=13.9 Hz, 1H), 2.87 (hept, J=6.8 Hz, 1H), 2.77-2.08 (m, 3H), 2.01 (d, J=11.9 Hz, 1H), 1.89-1.71 (m, 2H), 1.71-1.51 (m, 2H), 1.45-1.35 (m, 1H), 1.35-1.26 (m, 2H), 1.25 (dd, J=6.9, 1.2 Hz, 6H), 1.22 (s, 3H), 0.96 (s, 3H).

$^{13}$C NMR (126 MHz, CDCl$_3$): δ 158.1 (q, J=36.7 Hz), 147.8, 146.8, 137.2, 127.7, 126.3, 125.6, 116.4 (q, J=288.0 Hz), 49.9, 48.9, 39.6, 39.0, 38.2, 37.1, 35.3, 33.7, 28.1, 24.1, 24.0, 19.4, 18.8.

$^{19}$F NMR (471 MHz, Chloroform-d): δ −75.28.

HRMS (ESI-TOF MS ES+): m/z calculated for C$_{22}$H$_{32}$N$_2$OF$_3$ [M+H]$^+$: 397.2467, found 397.2464.

[α]$_D^{24}$=−41.3° (c=0.50, CHCl$_3$).

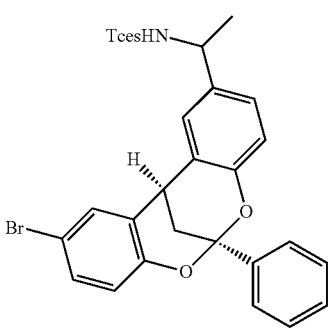

(±)-2,2,2-trichloroethyl (1-(10-bromo-6-phenyl-cis-12H-6,12-methanodibenzo[dg][1,3]dioxocin-2-yl)ethyl)sulfamate [46]

Prepared according to the general amination procedure B. 2-bromo-10-ethyl-6-phenyl-cis-12H-6,12-methanodibenzo[d,g][1,3]dioxocine (±)S42 (81.5 mg, 0.20 mmol, 1.0 equiv.) was reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 5 Å molecular sieves (40 mg) in benzene (0.4 mL) for 10 h. The crude reaction mixture was directly purified by flash chromatography (50 mL silica, 7.5% EtOAc/Hex (14 column volumes)) to afford the product as a white solid with slight discoloration as a mixture of diastereomers.

Run 1 (94.4 mg, 0.149 mmol, 75% yield, 1:1 d.r.).
Run 2 (96.9 mg, 0.153 mmol, 76% yield, 1:1 d.r.).
Run 3 (84.5 mg, 0.133 mmol, 67% yield, 1:1 d.r.).
Average overall yield: 73% yield±4.9, (1:1 d.r.).

$^1$H NMR (500 MHz, DMSO-d$_6$) (mixture of diastereomers): δ 8.89 (d, J=8.1 Hz, 0.5H), 8.87 (d, J=8.4 Hz, 0.5H), 7.73-7.66 (m, 3H), 7.55-7.42 (m, 4H), 7.30 (dt, J=8.6, 2.8 Hz, 1H), 7.27-7.19 (m, 1H), 6.99 (dd, J=8.4, 2.8 Hz, 1H), 6.95 (d, J=8.6 Hz, 1H), 4.51 (dq, J=12.4, 4.9 Hz, 1H), 4.46 (dd, J=11.1, 7.6 Hz, 1H), 4.38 (dd, J=11.1, 3.3 Hz, 0.5H), 4.34 (t, J=2.6 Hz, 0.5H), 4.31 (t, J=2.4 Hz, 0.5H), 4.23 (d, J=11.2 Hz, 0.5H), 2.44-2.38 (m, 1.5H), 2.36 (dd, J=13.6, 2.8 Hz, 0.5H), 1.47 (app t, J=7.5 Hz, 3H).

$^{13}$C NMR (126 MHz, DMSO-d$_6$) (mixture of diastereomers): δ 150.78, 150.76, 150.60, 150.53, 140.59, 136.33, 136.19, 130.56, 130.03, 129.99, 129.21, 128.92, 128.34, 128.33, 126.34, 125.96, 125.89, 125.85, 125.77, 125.54, 125.51, 118.38, 116.29, 116.20, 112.73, 112.70, 98.65, 93.74, 93.69, 77.07, 77.04, 53.29, 53.20, 32.10, 32.08, 31.47, 31.38, 23.54, 22.83.

HRMS (ESI-TOF MS ES+): m/z calculated for C$_{25}$H$_{22}$Cl$_3$BrNO$_5$S [M+H]$^+$: 631.9468, found 631.9452.

(±)-2,2,2-trichloroethyl (1-(-6-phenyl-10-(pyridin-3-yl)-cis-12H-6,12-methanodibenzo[d,g][1,3]dioxocin-2-yl)ethyl)sulfamate [47]

According to the general amination procedure C, 3-(10-ethyl-6-phenyl-cis-12H-6,12-methanodibenzo[dg][1,3]dioxocin-2-yl)pyridine (±)S43 (81.0 mg, 0.20 mmol, 1.0 equiv.) in CH$_2$Cl$_2$ (1.2 mL) was protonated with HBF$_4$OEt$_2$ (30.2 μL, 35.6 mg, 0.22 mmol, 1.1 equiv.), reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL) for 15 h. Following work-up, the crude material was purified by flash chromatography (50 mL silica, gradient elution 30%→40%→50% EtOAc/Hex (4 column volumes each)) to afford the product as a white solid with slight discoloration as a mixture of diastereomers.

Run 1 (66.0 mg, 0.104 mmol, 52% yield, 1:1 d.r.; 5.7 mg, 0.014 mmol, 7% rsm).

Run 2 (75.8 mg, 0.120 mmol, 60% yield, 1:1 d.r.; 4.1 mg, 0.010 mmol, 5% rsm).

Run 3 (76.1 mg, 0.120 mmol, 60% yield, 1:1 d.r.; 3.2 mg, 0.008 mmol, 4% rsm).

Average overall yield: 57% (5% rsm)±4.6, (1:1 d.r.).

$^1$H NMR (500 MHz, CDCl$_3$) (mixture of diastereomers): δ 8.59 (d, J=1.0 Hz, 0.5H), 8.51 (d, J=1.1 Hz, 0.5H), 8.16 (d, J=4.0 Hz, 0.5H), 8.04 (d, J=4.2 Hz, 0.5H), 7.81-7.70 (m, 2H), 7.69-7.62 (m, 1H), 7.57 (d, J=6.0 Hz, 0.5H), 7.52-7.41 (m, 3.5H), 7.38 (d, J=2.0 Hz, 0.5H), 7.37 (br s, 0.5H), 7.31 (dd, J=4.3, 2.2 Hz, 1H), 7.26-7.19 (m, 1.5H), 7.17 (dd, J=8.4, 2.2 Hz, 0.5H), 7.12 (dd, J=7.8, 4.9 Hz, 0.5H), 7.10-7.04 (m, 2.5H), 4.80-4.74 (m, 0.5H), 4.74-4.68 (m, 0.5H), 4.47 (d, J=10.8 Hz, 0.5H), 4.44 (d, J=10.8 Hz, 0.5H), 4.41 (d, J=10.8 Hz, 0.5H), 4.34 (d, J=10.8 Hz, 0.5H), 4.17 (t, J=3.1 Hz, 0.5H), 4.15 (t, J=2.7 Hz, 0.5H), 2.47-2.36 (m, 2H), 1.67 (d, J=6.9 Hz, 1.5H), 1.63 (d, J=6.8 Hz, 1.5H).

$^{13}$C NMR (126 MHz, CDCl$_3$) (mixture of diastereomers): δ 152.25, 152.20, 151.85, 151.77, 147.22, 140.92, 140.88, 135.99, 135.84, 135.11, 134.32, 134.16, 130.95, 130.85, 129.13, 128.56, 127.06, 126.90, 126.86, 126.83, 126.73, 126.69, 126.15, 126.01, 125.83, 125.79, 125.77, 125.67, 123.72, 123.66, 117.75, 117.73, 117.29, 117.18, 99.15, 99.13, 93.68, 93.66, 77.98, 77.94, 54.30, 53.99, 34.39, 33.22, 33.19, 22.75, 22.61.

HRMS (ESI-TOF MS ES+): m/z calculated for C$_{30}$H$_{26}$C$_{13}$N$_2$O$_5$S [M+H]$^+$: 631.0628, found 631.0612.

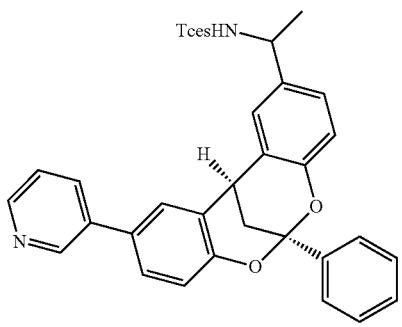

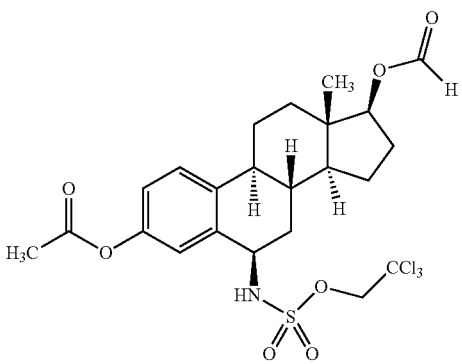

(8R,9S,13S,14S,17S)-17-(formyloxy)-13-methyl-6-(((2,2,2-trichloroethoxy)sulfonyl)amino)-7,8,9,11,12,13,14,15,16,17-decahydro-6H-cyclopenta[a]phenanthren-3-yl acetate [48]

According to the general amination procedure B, 5 Å powdered molecular sieves (40 mg), (13S,17S)-17-(formyloxy)-13-methyl-7,8,9,11,12,13,14,15,16,17-decahydro-6H-cyclopenta[a]phenanthren-3-yl acetate 48a (see page 88) (68.5 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 8-12 h. After silica plug filtration using ethyl acetate as the eluent (50 mL), the solvent was concentrated and the crude brown oil was loaded onto a silica gel column. Flash chromatography on 75 mL of silica gel using gradient elution (500 mL of 100% dichloromethane then 200 mL of 1% diethyl ether in 99% dichloromethane followed by 400 mL of 2% diethyl ether in dichloromethane) gave the pure products as colorless oils and separable diastereomers.

Run 1 (70.5 mg, 0.124 mmol, 62% yield, 1.6:1 d.r.).
Run 2 (74.0 mg, 0.130 mmol, 65% yield, 1.6:1 d.r.).
Run 3 (77.4 mg, 0.136 mmol, 68% yield, 1.6:1 d.r.).
Average overall yield: 65% yield+3.0.

$^1$H NMR (500 MHz, CDCl$_3$): δ 8.10 (s, 1H), 7.36 (d, J=8.6 Hz, 1H), 7.24 (d, J=2.2 Hz, 1H), 7.01 (dd, J=8.5, 2.3 Hz, 1H), 5.29 (br d, J=7.5 Hz, 1H), 4.82 (m, 2H), 4.71 (d, J=10.9 Hz, 1H), 4.69 (d, J=10.9 Hz, 1H), 2.39-2.22 (m, 2H), 2.30 (s, 3H), 2.23-2.15 (m, 1H), 1.95 (d, J=12.3 Hz, 1H), 1.78 (ddd, J=11.8, 9.4, 4.9 Hz, 1H), 1.72-1.32 (m, 8H), 0.89 (s, 3H).

$^{13}$C NMR (126 MHz, CDCl$_3$): δ 169.87, 161.30, 149.22, 138.29, 135.24, 127.04, 123.16, 122.16, 93.73, 82.30, 78.05, 52.81, 49.17, 43.85, 43.24, 36.68, 34.30, 33.18, 27.57, 25.76, 23.29, 21.15, 12.27.

HRMS (ESI-TOF MS ES+): m/z calculated for C$_{23}$H$_{32}$Cl$_3$N$_2$O$_7$S [M+NH$_4$]$^+$: 585.0996, found 585.0995.

Stereochemistry was assigned based on coupling constant and by analogy to compound 49.

Minor Diastereomer S44:

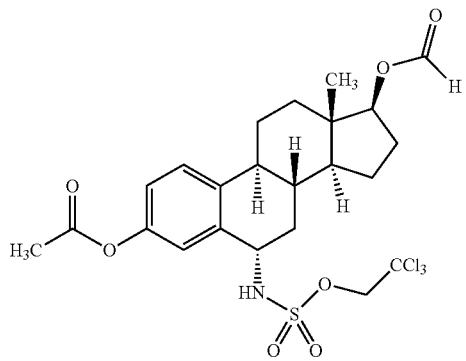

$^1$H NMR (500 MHz, CDCl$_3$): δ 8.09 (s, 1H), 7.33 (d, J=2.4 Hz, 1H), 7.30 (d, J=8.6 Hz, 1H), 6.97 (dd, J=8.6, 2.5 Hz, 1H), 5.06 (d, J=8.6 Hz, 1H), 4.87 (td, J=10.0, 7.9 Hz, 1H), 4.79 (t, J=8.5 Hz, 1H), 4.74 (d, J=10.8 Hz, 1H), 4.68 (d, J=10.9 Hz, 1H), 2.55 (ddd, J=12.5, 6.5, 2.1 Hz, 1H), 2.36-2.20 (m, 2H), 2.30 (s, 3H), 1.96-1.88 (m, 1H), 1.77-1.69 (m, 1H), 1.67-1.58 (m, 3H), 1.51-1.30 (m, 5H), 0.84 (s, 3H).

$^{13}$C NMR (126 MHz, CDCl$_3$): δ 169.89, 161.27, 149.36, 138.34, 136.48, 127.07, 121.60, 121.09, 93.75, 82.26, 78.20, 54.96, 49.24, 44.11, 43.01, 38.13, 36.71, 36.52, 27.60, 26.06, 23.34, 21.20, 12.11.

HRMS (ESI– TOF MS ES+): m/z calculated for C$_{23}$H$_{28}$NO$_7$SCl$_3$Na [M+Na]$^+$: 590.0550, found 590.0555.

Stereochemistry was assigned based on coupling constant and by analogy to compound S45.

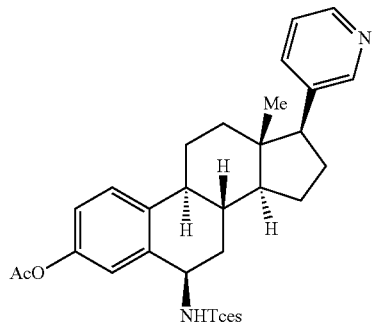

(8S,9S,13S,14S,17S)-13-methyl-17-(pyridin-3-yl)-6-(((2,2,2-trichloroethoxy)sulfonyl)amino)-7,8,9,11,12,13,14,15,16,17-decahydro-6H-cyclopenta[a]phenanthren-3-yl acetate [49]

In a 1 dram vial equipped with a stir bar were added (8S,9S,13S,14S,17S)-13-methyl-17-(pyridin-3-yl)-7,8,9,11,12,13,14,15,16,17-decahydro-6H-cyclopenta[a]phenanthren-3-yl acetate 49a (see page 88) (75.1 mg, 0.20 mmol, 1.0 equiv.) and methylene chloride (DCM) (0.8 mL). Boron trifluoride diethyl ether complex (BF$_3$OEt$_2$) (27.2 µL, 31.2 mg, 0.22 mmol, 1.1 equiv.) was added dropwise while stirring. The reaction mixture was stirred for 1.5 h at room temperature. Upon reaction completion the stir bar was taken out, and mixture was concentrated in vacuo and placed on vacuum overnight. The resulting white foamy solid was reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL), according to the general procedure A. After 2 h of reaction, another batch of PhI=NTces (86.1 mg, 0.20 mmol, 1.0 equiv.) was quickly added to the reaction mixture. The reaction was further stirred for 13 h. Upon completion, the flask was taken out of oil bath. Tetramethylethylenediamine (TMEDA) (150 µL, 116 mg, 1.0 mmol, 5.0 equiv.) was added, and DCM (1 mL) was used to wash off the solid remaining on the wall. The reaction mixture was further stirred for 4 h for complete removal of the BF$_3$ protection. The resulting mixture was directly loaded onto a flash column and purified (50 mL silica, gradient elution 20%→30%→40%→50%→70% EtOAc/hexanes (2 column volumes each)), staining with CAM to afford the product as a white solid with slight green discoloration as a mixture of diastereomers.

Run 1 (61.0 mg, 0.101 mmol, 51% yield, 1.8:1 d.r.).
Run 2 (62.7 mg, 0.104 mmol, 52% yield, 1.5:1 d.r.).
Run 3 (60.2 mg, 0.100 mmol, 50% yield, 1.4:1 d.r.).
Average overall yield: 51% (0% rsm)±1.0, (1.6:1 d.r.).

Data for Major Diastereomer 49:

$^1$H NMR (500 MHz, CDCl$_3$): δ 8.34 (br s, 1H), 8.16 (br s, 1H), 7.55 (d, J=8.2 Hz, 1H), 7.33 (d, J=8.7 Hz, 1H), 7.27 (d, J=2.6 Hz, 1H), 7.23 (dd, J=8.5, 5.0 Hz, 1H), 7.01 (dd, J=8.6, 2.5 Hz, 1H), 6.94 (br s, 1H), 4.84 (t, J=4.9 Hz, 1H), 4.71-4.66 (m, 2H), 2.72 (t, J=9.8 Hz, 1H), 2.36-2.30 (m, 2H), 2.28 (s, 3H), 2.26-2.18 (m, 1H), 2.13-1.97 (m, 2H), 1.97-1.88 (m, 1H), 1.70 (td, J=12.9, 4.7 Hz, 1H), 1.63-1.54 (m, 2H), 1.54-1.47 (m, 1H), 1.43 (td, J=13.1, 4.0 Hz, 1H), 1.32 (qd, J=14.0, 2.3 Hz, 1H), 0.37 (s, 3H).

$^{13}$C NMR (126 MHz, CDCl$_3$): δ 169.79, 149.60, 149.27, 146.93, 138.44, 136.53, 136.31, 135.76, 126.94, 123.30, 123.17, 121.99, 93.90, 78.00, 54.43, 54.38, 52.83, 44.86, 44.02, 37.44, 35.05, 33.83, 25.99, 25.86, 24.22, 21.17, 12.76.

HRMS (ESI-TOF MS ES+): m/z calculated for C$_{27}$H$_{32}$Cl$_3$N$_2$O$_5$S [M+H]$^+$: 601.1098, found 601.1110.

Stereochemistry was assigned based on coupling constant and by analogy. See below for an explanation of coupling constants and representative coupling constants for the NHTces in the axial and equatorial positions of the ring.

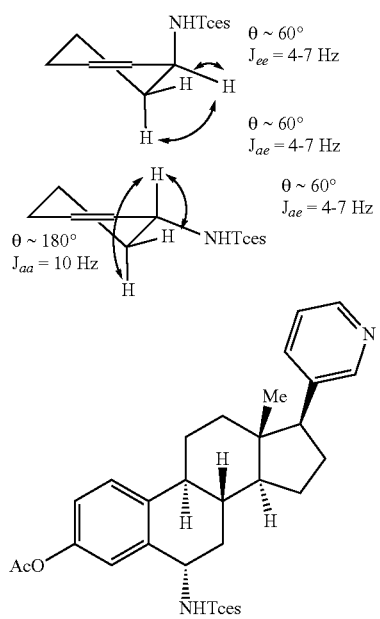

Data for Minor Diastereomer S45:

$^1$H NMR (500 MHz, CDCl$_3$): δ 8.45 (br s, 2H), 7.58 (d, J=7.9 Hz, 1H), 7.35 (d, J=1.8 Hz, 1H), 7.30 (d, J=8.6 Hz, 1H), 7.28-7.24 (m, 1H), 6.97 (dd, J=8.6, 2.5 Hz, 1H), 5.32 (d, J=9.5 Hz, 1H), 4.90 (td, J=10.2, 6.7 Hz, 1H), 4.76 (d, J=10.7 Hz, 1H), 4.71 (d, J=10.8 Hz, 1H), 2.78 (t, J=9.8 Hz, 1H), 2.63 (ddd, J=12.4, 6.5, 1.2 Hz, 1H), 2.40-2.33 (m, 1H), 2.33-2.30 (m, 1H), 2.28 (s, 3H), 2.29-2.26 (m, 1H), 2.20-1.99 (m, 2H), 1.95-1.86 (m, 1H), 1.73-1.67 (m, 1H), 1.66-1.57 (m, 1H), 1.57-1.38 (m, 4H), 0.51 (s, 3H).

$^{13}$C NMR (126 MHz, CDCl$_3$): δ 169.90, 149.83, 149.35, 147.21, 138.56, 136.58, 136.47, 136.37, 127.03, 123.24, 121.56, 121.14, 93.80, 78.21, 55.07, 54.58, 54.54, 44.72, 44.28, 38.80, 37.35, 37.14, 26.14, 26.01, 24.23, 21.21, 12.79.

HRMS (ESI-TOF MS ES+): m/z calculated for C$_{27}$H$_{32}$Cl$_3$N$_2$O$_5$S [M+H]$^+$: 601.1098, found 601.1086.

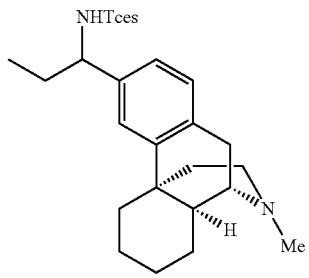

2,2,2-trichloroethyl(1-((4bS,8aS,9S)-1-methyl-6,7,8,8a,9,10-hexahydro-5H-9,4b-(epiminoethano)phenanthren-3-yl)propyl)sulfamate [50]

According to the general amination procedure C, (4bS, 8aS,9S)-11-methyl-3-propyl-6,7,8,8a,9,10-hexahydro-5H-9,4b-(epiminoethano)phenanthrene S49 (56.7 mg, 0.20 mmol, 1.0 equiv.) in CH$_2$Cl$_2$ (1.2 mL) was protonated with HBF$_4$·OEt$_2$ (30.2 µL, 35.6 mg, 0.22 mmol, 1.1 equiv.), reacted with manganese (III) perchlorophthalocyanine chloride (23.1 mg, 0.020 mmol, 0.10 equiv.), AgSbF$_6$ (6.9 mg, 0.020 mmol, 0.10 equiv.), PhI=NTces (172.2 mg, 0.40 mmol, 2.0 equiv.), and 3 Å molecular sieves (40 mg) in DCE (0.4 mL). After 2 h of reaction, another batch of PhI=NTces (86.1 mg, 0.20 mmol, 1.0 equiv.) was quickly added to the reaction mixture. The reaction was further stirred for 13 h. Following work-up, the crude material was purified by flash chromatography (50 mL basic Al$_2$O$_3$Brockmann grade III, gradient elution 40%/50% EtOAc/Hex (4 column volumes each)→0%→1%→2%→3% MeOH/CH$_2$Cl$_2$ (2 column volumes each)) to afford the product as a white solid with green discoloration as a mixture of diastereomers.

Run 1 (45.3 mg, 0.0888 mmol, 44% yield, 1:1 d.r.; 8.1 mg, 0.029 mmol, 14% rsm).

Run 2 (44.9 mg, 0.0880 mmol, 44% yield, 1.1 d.r.; 4.5 mg, 0.016 mmol, 8% rsm).

Run 3 (43.9 mg, 0.0861 mmol, 43% yield, 1:1 d.r.; 4.0 mg, 0.014 mmol, 7% rsm).

Average overall yield: 44% (10% rsm)+0.6, (1:1 d.r.).

$^1$H NMR (500 MHz, CDCl$_3$) (mixture of diastereomers): δ 7.13 (s, 1H), 7.13-7.09 (m, 1H), 7.04 (app dt, J=7.9, 1.7 Hz, 1H), 4.36 (q, J=7.9 Hz, 1H), 4.27 (d, J=10.9 Hz, 1H), 4.24 (app dd, J=10.8, 1.4 Hz, 1H), 3.01 (d, J=18.5 Hz, 1H), 2.82 (dd, J=4.8, 3.1 Hz, 1H), 2.62 (dd, J=18.5, 5.5 Hz, 1H), 2.46-2.37 (m, 2H), 2.39 (s, 3H), 2.05-1.92 (m, 2H), 1.88-1.72 (m, 3H), 1.62 (app d, J=13.2 Hz, 1H), 1.53 (app d, J=12.8 Hz, 1H), 1.45-1.25 (m, 5H), 1.24-1.14 (m, 1H), 1.12-1.00 (m, 2H), 0.90 (app td, J=7.4, 2.4 Hz, 3H).

$^{13}$C NMR (126 MHz, CDCl$_3$) (mixture of diastereomers): δ 141.14, 138.48, 138.37, 137.89, 128.57, 128.49, 124.14, 124.12, 123.63, 123.54, 93.56, 93.54, 78.25, 78.23, 61.26, 61.18, 57.98, 47.32, 45.28, 42.86, 42.83, 42.08, 37.28, 37.26, 36.57, 36.55, 30.37, 30.27, 26.79, 26.78, 26.64, 26.62, 24.25, 24.18, 22.34, 22.26, 10.85, 10.77.

HRMS (ESI-TOF MS ES+): m/z calculated for C$_{22}$H$_{32}$N$_2$O$_3$SCl$_3$ [M+H]$^+$: 509.1199, found 509.1195.

Example 7. Preparation and Characterization of Newly Reported Starting Materials General Procedure for Acetate Protection of an Alcohol.

In a flame-dried 100 mL round-bottom flask at room temperature under nitrogen was added a Teflon stir bar, the alcohol substrate (36.7 mmol, 1 equiv), pyridine (37 mL 1.2M to substrate), 4-dimethylaminopyridine (1.84 mmol, 0.05 equiv) and acetic anhydride (73.4 mmol, 2 equiv). The reaction was stirred overnight at room temperature then slowly quenched with NaHCO$_3$(sat) until bubbling ceased. The mixture was extracted with Et$_2$O (2×150 mL). The organic extracts were combined and washed with CuSO$_4$ (sat) (3×100 mL), H$_2$O (2×100 mL) then brine (1×100 mL). The organic layer was dried (anhydrous MgSO$_4$), filtered and the solvent removed using rotary evaporation. Purification of the desired compound was performed by either vacuum distillation or flash chromatography.

General Procedure for Trifluoroacetate Protection of an Amine.

In a flame-dried 200 mL round-bottom flask at 0° C. under nitrogen was added a Teflon stir bar, the amine substrate (18.79 mmol, 1 equiv), CH$_2$Cl$_2$ (47 mL, 0.4M to substrate), and pyridine (56.3 mmol, 3 equiv) followed by dropwise addition of trifluoroacetic anhydride (37.6 mmol, 2 equiv). The reaction was stirred overnight at room temperature then slowly quenched with H$_2$O, then extracted with CH$_2$Cl$_2$ (2×75 mL). The organic extracts were combined and washed with H$_2$O (2×100 mL) then brine (1×100 mL). The organic layer was dried (anhydrous Na$_2$SO$_4$), filtered and the solvent removed using rotary evaporation. Purification was of the desired compound was performed by flash chromatography.

Compounds S3, S4, S5 were obtained through commercial sources.

S6, S7. Prepared using the general procedure for acetate protection of commercial materials. The NMR data matched those reported in literature.

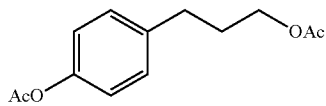 [SMILES: CC(=O)OCCCc1ccc(OC(C)=O)cc1]

3-(4-acetoxyphenyl)propyl acetate [S8]

Prepared using the general procedure for acetate protection.

$^1$H NMR (500 MHz, CDCl$_3$): δ 7.20-7.16 (m, 2H), 7.02-6.98 (m, 2H), 4.09 (t, J=6.5 Hz, 2H), 2.70-2.66 (m, 2H), 2.28 (s, 3H), 2.05 (s, 3H), 1.98-1.91 (m, 2H).

$^{13}$C NMR (126 MHz, CDCl$_3$): δ 171.24, 169.73, 149.01, 138.89, 129.41, 121.57, 63.85, 31.73, 30.27, 21.25, 21.08.

HRMS (ESI-TOF MS ES+): m/z calculated for C$_{13}$H$_{17}$O$_4$ [M+H]$^+$: 237.1116, found 237.1127.

S9. Prepared according to literatures, the NMR data matched those reported.

S10. Prepared according to the general procedure for trifluoroacetate protection of an amine and the NMR data matched those reported.

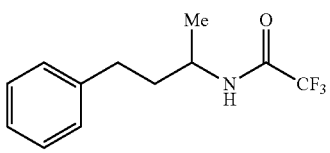 [SMILES: CC(CCc1ccccc1)NC(=O)C(F)(F)F]

2,2,2-trifluoro-N-(4-phenylbutan-2-yl)acetamide [S11]

Synthesized via trifluoroacetylation of commercially available 4-phenylbutan-2-amine. In a flame-dried round bottom flask equipped with a septum and stir bar under nitrogen was added 4-phenylbutan-2-amine (2 g, 13.4 mmol, 1 equiv.), pyridine (3.18 g, 40.2 mmol, 3 equiv.), and DCM (33 mL, 0.4 M). The reaction was cooled to 0° C. and trifluoroacetic anhydride was added dropwise (5.63 g, 26.8 mmol, 2 equiv.). The reaction was then warmed to room temperature and stirred to completion (monitored by TLC analysis). Upon completion, the reaction was quenched with H$_2$O and transferred to a separatory funnel. The mixture is extracted with DCM (2×40 mL). The organic layers were washed with H$_2$O, dried over Na$_2$SO$_4$, filtered and the solvent evaporated. The crude product is then purified using silica gel chromatography and eluted with 20% ethyl acetate in 80% hexane to give the product as a white solid (3.12 g, 12.7 mmol, 95% yield).

$^1$H NMR (500 MHz, CDCl$_3$): δ 7.32-7.27 (m, 2H), 7.23-7.16 (m, 3H), 6.02 (s, 1H), 4.08 (hept, J=13.5 Hz, 1H), 2.67 (t, J=7.8 Hz, 2H), 1.90-1.84 (m, 2H), 1.27 (d, J=6.6 Hz, 3H).

$^{13}$C NMR (126 MHz, CDCl$_3$): δ 156.63 (q, J=36.6 Hz), 140.92, 128.75, 128.39, 126.40, 115.96 (q, J=288.2 Hz), 46.50, 37.99, 32.35, 20.56.

$^{19}$F NMR (470.75 MHz, CDCl$_3$): δ −76.02.

HRMS (ESI- TOF MS ES+): m/z calculated for C$_{12}$H$_{15}$NOF$_3$[M+H]$^+$: 246.1106, found 246.1111.

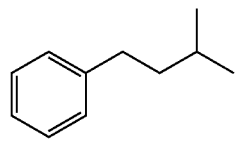

Isopentylbenzene [S12]

Synthesized using a known procedure (*J. Am. Chem. Soc.* 2014, 136, 5783).

$^1$H NMR (500 MHz, CDCl$_3$): δ 7.30-7.26 (m, 2H), 7.21-7.15 (m, 3H), 2.68-2.58 (m, 2H), 1.60 (non, J=12.7 Hz, 1H), 1.55-1.48 (m, 2H), 0.95 (d, J=6.6 Hz, 6H).

$^{13}$C NMR (126 MHz, CDCl$_3$) δ 143.3, 128.5, 128.4, 125.7, 41.0, 34.0, 27.8, 22.7.

S13. Synthesized using a known procedure.[11] The NMR data matched those reported.

S14, S16. Prepared using the general procedure for acetate protection of commercial materials. The NMR data matched those reported in literature.

Compounds S15, S17, and S19 were obtained through commercial sources.

S18 is an amination byproduct.

S20. Prepared according to method reported in literature, the NMR data matched those reported (WO2011091209).

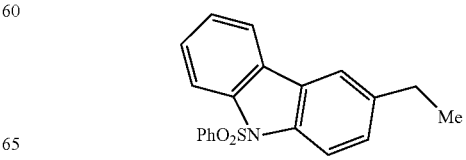

3-ethyl-9-(phenylsulfonyl)-9H-carbazole [S21]

Prepared from commercial 3-ethylcarbazole according to method reported in literature (*Tetrahedron* 1989, 45, 5059).

$^1$H NMR (500 MHz, CDCl$_3$): δ 8.32 (d, J=8.4 Hz, 1H), 8.23 (d, J=8.5 Hz, 1H), 7.88 (d, J=7.7 Hz, 1H), 7.84-7.78 (m, 2H), 7.71 (s, 1H), 7.47 (ddd, J=8.6, 7.3, 1.3 Hz, 1H), 7.43 (t, J=7.5 Hz, 1H). 7.38-7.27 (m, 4H), 2.79 (q, J=7.6 Hz, 2H), 1.31 (t, J=7.6 Hz, 3H).

$^{13}$C NMR (126 MHz, CDCl$_3$): δ 140.33, 138.71, 138.02, 136.71, 133.81, 129.12, 127.74, 127.35, 126.66, 126.65, 126.58, 124.01, 120.05, 118.98, 115.27, 115.05, 28.84, 16.06.

HRMS (ESI– TOF MS ES+): m/z calculated for C$_{20}$H$_{17}$NO$_2$SNa [M+Na]$^+$: 358.0878, found 358.0881.

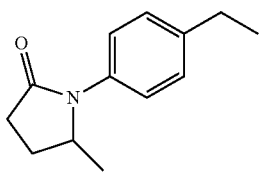

1-(4-ethylphenyl)-5-methylpyrrolidin-2-one [S22]

4-ethyl aniline (1.5 g, 12.4 mmol, 1 equiv.), levulinic acid (2.88 g, 24.76 mmol, 2 equiv.), Et$_3$N (1.25 g, 12.4 mmol, 1 equiv.), and formic acid (0.570 g, 12.4 mmol, 1 equiv.) were added to flame-dried round bottom flask equipped with water-cooled condenser. The reagents were dissolved in DMSO (25 mL, 0.5M) and refluxed at 100° C. for 12 h. The reaction was cooled and water (40 mL) and DCM (40 mL) were added. The organic layer was extracted with water (3×20 mL). The combined aqueous layers were then extracted with DCM (1×40 mL). The combined organic layers were dried over Na$_2$SO$_4$. Flash column chromatography on silica gel (1:1 hexanes:ethyl acetate) gives the product as a brown oil (504.2 mg, 2.48 mmol, 10% yield).

$^1$H NMR (500 MHz, CDCl$_3$): δ 7.28-7.27 (m, 1H), 7.27-7.25 (m, 1H), 7.24-7.21 (m, 2H), 4.27 (d sxt, J=12.3, 1.3 Hz, 1H), 2.69-2.60 (m, 3H), 2.55 (ddd, J=17.0, 9.5, 7.4 Hz, 1H), 2.42-2.34 (m, 1H), 1.80-1.72 (m, 1H), 1.25 (t, J=7.6 Hz, 3H), 1.21 (d, J=6.3 Hz, 3H).

$^{13}$C NMR (126 MHz, CDCl$_3$): δ 174.34, 142.07, 135.22, 128.55, 124.39, 55.93, 31.43, 28.54, 26.96, 20.39, 15.63.

HRMS (ESI– TOF MS ES+): m/z calculated for C$_{13}$H$_{18}$NO [M+H]$^+$: 204.1388, found 204.1395.

Scheme 6. Synthesis of Oxazolidinone S23.

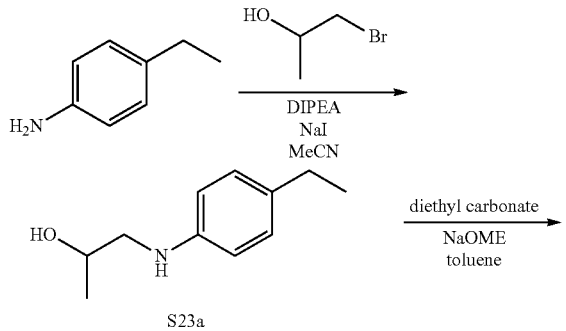

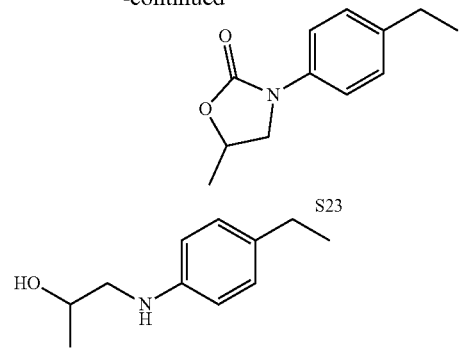

1-((4-ethylphenyl)amino)propan-2-ol [S23a]

4-ethyl aniline (1.45 g, 12 mmol, 1 equiv.), 1-bromo-2-propanol (2 g, 14.4 mmol, 1.2 equiv.), diisopropyl ethyl amine (3.1 g, 24 mmol, 2 equiv.), NaI (1.8 g, 12 mmol, 1 equiv.) and acetonitrile (80 mL, 0.15M) were added to a round bottom flask equipped with a water-cooled condenser under a nitrogen atmosphere. The reaction was refluxed overnight and monitored by TLC. Upon completion, the reaction was poured into a separatory funnel and H$_2$O (20 mL) and DCM (40 mL) were added and shaken. The organic layer was separated and the aqueous layer extracted with DCM (2×20 mL). The combined organic layers were dried over Na$_2$SO$_4$, filtered and evaporated. Flash column chromatography on silica gel using 40% EtOAc in hexanes gives the amino alcohol as a colorless oil in (1.29 g, 7.2 mmol, 60% yield). This substrate contains rotational isomers in the $^1$H NMR.

$^1$H NMR (400 MHz, Chloroform-d): δ 7.03 (d, J=8.2 Hz, 2H), 6.66-6.58 (m, 2H), 4.07-3.96 (m, 0.75H), 3.72 (dd, J=10.6, 4.2 Hz, 0.25H), 3.67-3.55 (m, 0.25H), 3.48 (dd, J=10.6, 6.3 Hz, 0.25H), 3.22 (dd, J=12.9, 3.3 Hz, 0.75H), 3.14 (br s, 2H), 2.98 (dd, J=12.9, 8.7 Hz, 0.75H), 2.55 (q, J=7.6 Hz, 2H), 1.30-1.16 (m, 6H).

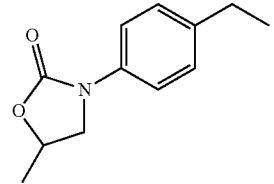

3-(4-ethylphenyl)-5-methyloxazolidin-2-one [S23]

In a flame-dried round bottom flask equipped with a water-cooled condenser was added NaOMe (227 mg, 4.2 mmol, 1.5 equiv.), 1-((4-ethylphenyl)amino)propan-2-ol S23a (500 mg, 2.8 mmol, 1 equiv.) and toluene (5.6 mL, 0.5M). The mixture was stirred for 5 minutes, then diethyl carbonate was added dropwise (500 mg, 4.2 mmol, 1.5 equiv.). The reaction was refluxed to completion (4 h) and monitored by TLC. Upon completion, the reaction was filtered through celite using DCM and concentrated. The crude product was then purified using silica gel flash chromatography with gradient elution (10% EtOAc in hexane to 50% EtOAc in hexane) to give a white solid (459.8 g, 2.24 mmol, 80% yield).

¹H NMR (500 MHz, CDCl₃): δ 7.43 (d, J=8.6 Hz, 2H), 7.20 (d, J=8.8 Hz, 2H), 4.78 (ddq, J=8.2, 7.0, 6.2 Hz, 1H), 4.10 (t, J=8.4 Hz, 1H), 3.61 (dd, J=8.6, 7.0 Hz, 1H), 2.63 (q, J=7.6 Hz, 2H), 1.53 (d, J=6.2 Hz, 3H), 1.22 (t, J=7.6 Hz, 3H).

¹³C NMR (126 MHz, CDCl₃): δ 155.12, 140.24, 136.21, 128.54, 118.54, 69.62, 52.22, 28.34, 20.89, 15.82.

HRMS (ESI– TOF MS ES+): m/z calculated for $C_{12}H_{16}NO_2$ [M+H]⁺: 206.1181, found 206.1172.

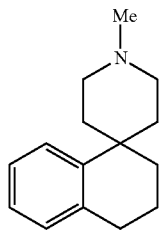 [SMILES: CN1CCC2(CCCc3ccccc32)CC1]

1'-methyl-3,4-dihydro-2H-spiro[naphthalene-1,4'-piperidine] [25]

Synthesized using a previously reported synthesis and the spectral data matches the previously reported data (*J. Chem. Soc. Perkin Trans. I.* 1995, 1273).

¹H NMR (400 MHz, CDCl₃): δ 7.49 (d, J=7.9 Hz, 1H), 7.21-7.15 (m, 1H), 7.08 (td, J=7.3, 1.2 Hz, 1H), 7.16-7.03 (m, 1H), 2.77 (t, J=6.2 Hz, 2H), 2.76-2.70 (m, 2H), 2.35 (s, 3H), 2.26 (td, J=11.8, 1.8 Hz, 2H), 2.16 (td, J=13.8, 3.8 Hz, 2H), 1.87-1.80 (m, 2H), 1.78-1.70 (m, 2H), 1.65-1.57 (m, 2H).

¹³C NMR (101 MHz, CDCl₃): δ 145.16, 137.41, 129.06, 126.92, 126.03, 125.42, 51.84, 46.69, 38.56, 34.86, 30.99, 30.83, 19.02.

HRMS (ESI-TOF MS ES+): m/z calculated for $C_{15}H_{22}N$ [M+H]⁺: 216.1752, found 216.1748.

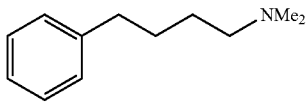 [SMILES: CN(C)CCCCc1ccccc1]

N,N-dimethyl-4-phenylbutan-1-amine [S24]

In a 100 mL round-bottom flask were added 4-phenylbutan-1-amine (1.58 mL, 1.49 g, 10.0 mmol, 1.0 equiv.) and formaldehyde (37 wt %, 7.5 mL, 3.02 g, 100 mmol, 10.0 equiv.). Formic acid (3.8 mL, 4.60 g, 100 mmol, 10.0 equiv.) was then added dropwise. The mixture was then refluxed in a 100° C. oil bath for 4 h, then partitioned between water (50 mL) and CH₂Cl₂ (50 mL), upon which time a saturated potassium carbonate solution (10 mL) was added. The organic layer was isolated, and the aqueous layer was extracted with CH₂Cl₂ (3×50 mL). The organic layers were combined, dried over MgSO₄, and concentrated via rotary evaporation. The crude material was purified by flash chromatography (50 mL basic Al₂O₃Brockmann grade III, 5% EtOAc/Hex (4 column volumes)) to afford the product as a light yellow oil (1.36 g, 7.65 mmol, 76% yield).

Data for S24: These spectral data matched those reported in literature.

¹H NMR (400 MHz, CDCl₃): δ 7.30-7.24 (m, 2H), 7.21-7.14 (m, 3H), 2.63 (t, J=7.6 Hz, 2H), 2.27 (t, J=7.5 Hz, 2H), 2.21 (s, 6H), 1.64 (app p, J=7.2 Hz, 2H), 1.55-1.46 (m, 2H).

¹³C NMR (101 MHz, CDCl₃): δ 142.60, 128.49, 128.34, 125.75, 59.82, 45.63, 35.97, 29.42, 27.52.

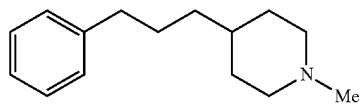 [SMILES: CN1CCC(CCCc2ccccc2)CC1]

1-methyl-4-(3-phenylpropyl)piperidine [S25]

In a 100 mL round-bottom flask equipped with a magnetic stir bar were added 1-methyl-4-(3-phenylpropyl)-1,2,3,6-tetrahydropyridine (717 mg, 3.33 mmol), palladium hydroxide on carbon (20 wt %, 112 mg) and toluene (0.3 M, 11.2 mL). The flask was placed into a metal pressure reactor and filled with hydrogen gas (60 psi). The reaction mixture was stirred for a week. Upon completion, the mixture was filtered and condensed via rotary evaporation. The crude material was purified by flash chromatography (50 mL silica, 25% EtOAc/Hex (4 column volumes)) to afford the product as a colorless oil (392.2 mg, 1.80 mmol, 54% yield).

¹H NMR (500 MHz, CDCl₃): δ 7.30-7.25 (m, 2H), 7.20-7.15 (m, 3H), 2.82 (d, J=11.5 Hz, 2H), 2.59 (t, J=7.8 Hz, 2H), 2.24 (s, 3H), 1.86 (t, J=11.1 Hz, 2H), 1.70-1.57 (m, 4H), 1.32-1.16 (m, 5H).

¹³C NMR (101 MHz, CDCl₃): δ 142.83, 128.45, 128.33, 125.70, 56.18, 46.65, 36.36, 36.27, 35.20, 32.60, 28.89.

HRMS (ESI-TOF MS ES+): m/z calculated for $C_{15}H_{24}N$ [M+H]⁺: 218.1909, found 218.1910.

Scheme 7. Synthesis of 4-(1,2,3,4-Tetrahydronaphthalen-1-yl)pyridine S26.

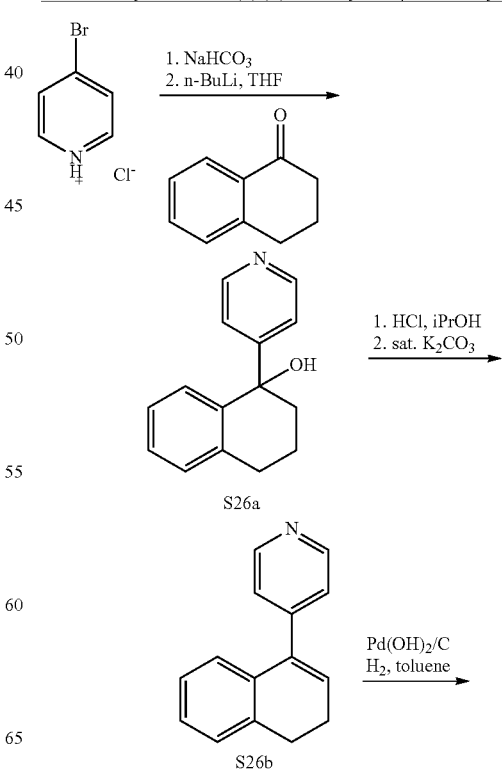

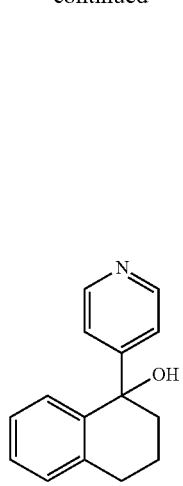

1-(pyridin-4-yl)-1,2,3,4-tetrahydronaphthalen-1-ol [S26a]

To a 500 mL seperatory funnel was added 4-bromopyridine hydrochloride (3.12 g, 16.0 mmol) and diethyl ether (30 mL).

Saturated sodium bicarbonate solution (30 mL) was then added. After the bubbles subsided, the substrate was partitioned between the two layers. The organic layer was isolated, and the aqueous layer was further extracted with Et$_2$O (2×30 mL). The organic layers were combined, dried over MgSO$_4$, and concentrated in vacuo in a 300 mL round-bottom flask. According to literature-reported method (*J. Med. Chem.* 2008, 51, 5009), anhydrous Et$_2$O (60 mL) and tetrahydrofuran (THF) (40 mL) were then added, and the resulting solution was placed in a −78° C. cold bath. n-Butyllithium (1.6 M, 9.9 mL, 15.8 mmol) was quickly added, and the reaction mixture was stirred for 5 s. α-Tetralone (2.10 g, 14.4 mmol) in THF (40 mL) was then quickly added. The reaction was then taken out of the cold bath and stirred overnight at room temperature. Saturated ammonium chloride (0.5 mL) was used to quench the reaction, and the resulting mixture was condensed in vacuo and directly loaded onto a flash column. Purification (150 mL silica, gradient elusion 2% (2 column columes)→5% MeOH/CH$_2$Cl$_2$ (4 column volumes)) afforded the product as an orange solid (1.53 g, 6.80 mmol, 47% yield).

$^1$H NMR (500 MHz, CDCl$_3$): δ 8.54 (d, J=5.0 Hz, 2H), 7.30 (d, J=5.3 Hz, 2H), 7.24 (dd, J=7.4, 1.2 Hz, 1H), 7.19 (td, J=7.6, 0.7 Hz, 1H), 7.13 (td, J=7.5, 0.7 Hz, 1H), 6.93 (d, J=7.5 Hz, 1H), 2.98-2.85 (m, 2H), 2.23 (s, 1H), 2.18-2.10 (m, 1H), 2.09-1.97 (m, 2H), 1.89-1.81 (m, 1H).

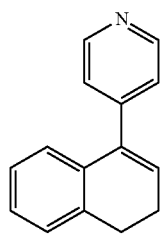 [SMILES: C1=C(c2ccncc2)c2ccccc2CC1]

4-(3,4-dihydronaphthalen-1-yl)pyridine [S26b]

To a 100 mL recovery flask carrying 1-(pyridin-4-yl)-1,2,3,4-tetrahydronaphthalen-1-ol S26a (1.53 g, 6.80 mmol, 1.0 equiv.) were added isopropanol (30 mL) and concentrated hydrochloric acid (12M, 11.3 mL, 136 mmol, 20 equiv.). The resulting solution was refluxed for 4 h. Upon completion, the solvent was removed in vacuo and the residue was redissolved in DCM (30 mL) and basified with saturated K$_2$CO$_3$. The aqueous layer was extracted with DCM (3×30 mL). The organic layers were combined, dried over MgSO$_4$ and concentrated in vacuo. Purification by flash chromatography (50 mL silica, 40% EtOAc/Hex (8 column volumes)) afforded the product as an orange oil (1.27 g, 6.13 mmol, 90% yield).

$^1$H NMR (500 MHz, CDCl$_3$): δ 8.61 (dd, J=4.4, 1.6 Hz, 2H), 7.28 (dd, J=4.4, 1.6 Hz, 2H), 7.22 (dd, J=7.4, 1.2 Hz, 1H), 7.20 (td, J=7.3, 1.3 Hz, 1H), 7.14 (td, J=7.4, 1.8 Hz, 1H), 6.96 (d, J=7.7 Hz, 1H), 6.20 (t, J=4.7 Hz, 1H), 2.86 (t, J=8.0 Hz, 2H), 2.46-2.41 (m, 2H).

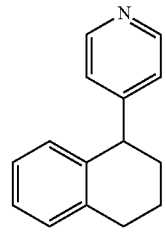 [SMILES: c1ccc2c(c1)CCCC2c1ccncc1]

4-(1,2,3,4-tetrahydronaphthalen-1-yl)pyridine [S26]

To a 100 mL round-bottom flask carrying 4-(3,4-dihydronaphthalen-1-yl)pyridine S26b (1.27 g, 6.13 mmol) were added palladium hydroxide on carbon (20 wt %, 205 mg) and toluene (20.5 mL). The reaction was placed into a metal pressure reactor, sealed and purged with H$_2$ gas (3×app. 100 psi). After purging the metal pressure reactor was pressurized with H$_2$ gas (app. 100 psi) and stirred for 2 days at room temperature. The resulting solution was filtered and concentrated in vacuo. Purification through flash chromatography (50 mL silica, gradient elution 20% (4 column volumes) →40% (8 column volumes)) afforded the product as a colorless viscous oil (1.24 g, 5.90 mmol, 96% yield), which was azeotroped once with anhydrous benzene (5 mL).

$^1$H NMR (400 MHz, CDCl$_3$): δ 8.49 (dd, J=4.5, 1.6 Hz, 2H), 7.16 (dd, J=4.7, 0.8 Hz, 2H), 7.09-7.04 (m, 1H), 7.02 (dd, J=4.7, 1.5 Hz, 2H), 6.79 (d, J=7.6 Hz, 1H), 4.12 (t, J=6.4 Hz, 1H), 2.97-2.80 (m, 2H), 2.23-2.13 (m, 1H), 1.90-1.70 (m, 3H).

$^{13}$C NMR (101 MHz, CDCl$_3$): δ 157.06, 149.18, 137.76, 137.20, 130.11, 129.40, 126.65, 126.04, 124.43, 45.09, 32.68, 29.63, 20.61.

HRMS (ESI-TOF MS ES+): m/z calculated for C$_{15}$H$_{16}$N [M+H]$^+$: 210.1283, found 210.1286.

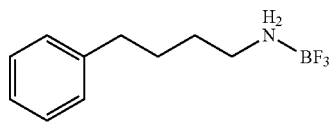

4-phenylbutan-1-amine boron trifluoride complex [S27]

In a flame-dried 100 mL round-bottom flask equipped with a stir bar were added 4-phenylbutan-1-amine (316 µL, 298.5 mg, 2.0 mmol, 1.0 equiv.) and CH$_2$Cl$_2$ (8 mL). The solution was placed in an ice bath, and boron trifluoride diethyl etherate (272 µL, 312.2 mg, 2.2 mmol, 1.1 equiv.) was added dropwise upon stirring. The reaction mixture was kept stirring in an ice bath for 30 min and then allowed to warm up to ambient temperature. The reaction mixture was then further stirred for 1 h, condensed through rotary evaporation and purified through flash chromatography (50 mL silica, 40% EtOAc/Hex (4 column volumes)) to afford the product as a white solid (296.0 mg, 1.36 mmol, 68% yield).

$^1$H NMR (500 MHz, CD$_3$CN): δ 7.33-7.26 (m, 2H), 7.24-7.16 (m, 3H), 4.56 (br s, 2H), 2.76 (p, J=7.2 Hz, 2H), 2.63 (t, J=7.3 Hz, 2H), 1.70-1.54 (m, 4H).

$^{13}$C NMR (126 MHz, CD$_3$CN): δ 143.08, 129.27, 129.24, 126.71, 41.58, 35.73, 29.10, 28.56.

$^{19}$F NMR (470 MHz, CD$_3$CN): δ −151.98 (dd, J=32.6, 15.9 Hz, 3F).

HRMS (ESI-TOF MS ES-): m/z calculated for C$_{10}$H$_{14}$BF$_3$N [M−H]$^+$: 216.1171, found 216.1172.

S28. Prepared according to literature, the NMR data matched those reported (*J. Org. Chem.* 2008, 73, 8623).

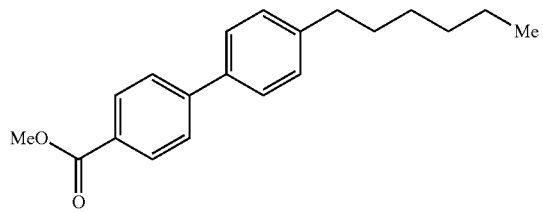 [SMILES: CCCCCCc1ccc(-c2ccc(C(=O)OC)cc2)cc1]

Methyl 4'-hexyl-[1,1'-biphenyl]-4-carboxylate [S29]

To a flame-dried 50 mL round-bottom flask under argon, equipped with a Teflon stir bar was added MeOH (20 mL) and placed in a 0° C. ice-water bath. Thionyl chloride (0.323 mL, 4.43 mmol, 2.5 equiv) was added and the reaction stirred for 15 minutes at which time 4'-hexyl-[1,1'-biphenyl]-4-carboxylic acid (0.50 g, 1.77 mmol, 1 equiv) was added in one portion. The reaction was stirred at room temperature overnight. The solvent was evaporated and the crude oil taken up in toluene and concentrated three consecutive times. The crude product was purified using gradient silica gel flash chromatography (5% ethyl acetate in 95% hexanes to 10% ethyl acetate in 90% hexanes) to give a white solid (0.48 g, 91% yield).

$^1$H NMR (500 MHz, Chloroform-d): δ 8.13-8.07 (m, 2H), 7.69-7.63 (m, 2H), 7.58-7.53 (m, 2H), 7.32-7.26 (m, 2H), 3.94 (s, 3H), 2.66 (app t, J=7.9 Hz, 2H), 1.71-1.61 (m, 2H), 1.43-1.28 (m, 6H), 0.95-0.87 (m, 3H).

$^{13}$C NMR (126 MHz, CDCl$_3$): δ 167.2, 145.7, 143.3, 137.4, 130.2, 129.1, 128.7, 127.2, 126.9, 52.2, 35.8, 31.9, 31.6, 29.2, 22.8, 14.3.

HRMS (ESI-TOF MS ES+): m/z calculated for C$_{20}$H$_{25}$O$_2$ [M+H]$^+$: 297.1855, found 297.1851.

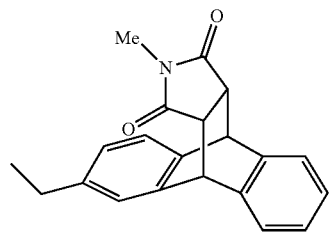 [SMILES: CCc1ccc2c(c1)C1c3ccccc3C2C2C(=O)N(C)C(=O)C12]

rac-(9S,10R,11R,15S)-2-ethyl-13-methyl-9,10-dihydro-9,10-[3,4]epipyrroloanthracene-12,14-dione [(±)S30]

According to literature (*Eur. J. Med. Chem.* 2003, 38, 253), a 50 mL round-bottom flask equipped with a magnetic stir bar was charged with 2-ethylanthracene (936 mg, 4.54 mmol, 1.08 equiv.), N-methylmaleimide (467 mg, 4.20 mmol, 1.0 equiv.) and m-xylene (10 mL). The reaction mixture was heated at reflux for 7 h. Upon completion, the solvent was removed under reduced pressure through rotary evaporation. Purification by flash chromatography on silica (150 mL) eluting with 10% (5 column volumes)→20% EtOAc/hexanes (4 column volumes) yielded a light yellow solid as a mixture of diastereomers. The desired diastereomer was isolated through MPLC (40 g silica) four times eluting with 0%→20% EtOAc/hexanes (40 column volumes) as a white solid (297 mg, 0.937 mmol, 22% yield).

$^1$H NMR (500 MHz, CDCl$_3$): δ 7.39-7.33 (m, 2H), 7.16 (m, 3H), 7.09 (s, 1H), 6.94 (d, J=7.5 Hz, 1H), 4.74 (m, 2H), 3.21-3.16 (m, 2H), 2.55 (q, J=7.5 Hz, 2H), 2.50 (s, 3H), 1.14 (t, J=7.6 Hz, 3H).

$^{13}$C NMR (126 MHz, CDCl$_3$): δ 177.17, 143.36, 141.82, 141.69, 138.53, 135.82, 126.76, 126.73, 126.42, 124.79, 124.55, 124.30, 124.27, 47.22, 47.17, 45.76, 45.32, 28.75, 24.36, 15.94.

HRMS (ESI-TOF MS ES+): m/z calculated for C$_{21}$H$_{20}$O$_2$N [M+H]$^+$: 318.1494, found 318.1495.

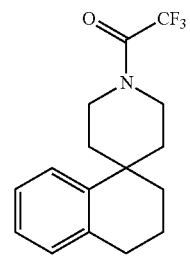 [SMILES: O=C(N1CCC2(CCCc3ccccc32)CC1)C(F)(F)F]

1-(3,4-dihydro-2H-spiro[naphthalene-1,4'-piperidin]-1'-yl)-2,2,2-trifluoroethan-1-one [S31]

Synthesized using a previously reported synthesis above, and the spectral data matches the previously reported data.

$^1$H NMR (400 MHz, Chloroform-d): δ 7.32 (dd, J=7.9, 1.3 Hz, 1H), 7.20 (td, J=7.4, 1.8 Hz, 1H), 7.15-7.06 (m, 2H), 4.56-4.45 (m, 1H), 3.99-3.88 (m, 1H), 3.42 (td, J=13.90, 2.5 Hz, 1H), 3.04 (app t, J=13.4 Hz, 1H), 2.81 (t, J=6.3 Hz, 2H), 2.12-1.99 (m, 2H), 1.99-1.89 (m, 2H), 1.85-1.77 (m, 2H), 1.77-1.69 (m, 2H).

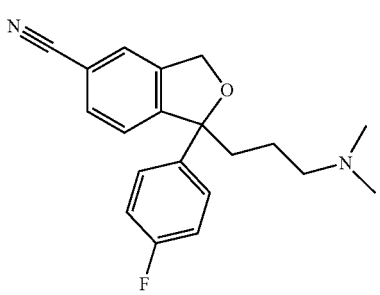 [SMILES: CN(C)CCCC1(c2ccc(F)cc2)OCc2cc(C#N)ccc21]

1-(3-(dimethylamino)propyl)-1-(4-fluorophenyl)-1,
3-dihydroisobenzofuran-5-carbonitrile [(±)S32]

To a 60 mL seperatory funnel, commercial citalopram hydrobromide (203 mg, 0.5 mmol) was partitioned between $CH_2Cl_2$ (5 mL) and water (5 mL). Sodium hydroxide (50% wt, 5 mL) was then added, and the product was repartitioned between the layers. The aqueous layer was extracted with $CH_2Cl_2$ (3×5 mL) and the organic layers were combined, dried over anhydrous $MgSO_4$, filtered and condensed in vacuo. The product was obtained as a colorless gel (163 mg, 0.5 mmol, quantitative yield).

Data for S32: These spectral data matched those reported in literature.

$^1$H NMR (400 MHz, $CDCl_3$): δ 7.59 (dd, J=7.9, 0.8 Hz, 1H), 7.50 (s, 1H), 7.45-7.40 (m, 2H), 7.38 (d, J=7.9 Hz, 1H), 7.04-6.97 (m, 2H), 5.20 (d, J=12.9 Hz, 1H), 5.15 (d, J=12.9 Hz, 1H), 2.26-2.19 (m, 2H), 2.17 (dd, J=9.3, 5.0 Hz, 1H), 2.13 (s, 6H), 2.12-2.08 (m, 1H), 1.52-1.39 (m, 1H), 1.37-1.24 (m, 1H).

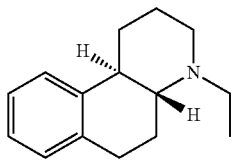 [SMILES: CCN1CCC[C@@H]2c3ccccc3CC[C@H]21]

trans-4-ethyl-1,2,3,4,4a,5,6,10b-octahydrobenzo[f]
quinoline [(±)S33]

To a 100 mL recovery flask equipped with a magnetic stir bar were added trans-1,2,3,4,4a,5,6,10b-octahydrobenzo[/] quinoline (209 mg, 1.10 mmol, 1.0 equiv.), acetic acid (0.22 mL, 1% v/v), and 1,2-dichloroethane (0.05 M, 22 mL). Acetaldehyde (0.31 mL, 242 mg, 5.50 mmol, 5.0 equiv.) was added dropwise as the solution turned orange. The mixture was stirred for 30 min, upon which sodium triacetoxyborohydride (350 mg, 1.65 mmol, 1.5 equiv.) was added in one portion and the reaction solution was stirred overnight at room temperature. The reaction was quenched with saturated $NaHCO_3$ solution (50 mL) and extracted with $CH_2Cl_2$ (3×25 mL). The combined organic layer was washed with saturated aqueous $NaHCO_3$ solution (50 mL) and brine (50 mL). Dried over anhydrous $MgSO_4$, filtered and concentrated. The crude material was thrice purified by column chromatography (20 mL silica, gradient elution 2%→5%→10% $MeOH/CH_2Cl_2$ (5 column volumes each)) to afford the product as a white solid (109.7 mg, 0.509 mmol, 46% yield).

$^1$H NMR (500 MHz, $CDCl_3$): δ 7.29 (d, J=7.6 Hz, 1H), 7.19-7.07 (m, 3H), 3.03 (app d, J=11.3 Hz, 1H), 2.99-2.87 (m, 3H), 2.71 (dq, J=13.9, 7.1 Hz, 1H), 2.67-2.60 (m, 1H), 2.53-2.46 (m, 1H), 2.34-2.25 (m, 2H), 2.16 (td, J=10.5, 3.2 Hz, 1H), 1.89-1.77 (m, 2H), 1.69-1.58 (m, 1H), 1.32-1.22 (m, 1H), 1.05 (t, J=7.2 Hz, 3H).

$^{13}$C NMR (101 MHz, $CDCl_3$): δ 138.83, 135.97, 128.51, 126.13, 126.08, 125.62, 63.31, 52.11, 46.62, 41.59, 29.26, 29.01, 26.11, 24.87, 9.28.

HRMS (ESI-TOF MS ES+): m/z calculated for $C_{15}H_{22}N$ [M+H]$^+$: 216.1752, found 216.1754.

(±)S34 is a minor diastereomer for (±)37.

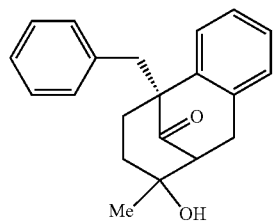 [SMILES: CC1(O)CC[C@]2(Cc3ccccc3)C(=O)C1Cc1ccccc12]

(5R)-5-benzyl-8-hydroxy-8-methyl-5,6,7,8,9,10-
hexahydro-5,9-methanobenzo[8]annulen-11-one
[S35a]

To a flame-dried 300 mL round-bottom flask under argon, equipped with a Teflon stir bar was added 1-benzyl-3,4-dihydronaphthalen-2(1H)-one (5.97 g, 25.3 mmol, 1 equiv), (S)-(−)-methylbenzylamine (3.26 mL, 25.3 mmol, 1 equiv), and toluene (100 mL, 0.25M). The flask was fitted with a Dean-Stark apparatus and water-cooled condenser and refluxed overnight. The reaction was cooled to room temperature then placed in an ice-water bath and cooled to 0° C. Freshly distilled methyl vinyl ketone (2.38 mL, 28.6 mmol, 1.13 equiv) was added dropwise to the reaction and stirred for 30 minutes at 0° C. then brought to 40° C. and stirred overnight. The solution was brought back to 0° C. and acetic acid (0.5 mL) and water (0.5 mL) were added and stirred at room temperature for 2 hours. The reaction was poured into water (100 mL), and extracted three times with ethyl acetate (3×100 mL). The organic extracts were combined and washed with 1M HCl (50 mL), water (50 mL), and saturated $NaHCO_3$(aq) (50 mL). After removal of solvent the crude product was purified using gradient silica gel flash chromatography (15% ethyl acetate in 85% hexanes to 35% ethyl acetate in 65% hexanes) to give a light brown solid (2.18 g, 28% yield).

$^1$H NMR (500 MHz, Chloroform-d): δ 7.21-7.16 (m, 1H), 7.16-7.07 (m, 7H), 7.07-7.02 (m, 1H), 3.69 (d, J=15.6 Hz, 1H), 3.40 (dd, J=17.9, 6.6 Hz, 1H), 3.24 (d, J=15.6 Hz, 1H), 3.17 (d, J=18.1 Hz, 1H), 2.65 (dt, J=6.8, 1.5 Hz, 1H), 2.26 (td, J=13.1, 4.3 Hz, 1H), 1.79 (s, 1H), 1.75-1.67 (m, 1H), 1.58-1.48 (m, 1H), 1.47-1.38 (m, 1H), 1.37 (s, 3H).

$^{13}$C NMR (126 MHz, $CDCl_3$): δ 213.3, 140.4, 138.7, 134.3, 130.3, 127.8, 127.5, 127.1, 126.6, 126.5, 125.5, 79.2, 58.8, 54.2, 41.6, 38.4, 34.4, 33.0, 28.0.

HRMS (ESI-TOF MS ES+): m/z calculated for $C_{21}H_{23}O_2$ [M+H]$^+$: 307.1698, found 307.1694.

Scheme 8. Synthesis of glucocorticoid receptor agonist.

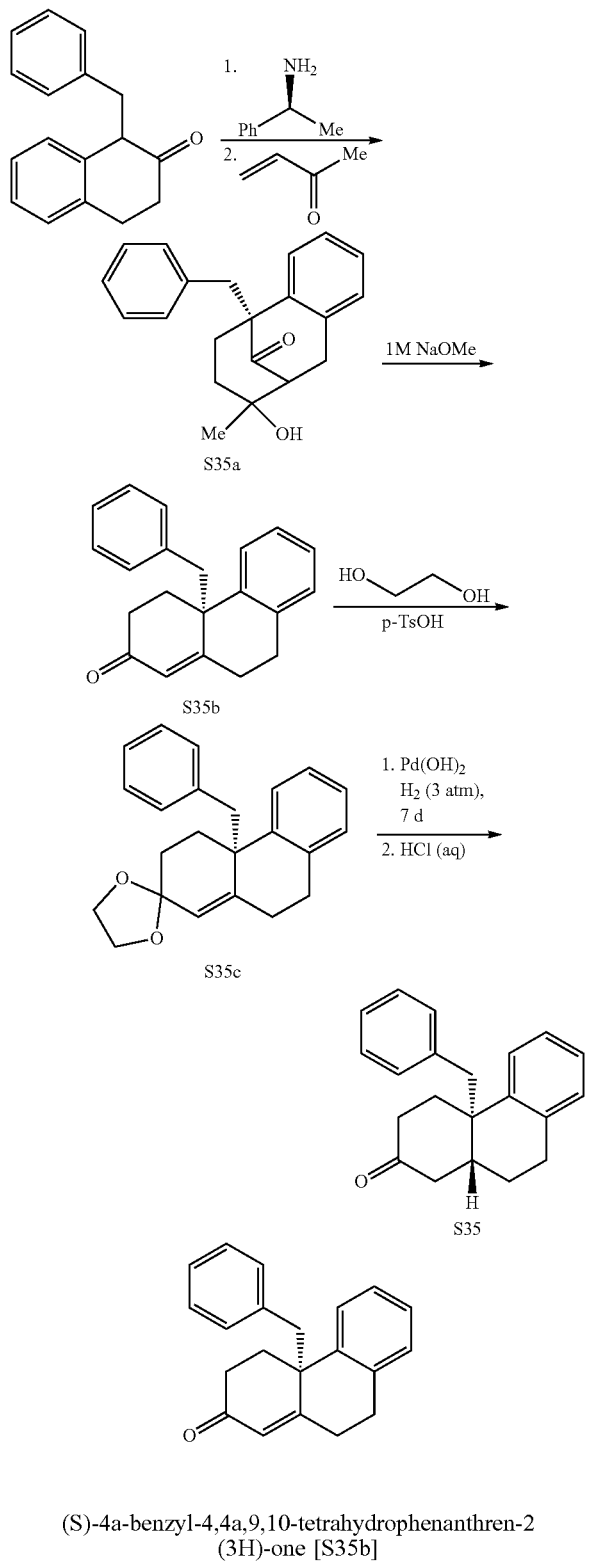

(S)-4a-benzyl-4,4a,9,10-tetrahydrophenanthren-2(3H)-one [S35b]

To a 50 mL round bottom flask equipped with a Teflon stir bar, (5R)-5-benzyl-8-hydroxy-8-methyl-5,6,7,8,9,10-hexahydro-5,9-methanobenzo[8]annulen-11-one S35a (1.9 g, 6.20 mmol, 1 equiv), 1 M NaOMe (3.1 mL), and MeOH (10 mL) were combined and stirred at room temperature for 15 minutes. The reaction was heated to 75° C. for 3 hours and cooled to 0° C. then treated dropwise with AcOH (0.4 mL) and concentrated. The crude oil was dissolved in EtOAc, washed with saturated NaHCO$_3$(aq) (50 mL) and brine (50 mL), dried over Na$_2$SO$_4$ (anhyd), filtered and concentrated to an oil. The crude product was purified using gradient silica gel flash chromatography (10% ethyl acetate in 90% hexanes to 20% ethyl acetate in 80% hexanes) to give an amber and clear oil (1.69 g, 95% yield).

$^1$H NMR (500 MHz, Chloroform-d): δ 7.26-7.22 (m, 2H), 7.21-7.14 (m, 2H), 7.14-7.09 (m, 2H), 7.06 (d, J=7.5 Hz, 1H), 6.77-6.70 (m, 2H), 6.01 (s, 1H), 3.29 (d, J=13.2 Hz, 1H), 3.21 (d, J=13.2 Hz, 1H), 2.88-2.69 (m, 3H), 2.59-2.45 (m, 2H), 2.33 (ddd, J=13.8, 5.2, 3.4 Hz, 1H), 2.09 (td, J=14.5, 14.1, 5.5 Hz, 1H), 1.98-1.87 (m, 1H).

$^{13}$C NMR (126 MHz, CDCl$_3$): δ 198.6, 169.0, 140.9, 137.3, 136.0, 130.1, 128.6, 128.0, 127.0, 126.8, 126.6, 126.5, 125.7, 46.4, 44.2, 36.0, 34.7, 32.2, 30.6.

HRMS (ESI-TOF MS ES+): m/z calculated for C$_{21}$H$_{21}$O [M+H]$^+$: 289.1592, found 289.1589.

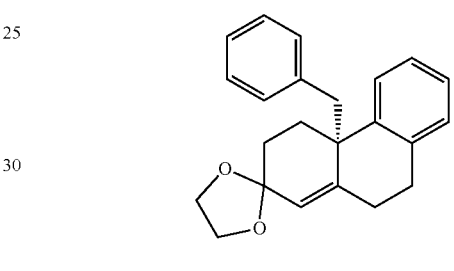

(S)-4a-benzyl-4,4a,9,10-tetrahydro-3H-spiro[phenanthrene-2,2'-[1,3]dioxolane][S35c]

In a flame-dried 200 mL round bottom flask under argon, equipped with a Teflon stir bar was added (S)-4a-benzyl-4,4a,9,10-tetrahydrophenanthren-2(3H)-one S35b (1.2 g, 4.16 mmol, 1 equiv), ethylene glycol (1.16 mL, 20.8 mmol, 5 equiv), p-toluenesulfonic acid (2 mg), and toluene (80 mL, 0.05M). The round bottom was fitted with a Dean-Stark apparatus and water-cooled reflux condenser and refluxed for 16 hours. The solvent was removed and the crude oil taken up in EtOAc (50 mL) and washed with water (20 mL) and brine (20 mL) then dried with K$_2$CO$_3$ (anhyd), filtered and concentrated. The crude product was purified using gradient silica gel flash chromatography (10% ethyl acetate in 90% hexanes to 20% ethyl acetate in 80% hexanes) to give an amber and clear oil (1.08 g, 78% yield).

$^1$H NMR (500 MHz, Chloroform-d): δ 7.41 (d, J=7.9 Hz, 1H), 7.23 (t, J=7.2 Hz, 1H), 7.13-7.04 (m, 2H), 6.98 (t, J=7.6 Hz, 2H), 6.83 (d, J=7.5 Hz, 1H), 6.57-6.50 (m, 2H), 5.63-5.58 (m, 1H), 4.05-3.98 (m, 3H), 3.98-3.92 (m, 1H), 3.38 (d, J=12.9 Hz, 1H), 3.02-2.92 (m, 1H), 2.92-2.84 (m, 1H), 2.76 (d, J=12.9 Hz, 1H), 2.50-2.38 (m, 2H), 2.23 (dt, J=23.2, 4.1 Hz, 1H), 2.19-2.12 (m, 1H), 2.02 (td, J=13.6, 4.1 Hz, 1H), 1.97-1.86 (m, 1H).

$^{13}$C NMR (126 MHz, CDCl$_3$): δ 141.3, 138.1, 135.2, 134.3, 130.1, 127.7, 127.1, 126.1, 126.0, 125.9, 125.8, 123.8, 108.7, 64.6, 64.5, 44.4, 43.2, 42.3, 36.4, 31.6, 29.9.

HRMS (ESI-TOF MS ES+): m/z calculated for C$_{23}$H$_{25}$O$_2$ [M+H]$^+$: 333.1855, found 333.1848.

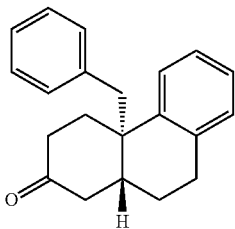 [SMILES: O=C1CC[C@@]2(Cc3ccccc3)c3ccccc3CC[C@@H]2C1]

(−)-(4aS,10aR)-4a-benzyl-3,4,4a,9,10,10a-hexahydrophenanthren-2(1H)-one [S35]

To a flame-dried 50 mL round bottom flask under argon, equipped with a Teflon stir bar was added (S)-4a-benzyl-4,4a,9,10-tetrahydro-3H-spiro[phenanthrene-2,2'-[1,3]dioxolane] S35c (0.50 g, 1.49 mmol, 1 equiv.), toluene (5 mL, 0.3M), and 20 wt % Pd(OH)$_2$/C (0.050 g). The solution was purged with a hydrogen atmosphere and placed in high-pressure reaction vessel, purged with hydrogen three times, and pressurized to 60 psi. The reaction was stirred at room temperature for 5 days, filtered through a celite plug using toluene to make the transfer quantitative, evaporated and purified using gradient silica gel flash chromatography (10% ethyl acetate in 90% hexanes to 20% ethyl acetate in 80% hexanes). After purification, the product was transferred to a 50 mL round-bottom flask and THF (5 mL) and 1M HCl (5 mL) were added and stirred at room temperature for 24 hours. Upon reaction complete by TLC analysis, the reaction was transferred to a separatory funnel and extracted with diethyl ether (2×20 mL), then washed with brine (1×30 mL), dried over Na$_2$SO$_4$ (anhyd), filtered, and evaporated. The crude product was purified using gradient silica gel flash chromatography (10% ethyl acetate in 90% hexanes to 20% ethyl acetate in 80% hexanes) to give a white solid (0.23 g, 54% over 2 steps).

$^1$H NMR (500 MHz, Chloroform-d): δ 7.23-7.10 (m, 5H), 6.89-6.83 (m, 1H), 6.62 (d, J=7.0 Hz, 2H), 6.39 (d, J=7.9 Hz, 1H), 3.17 (d, J=13.2 Hz, 1H), 3.11-2.96 (m, 2H), 2.86 (d, J=12.7 Hz, 1H), 2.86-2.79 (m, 1H), 2.63 (t, J=14.5 Hz, 1H), 2.58-2.50 (m, 2H), 2.46-2.37 (m, 1H), 2.23 (tt, J=13.3, 3.9 Hz, 1H), 2.09-1.94 (m, 1H), 1.82-1.72 (m, 1H), 1.70-1.60 (m, 1H).

$^{13}$C NMR (126 MHz, CDCl$_3$): δ 211.0, 142.0, 137.5, 135.6, 131.0, 129.3, 127.7, 127.4, 126.5, 126.4, 124.6, 44.8, 43.2, 40.1, 38.3, 36.5, 33.4, 28.2, 25.2.

HRMS (ESI-TOF MS ES+): m/z calculated for C$_{21}$H$_{23}$O [M+H]$^+$: 291.1749, found 291.1744.

[α]$_D^{24}$=−123.2° (c=0.19, CHCl$_3$).

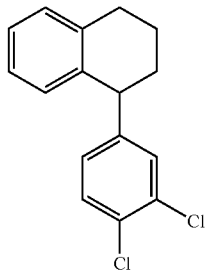 [SMILES: Clc1ccc(C2CCCc3ccccc32)cc1Cl]

1-(3,4-dichlorophenyl)-1,2,3,4-tetrahydronaphthalene [39]

In a round-bottom flask were added 1-(3,4-dichlorophenyl)-1,2-dihydronaphthalene (500 mg, 1.82 mmol, 1 equiv.), EtOAc (3.64 mL, 0.5M) and, Pd/C (5 mol %). The flask was sealed with a rubber septum, purged with hydrogen (3 balloons of hydrogen), and kept on a hydrogen balloon atmosphere at room temperature until reaction completion by TLC (6 h). The reaction was filtered through celite using ethyl acetate as the eluent and concentrated using rotary evaporation. Flash column chromatography on silica gel using hexanes elutes the product as a colorless oil along with minor impurities (approximately 5%) that could not be fully separated and do not affect reactivity (454.6 mg, 1.64 mmol, 90% yield).

$^1$H NMR (500 MHz, CDCl$_3$): δ 7.34 (d, J=8.2 Hz, 1H), 7.19 (d, J=2.1 Hz, 1H), 7.16-7.14 (m, 2H), 7.08-7.04 (m, 1H), 6.92 (dd, J=8.3, 2.1 Hz, 1H), 6.80 (dd, J=7.8, 1.1 Hz, 1H), 4.09 (t, J=6.5 Hz, 1H), 2.96-2.80 (m, 2H), 2.22-2.11 (m, 1H), 1.92-1.70 (m, 3H).

$^{13}$C NMR (126 MHz, CDCl$_3$): δ 147.99, 138.12, 137.69, 132.33, 130.82, 130.30, 130.12, 130.03, 129.35, 128.39, 126.51, 126.03, 45.00, 33.23, 29.73, 20.86.

HRMS (ESI-TOF MS ES+): m/z calculated for C$_{16}$H$_{14}$Cl$_2$ [M]: 276.04726, found 276.04669.

S36 is the aminated product of 39. S37 is the methylated product of S36.

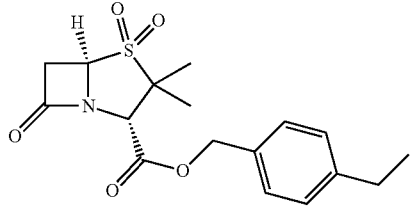 [SMILES: CCc1ccc(COC(=O)[C@@H]2N3C(=O)C[C@H]3S(=O)(=O)C2(C)C)cc1]

4-ethylbenzyl (2S,5R)-3,3-dimethyl-7-oxo-4-thia-1-azabicyclo[3.2.0]heptane-2-carboxylate 4,4-dioxide [S38]

Sulbactam (250 mg, 1.07 mmol) was added to a flame-dried round bottom flask along with dichloromethane (3.15 mL, 0.3M). N-(3-Dimethylaminopropyl)-N'-ethylcarbodiimide hydrochloride (EDC-HCl) (307 mg, 1.6 mmol, 1.6 equiv.) and 4-dimethylaminopyridine (DMAP) (65.4 mg, 0.54 mmol, 0.5 equiv.) under a nitrogen atmosphere and the reaction was stirred at 0° C. for 5 minutes. 4-ethylbenzyl alcohol (218 mg, 1.6 mmol, 1.6 equiv.) was added and stirred at 0° C. for an additional 5 minutes, then warmed to room temperature and stirred for 48 h. After reaction completion, the reaction was diluted with DCM (5 mL) and transferred to separatory funnel. The organic layer was washed with sat. NaHCO$_3$ (1×10 mL). The aqueous layer was then extracted with DCM (2×10 mL). The combined organic layers were washed with a 10% aqueous citric acid solution (1×10 mL). The aqueous layer was again extracted with DCM (2×10 mL). The combined organic layers were washed with brine (1×20 mL), dried over Na$_2$SO$_4$, filtered and concentrated using rotary evaporation. Flash column chromatography on silica using gradient elution (20% EtOAc in hexane to 40% EtOAc in hexane) gave the product as a colorless oil (102 mg, 0.29 mmol, 27% yield).

¹H NMR (500 MHz, CDCl₃): δ 7.28 (d, J=8.1 Hz, 2H), 7.21 (d, J=8.1 Hz, 2H), 5.25 (d, J=11.8 Hz, 1H), 5.14 (d, J=11.9 Hz, 1H), 4.59 (dd, J=4.2, 2.2 Hz, 1H), 4.40 (s, 1H), 3.47 (dd, J=16.2, 4.2 Hz, 1H), 3.42 (dd, J=16.2, 2.2 Hz, 1H), 2.66 (q, J=7.6 Hz, 2H), 1.55 (s, 3H), 1.28 (s, 3H), 1.24 (t, J=7.6 Hz, 3H).

¹³C NMR (126 MHz, CDCl₃): δ 170.82, 166.96, 145.45, 131.71, 129.15, 128.43, 68.28, 63.29, 62.89, 61.19, 38.42, 28.74, 20.24, 18.72, 15.59.

HRMS (ESI-TOF MS ES+): m/z calculated for C₁₇H₂₂NO₅S [M+H]⁺: 352.1219, found 352.1214.

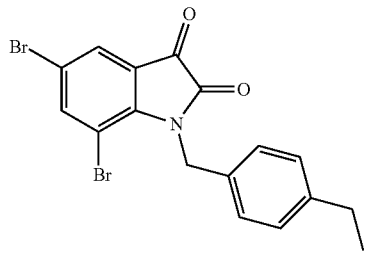 [SMILES: CCc1ccc(CN2C(=O)C(=O)c3cc(Br)cc(Br)c32)cc1]

5,7-dibromo-1-(4-ethylbenzyl)indoline-2,3-dione [S39]

Synthesis: In a flame-dried round bottom was added dibromoisatin (500 mg, 1.64 mmol), K₂CO₃ (227 mg, 1.64 mmol), and DMF (1.6 mL). The reaction was cooled to 0° C. and stirred for 5 min. Then a solution of 1-(bromomethyl)-4-ethylbenzene (653 mg, 3.28 mmol) in DMF (1.6 mL) was added to the reaction dropwise. The reaction was warmed to room temperature and stirred to completion. After completion by TLC, the reaction was diluted with DCM (40 mL) and poured into a separatory funnel then washed with water (20 mL). The organic layer was separated and washed with water (2×20 mL). The combined aqueous layers were extracted with DCM (20 mL), and the organic layers combined and dried over Na₂SO₄. Column chromatography on silica using gradient elution, 10% EtOAc in Hexane→40% EtOAc in hexane gave the product as an orange/red solid (487 mg, 1.15 mmol, 70% yield).

¹H NMR (500 MHz, CDCl₃): δ 7.81 (d, J=2.0 Hz, 1H), 7.71 (d, J=2.0 Hz, 1H), 7.22-7.10 (m, 4H), 5.38 (s, 2H), 2.62 (q, J=7.6 Hz, 2H), 1.21 (t, J=7.6 Hz, 3H).

¹³C NMR (126 MHz, CDCl₃): δ 181.52, 158.48, 146.99, 145.48, 144.05, 132.95, 128.47, 127.66, 126.69, 121.60, 117.26, 105.43, 44.64, 28.62, 15.60.

HRMS (ESI-TOF MS ES+): m/z calculated for C₁₇H₁₄NO₂Br₂ [M+H]⁺: 421.9391, found 421.9380.

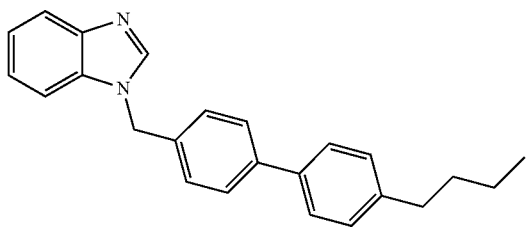 [SMILES: CCCCc1ccc(-c2ccc(Cn3cnc4ccccc43)cc2)cc1]

1-((4'-butyl-[1,1'-biphenyl]-4-yl)methyl)-1H-benzo[d]imidazole [S40]

In a flame-dried 25 mL round-bottom flask under nitrogen with stirring was added K₂CO₃ (864 mg, 6.25 mmol, 5 equiv), benzimidazole (297 mg, 2.51 mmol, 2 equiv), 4-(bromomethyl)-4'-butyl-1,1'-biphenyl (380 mg, 1.25 mg, 1 equiv) and DMF (3 mL). The reaction was stirred for 2 h at 120° C. The reaction was brought to room temperature and poured into a separatory funnel where water (20 mL) was added and the mixture extracted with ethyl acetate (3×20 mL). The combined organic layers were washed with brine (20 mL), dried over Na₂SO₄, filtered and evaporated using rotary evaporation. The product was purified using gradient silica gel flash chromatography (100% DCM to 95/5 DCM/MeOH) to give the pure product as a white solid (217 mg, 51% yield).

¹H NMR (500 MHz, CDCl₃): δ 7.98 (s, 1H), 7.85 (d, J=7.5 Hz, 1H), 7.55 (d, J=8.1 Hz, 2H), 7.47 (d, J=8.1 Hz, 2H), 7.36-7.32 (m, 1H), 7.32-7.27 (m, 2H), 7.25 (d, J=8.1 Hz, 2H), 7.24 (d, J=8.1 Hz, 2H), 5.39 (s, 2H), 2.65 (t, J=7.7 Hz, 2H), 1.63 (p, J=7.6 Hz, 2H), 1.38 (sxt, J=7.4 Hz, 2H), 0.94 (t, J=7.3 Hz, 3H).

¹³C NMR (126 MHz, CDCl₃): δ 142.60, 141.37, 137.70, 134.18, 129.05, 127.67, 127.64, 127.00, 123.25, 122.44, 120.60, 110.20, 48.75, 35.42, 33.74, 22.52, 14.10.

HRMS (ESI-TOF MS ES+): m/z calculated for C₂₄H₂₅N₂ [M+H]⁺: 341.2018, found 341.2012.

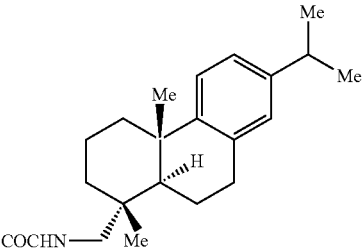

2,2,2-trifluoro-N-(((1R,4aS,10aR)-7-isopropyl-1,4a-dimethyl-1,2,3,4,4a,9,10,10a-octahydrophenanthren-1-yl)methyl)acetamide [S41]

Spectral data matches the previously reported data.

¹H NMR (400 MHz, Chloroform-d): δ 7.18 (d, J=8.2 Hz, 1H), 7.01 (dd, J=8.1, 2.0 Hz, 1H), 6.90 (s, 1H), 6.24 (s, 1H), 3.36-3.22 (m, 2H), 3.00-2.90 (m, 1H), 2.89-2.75 (m, 2H), 2.32 (dt, J=12.9, 2.8 Hz, 1H), 1.94-1.66 (m, 4H), 1.54-1.35 (m, 4H), 1.33-1.19 (m, 9H), 0.99 (s, 3H).

Scheme 9. Synthesis of biflavanoid S42.

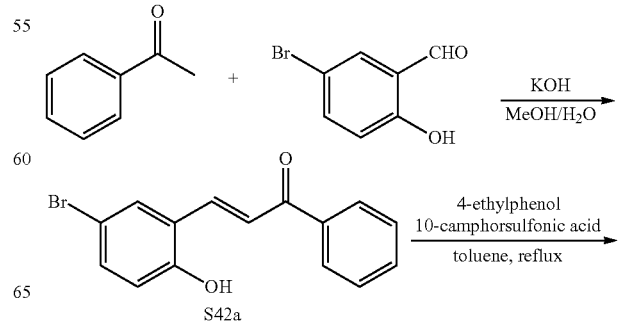

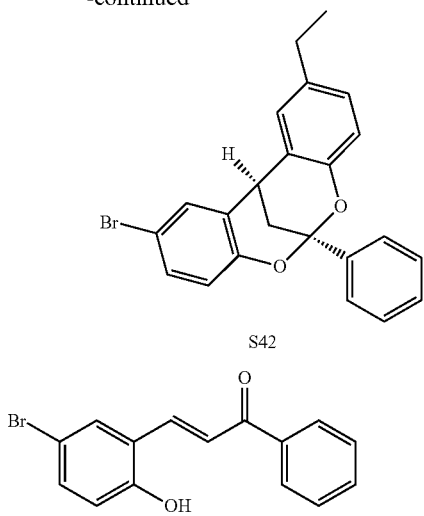

S42

(E)-3-(5-bromo-2-hydroxyphenyl)-1-phenylprop-2-en-1-one [S42a]

Prepared according to literature-reported method (Org. Lett. 2012, 14, 3226). In a 100 mL round-bottom flask equipped with a magnetic stir bar in ice bath were added potassium hydroxide (7.5 g, 134 mmol, 13.4 equiv.), water (1.3 mL), and methanol (6.3 mL). Acetophenone (1.2 mL, 1.20 g, 10 mmol, 1.0 equiv.) was added, and the reaction was stirred for 10 min. 5-Bromosalicylaldehyde (2.01 g, 10 mmol, 1.0 equiv.) was then added. The reaction mixture was then removed from ice bath and stirred overnight. Upon completion, the dark red mixture was acidified with 3M HCl until pH~2. The resulting yellow mixture was extracted with CH$_2$Cl$_2$ (3×20 mL). The combined organic layer was dried over MgSO$_4$ and concentrated in vacuo. Purification by flash chromatography on silica (150 mL) eluting with 20%→30%→40% (2 column volumes each)→100% EtOAc/hexanes (4 column volumes) yielded the product as a yellow powder (2.07 g, 6.83 mmol, 68% yield) with some minor impurities, which were removed in the subsequent step.

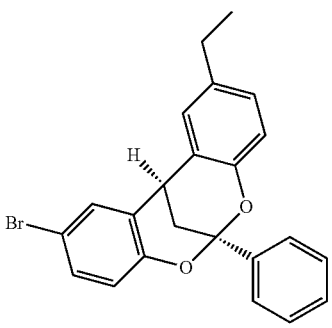 [SMILES: CCc1ccc2c(c1)[C@H]1C[C@](c3ccccc3)(Oc3ccc(Br)cc31)O2]

2-bromo-10-ethyl-6-phenyl-cis-12H-6,12-methanodibenzo [d,g][1,3]dioxocine [(±)S42]

According to literature (Eur. J. Org. Chem. 2014, 418), in a 250 mL round-bottom flask were added (E)-3-(5-bromo-2-hydroxyphenyl)-1-phenylprop-2-en-1-one S42a (1.5 g, 5.0 mmol, 1.0 equiv.), 4-ethylphenol (733 mg, 6.0 mmol, 1.2 equiv.), DL-10-camphorsulfonic acid (174 mg, 0.75 mmol, 0.15 equiv.) and toluene (63 mL). The reaction was placed in 120° C. oil bath and refluxed for 43 h. The resulting dark green mixture was condensed via rotary evaporation. Purification by MPLC (40 g silica) eluting with 0%→10% EtOAc/hexanes (40 column volumes) yielded the product as a light yellow powder (772 mg, 1.90 mmol, 38% yield).

$^1$H NMR (500 MHz, CDCl$_3$): δ 7.75-7.69 (m, 2H), 7.49-7.40 (m, 3H), 7.39 (d, J=2.4 Hz, 1H), 7.24 (dd, J=8.6, 2.4 Hz, 1H), 7.07 (d, J=2.0 Hz, 1H), 7.01 (dd, J=8.3, 2.1 Hz, 1H), 6.96 (d, J=8.3 Hz, 1H), 6.91 (d, J=8.6 Hz, 1H), 4.02 (t, J=2.9 Hz, 1H), 2.61 (qd, J=7.5, 2.1 Hz, 2H), 2.39 (dd, J=13.4, 3.0 Hz, 1H), 2.34 (dd, J=13.4, 3.0 Hz, 1H), 1.24 (t, J=7.6 Hz, 3H).

$^{13}$C NMR (126 MHz, CDCl$_3$): δ 151.41, 149.86, 141.20, 137.74, 130.95, 129.94, 129.02, 128.70, 128.50, 127.91, 126.61, 125.84, 125.37, 118.72, 116.79, 113.44, 98.89, 34.29, 33.18, 28.17, 15.92.

HRMS (ESI-TOF MS ES+): m/z calculated for C$_{23}$H$_{20}$O$_2$Br [M+H]$^+$: 407.0647, found 407.0630.

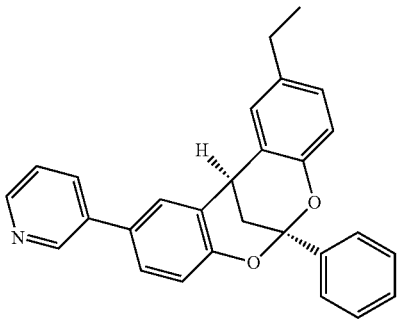 [SMILES: CCc1ccc2c(c1)[C@H]1C[C@@](c3ccccc3)(O2)Oc2ccc(-c3cccnc3)cc21]

3-(10-ethyl-6-phenyl-cis-12H-6,12-methanodibenzo [dg][1,3]dioxocin-2-yl)pyridine [(±)S43]

In a flame-dried 100 mL round-bottom flask equipped with a magnetic stir bar were added 2-bromo-10-ethyl-6-phenyl-cis-12H-6,12-methanodibenzo[d,g][1,3]dioxocine (±)S42 (494 mg, 1.21 mmol, 1.0 equiv.), 3-pyridinylboronic acid (298 mg, 2.43 mmol, 2.0 equiv.), Pd(dppf)Cl$_2$·CH$_2$Cl$_2$ (99 mg, 0.121 mmol, 0.10 equiv.), and potassium carbonate (326 mg, 2.36 mmol, 2.0 equiv.) under N$_2$ atmosphere. Nitrogen-degassed water (0.5 mL) and 1,4-dioxane (2 mL) were added, and the septa was quickly replaced with a polyethylene yellow cap and secured with electric tape. The flask was then placed into 95° C. oil bath and stirred for 3 h. Upon completion, the reaction was quenched with water (10 mL), and extracted with EtOAc (3×10 mL). The organic layers were combined, dried over MgSO$_4$, and condensed through rotary evaporation. Purification by flash chromatography on silica (50 mL) eluting with 20% (6 column volumes)→30%→40% (4 column volumes each) EtOAc/hexanes yielded the product as a light yellow powder (291 mg, 0.718 mmol, 59% yield).

$^1$H NMR (500 MHz, CDCl$_3$): δ 8.82 (s, 1H), 8.57 (d, J=4.2 Hz, 1H), 7.83 (dt, J=7.9, 1.9 Hz, 1H), 7.79-7.74 (m, 2H), 7.51-7.45 (m, 3H), 7.45-7.40 (m, 1H), 7.39-7.32 (m, 2H), 7.14 (d, J=8.4 Hz, 1H), 7.12 (d, J=1.9 Hz, 1H), 7.01 (dd, J=8.3, 1.9 Hz, 1H), 6.98 (d, J=8.3 Hz, 1H), 4.15 (t, J=2.8 Hz, 1H), 2.59 (q, J=7.5 Hz, 2H), 2.44 (d, J=2.9 Hz, 2H), 1.22 (t, J=7.6 Hz, 3H).

¹³C NMR (126 MHz, CDCl₃): δ 152.51, 149.91, 148.24, 148.19, 141.37, 137.69, 136.36, 134.14, 131.32, 128.99, 128.51, 127.81, 127.41, 127.04, 126.56, 126.08, 125.89, 125.82, 123.65, 117.65, 116.81, 99.01, 34.60, 33.48, 28.17, 15.94.

HRMS (ESI-TOF MS ES+): m/z calculated for $C_{28}H_{24}O_2N$ [M+H]⁺: 406.1807, found 406.1804.

S44 is the minor diastereomer of amination product 48.
S45 is the minor diastereomer of amination product 49.

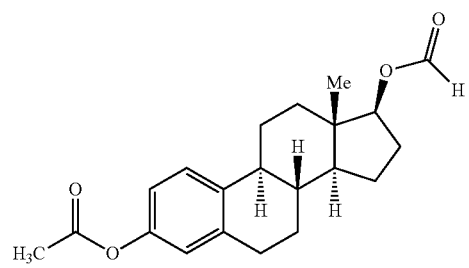

(13S,17S)-17-(formyloxy)-13-methyl-7,8,9,11,12,13, 14,15,16,17-decahydro-6H-cyclopenta[a]phenanthren-3-yl acetate [48a]

In a flame-dried round bottom flask equipped with a stir bar under nitrogen was added (8R,9S,13S,14S,17S)-17-hydroxy-13-methyl-7,8,9,11,12,13,14,15,16,17-decahydro-6H-cyclopenta[a]phenanthren-3-yl acetate (500 mg, 1.60 mmol, 1 equiv) and DMF (409 mg, 5.6 mmol, 3.5 equiv). The reaction was cooled to 0° C. and oxalyl chloride was added dropwise (630 mg, 4.96 mmol, 3.1 equiv). The reaction was warmed to room temperature and stirred overnight. Upon reaction completion, water (10 mL) was added and the contents were transferred to a separatory funnel. The contents were extracted with DCM (3×10 mL). The combined organic layers were washed with water (3×20 mL), dried over Na₂SO₄, filtered and concentrated using rotary evaporation. Silica gel flash column chromatography (20% EtOAc in 80% hexanes) gave the pure product as a white solid (411 mg, 1.2 mmol, 75% yield).

¹H NMR (400 MHz, Chloroform-d): δ 8.11 (s, 1H), 7.28 (d, J=8.5 Hz, 1H), 6.84 (dd, J=8.4, 2.4 Hz, 1H), 6.79 (d, J=2.3 Hz, 1H), 4.79 (t, J=8.4 Hz, 1H), 2.97-2.79 (m, 2H), 2.37-2.19 (m, 6H), 1.99-1.84 (m, 2H), 1.83-1.71 (m, 1H), 1.70-1.54 (m, 1H), 1.54-1.23 (m, 6H), 0.85 (s, 3H).

¹³C NMR (126 MHz, CDCl₃): δ 169.97, 161.32, 148.57, 138.25, 137.86, 126.54, 121.65, 118.75, 82.69, 49.91, 44.08, 43.08, 38.29, 36.90, 29.61, 27.71, 27.13, 26.10, 23.41, 21.27, 12.19.

HRMS (ESI-TOF MS ES+): m/z calculated for $C_{19}H_{25}O_3$ [M-Ac+H₂]⁺: 301.1798, found 301.1797.

Scheme 10. Synthesis of abiraterone analogue 49a.

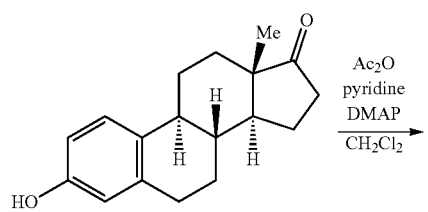

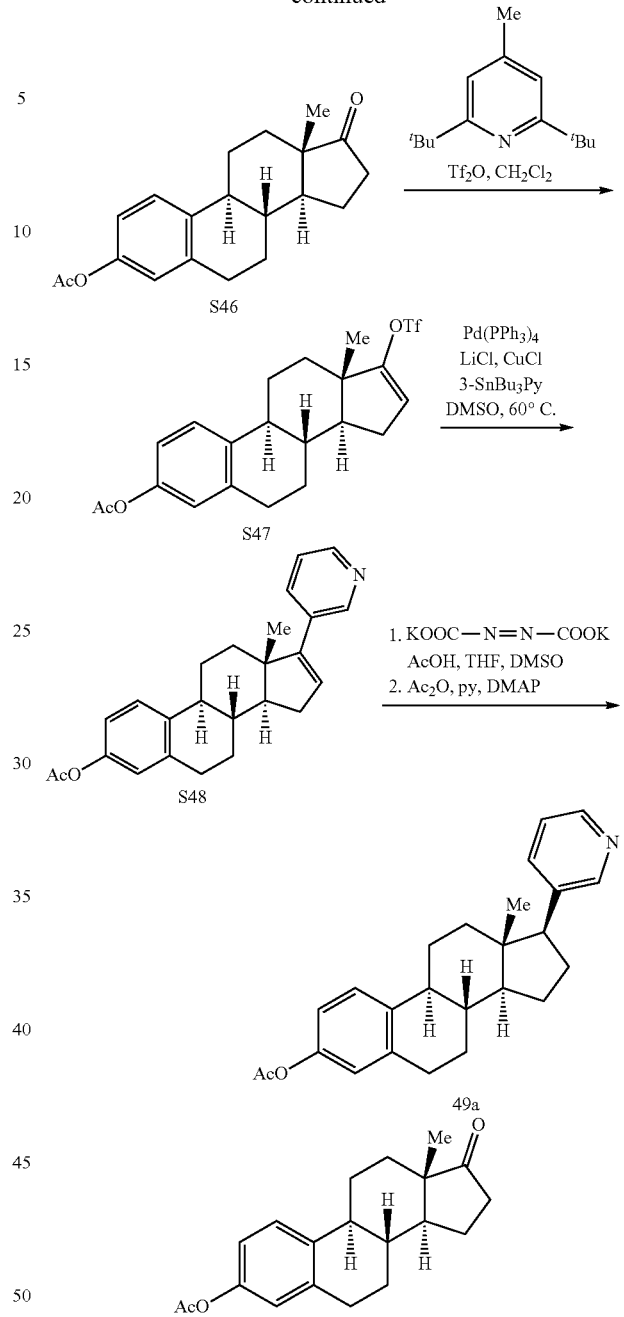

(8R,9S,13S,14S)-13-methyl-17-oxo-7,8,9,11,12,13, 14,15,16,17-decahydro-6H-cyclopenta[a]phenanthren-3-yl acetate [S46]

In a flame-dried 100 mL round bottom flask equipped with a stir bar was charged (+)-estrone (2.70 g, 10.0 mmol, 1.0 equiv.), pyridine (4.0 mL, 3.96 g, 50.0 mmol, 5.0 equiv.), 4-dimethylaminopyridine (DMAP) (122.2 mg, 1.0 mmol, 0.10 equiv.) and CH₂Cl₂ (20 mL). The reaction mixture was placed in ice bath with stirring, and acetic anhydride (2.8 mL, 3.06 g, 30.0 mmol, 3.0 equiv.) was added dropwise via syringe. The reaction mixture was stirred at 0° C. for 5 min and then allowed to warm to ambient temperature and stirred overnight. The reaction was washed with water (20 mL), 1

M HCl (4×20 mL) and brine (20 mL). The organic layer was separated, dried over MgSO₄ and concentrated in vacuo. Purification by flash chromatography on silica (75 mL) eluting with 10%→25%→40% EtOAc/hexanes (2.5 column volumes each) yielded the product as a white powder (3.03 g, 9.70 mmol, 97% yield).

¹H NMR (500 MHz, CDCl₃): δ 7.29 (d, J=8.4 Hz, 1H), 6.85 (dd, J=8.4, 2.4 Hz, 1H), 6.81 (d, J=2.3 Hz, 1H), 2.90 (dd, J=8.8, 4.1 Hz, 2H), 2.51 (dd, J=19.0, 8.6 Hz, 1H), 2.41 (ddd, J=12.4, 7.0, 3.7 Hz, 1H), 2.33-2.24 (m, 1H), 2.29 (s, 3H), 2.19-2.11 (m, 1H), 2.09-1.98 (m, 2H), 1.98-1.93 (m, 1H), 1.68-1.40 (m, 6H), 0.91 (s, 3H).

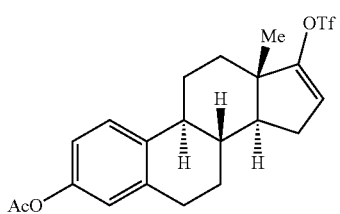

(8R,9S,13S,14S)-13-methyl-17-(((trifluoromethyl)sulfonyl)oxy)-7,8,9,11,12,13,14,15-octahydro-6H-cyclopenta[a]phenanthren-3-yl acetate [S47]

In a flame-dried 50 mL round bottom flask equipped with a stir bar was added S46 (661 mg, 2.11 mmol, 1.0 equiv.), 2,6-di-tert-butyl-4-methylpyridine (448 mg, 2.18 mmol, 1.03 equiv.) and CH₂Cl₂ (5.8 mL). Trifluoromethanesulfonic anhydride (613 mg, 2.17 mmol, 1.03 equiv.) was added dropwise into the reaction mixture while stirring. The reaction was stirred for 6 h. Saturated NaHCO₃ (10 mL) was then added to quench the reaction and the aqueous layer was extracted with CH₂Cl₂ (3×10 mL). The combined organic layer was washed with saturated NaHCO₃ (5 mL) and brine (5 mL), dried over MgSO₄ and concentrated in vacuo. Purification by flash chromatography on silica (50 mL) eluting with 2% (4 column volumes)→5% EtOAc/hexanes (6 column volumes) yielded the product as a white solid (757 mg, 1.70 mmol, 81% yield).

¹H NMR (400 MHz, CDCl₃): δ 7.25 (d, J=8.0 Hz, 1H), 6.85 (dd, J=8.5, 2.5 Hz, 1H), 6.81 (d, J=2.4 Hz, 1H), 5.62 (dd, J=3.3, 1.7 Hz, 1H), 2.91 (dd, J=9.8, 5.1 Hz, 2H), 2.44-2.37 (m, 1H), 2.33 (ddd, J=14.9, 6.3, 3.5 Hz, 2H), 2.29 (s, 3H), 2.10 (ddd, J=14.9, 11.2, 1.7 Hz, 1H), 1.96-1.87 (m, 2H), 1.79 (td, J=11.3, 6.3 Hz, 1H), 1.71-1.57 (m, 3H), 1.51-1.37 (m, 1H), 1.00 (s, 3H).

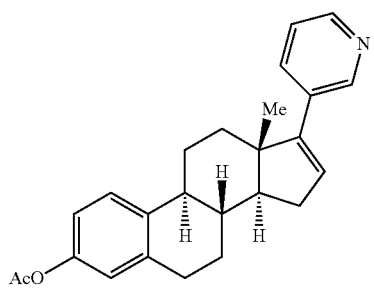

(8S,9S,13S,14S)-13-methyl-17-(pyridin-3-yl)-7,8,9,11,12,13,14,15-octahydro-6H-cyclopenta[a]phenanthren-3-yl acetate [S48]

In a flame-dried 300 mL round-bottom flask containing LiCl (1.05 g, 24.7 mmol, 6.0 equiv.) and equipped with a magnetic stir bar were added S47 (1.83 g, 4.12 mmol, 1.0 equiv.), Pd(PPh₃)₄ (476 mg, 0.412 mmol, 0.10 equiv.), CuCl (2.04 g, 20.6 mmol, 5.0 equiv.), and DMSO (154 mL). 3-(tributylstannyl)pyridine (2.6 mL, 3.03 g, 8.24 mmol, 2.0 equiv.) was then added via syringe. The mixture was degassed through freeze-pump-thaw (−78° C.→0° C.) three times, and was stirred for 1 h at room temperature. The reaction flask was then placed into 60° C. oil bath and stirred vigorously for 13 h. Upon completion, the reaction was quenched with the mixed solution of concentrated NH₄OH (5.5 mL) and brine (200 mL), and extracted with diethyl ether (4×50 mL). The organic layers were then combined, dried over MgSO₄ and concentrated in vacuo. Purification by flash chromatography on silica (150 mL) eluting with 40% EtOAc/hexanes (7.5 column volumes) yielded the product as a white powder (1.31 g, 3.52 mmol, 85% yield).

¹H NMR (400 MHz, CDCl₃): δ 8.65 (d, J=2.1 Hz, 1H), 8.48 (dd, J=4.8, 1.5 Hz, 1H), 7.69 (app d, J=8.1 Hz, 1H), 7.29 (d, J=8.2 Hz, 1H), 7.27-7.23 (m, 1H), 6.85 (dd, J=8.5, 2.3 Hz, 1H), 6.81 (dd, J=2.3 Hz, 1H), 6.03 (dd, J=3.0, 1.6 Hz, 1H), 2.93 (dd, J=11.3, 5.9 Hz, 2H), 2.44-2.32 (m, 3H), 2.29 (s, 3H), 2.20-2.11 (m, 2H), 2.02-1.93 (m, 1H), 1.82 (td, J=11.4, 6.5 Hz, 1H), 1.75-1.64 (m, 3H), 1.56-1.44 (m, 1H), 1.04 (s, 3H).

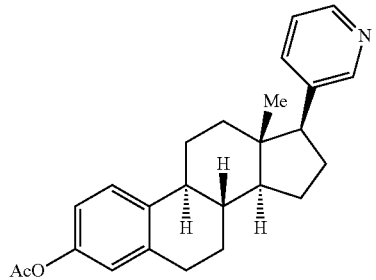

(8S,9S,13S,14S,17S)-13-methyl-17-(pyridin-3-yl)-7,8,9,11,12,13,14,15,16,17-decahydro-6H-cyclopenta[a]phenanthren-3-yl acetate [49a]

In a flame-dried 200 mL round bottom flask equipped with a stir bar was added S48 (1.31 g, 3.52 mmol, 1.0 equiv.), THF (33 mL) and DMSO (33 mL). The mixture was cooled down to 0° C. upon stirring, and potassium azodicarboxylate (KOOC—N═N—COOK) (3×4.56 g, 70.5 mmol, 20 equiv.) was added in three equal portion over the course of 2 h, each followed by the addition of AcOH (3×2.7 mL, 3×2.82 g, 140.7 mmol, 40 equiv.). After adding the last portion of potassium azodicarboxylate, the reaction was allowed to warm to ambient temperature and stirred overnight. The reaction was quenched with brine (100 mL) and extracted with diethyl ether (3×50 mL). The organic layers were combined, dried over MgSO₄, condensed, transferred into a 100 mL round-bottom flask and concentrated in vacuo. Dichloromethane (7.0 mL), pyridine (1.4 mL, 1.39 g, 17.6 mmol, 5.0 equiv.), 4-dimethylaminopyridine (DMAP) (43 mg, 0.35 mmol, 0.10 equiv.), and acetic anhydride (1.0 mL, 1.08 g, 10.6 mmol, 3.0 equiv.) were added. The reaction was stirred overnight, and washed with water (5×5 mL) and brine (5 mL). The organic layer was dried over MgSO$_4$ and concentrated in vacuo. Purification by MPLC (40 g silica) eluting with 0%→70% EtOAc/hexanes (25 column volumes) yielded the product as a white powder (1.01 g, 2.69 mmol, 76% yield over 2 steps).

$^1$H NMR (500 MHz, CDCl$_3$): δ 8.49 (d, J=1.9 Hz, 1H), 8.46 (dd, J=4.7, 1.3 Hz, 1H), 7.55 (app d, J=7.9 Hz, 1H), 7.27 (d, J=8.9 Hz, 1H), 7.22 (dd, J=7.8, 4.8 Hz, 1H), 6.83 (dd, J=8.5, 2.3 Hz, 1H), 6.80 (d, J=2.0 Hz, 1H), 2.92-2.85 (m, 2H), 2.78 (t, J=9.8 Hz, 1H), 2.34-2.28 (m, 2H), 2.28 (s, 3H), 2.19-2.09 (m, 1H), 2.09-2.00 (m, 1H), 1.99-1.89 (m, 2H), 1.73-1.66 (m, 1H), 1.54-1.37 (m, 6H), 0.52 (s, 3H).

$^{13}$C NMR (126 MHz, CDCl$_3$): δ 169.99, 150.54, 148.52, 147.72, 138.36, 138.13, 136.38, 135.75, 126.50, 122.89, 121.63, 118.68, 55.37, 54.68, 44.79, 44.24, 38.94, 37.56, 29.72, 27.70, 26.20, 26.06, 24.30, 21.27, 12.85.

HRMS (EI+): m/z calculated for C$_{25}$H$_{29}$O$_2$N [M]$^+$: 375.2198, found 375.2199.

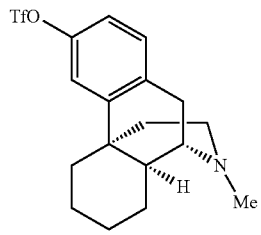 [SMILES: CN1CC[C@@]23CCCC[C@@H]2[C@@H]1Cc1ccc(OS(=O)(=O)C(F)(F)F)cc13]

(4bS,8aS,9S)-11-methyl-6,7,8,8a,9,10-hexahydro-5H-9,4b-(epiminoethano)phenanthren-3-yl trifluoromethanesulfonate [S49a]

To a 100 mL round-bottom flask containing dextromethorphan hydrobromide monohydrate (4.99 g, 13.5 mmol, 1.0 equiv.) was added hydrobromic acid (48 wt %, 29.5 mL, 21.1 g, 261 mmol, 19 equiv.). The reaction was refluxed overnight, poured on ice, and basified with saturated potassium carbonate solution. The aqueous layer was extracted with chloroform (3×50 mL). The organic layers were combined, dried over MgSO$_4$, filtered, and condensed through rotary evaporation to give the phenol intermediate as a white powder. In a 200 mL round-bottom flask carrying the intermediate were added CH$_2$Cl$_2$ (90 mL) and triethylamine (37.6 mL, 27.3 g, 270 mmol, 20 equiv.). The mixture was cooled to 0° C. in ice bath, and N-Phenyl-bis(trifluoromethanesulfonimide) (7.22 g, 20.2 mmol, 1.5 equiv.) was added in one portion. The reaction was allowed to warm to room temperature and stirred overnight. The reaction was then diluted with CH$_2$Cl$_2$, washed with sodium hydroxide (3×50 mL), and brine (50 mL). The organic layer was dried over MgSO$_4$, filtered, and condensed through rotary evaporation. Purification by flash chromatography on silica (250 mL) eluting with 2%→5%→10% (2 column volumes each) MeOH/CH$_2$Cl$_2$ doped with 2% NH$_4$OH yielded the product as an orange oil (4.49 g, 11.5 mmol, 86% yield).

$^1$H NMR (500 MHz, CDCl$_3$): δ 7.18 (d, J=8.5 Hz, 1H), 7.12 (s, 1H), 7.03 (dd, J=8.4, 1.6 Hz, 1H), 3.05 (d, J=18.7 Hz, 1H), 2.86-2.80 (m, 1H), 2.62 (dd, J=18.7, 5.7 Hz, 1H), 2.45 (dd, J=12.0, 4.0 Hz, 1H), 2.39 (s, 3H), 2.30 (d, J=14.1 Hz, 1H), 1.99 (td, J=12.3, 2.6 Hz, 1H), 1.86 (app d, J=12.7 Hz, 1H), 1.78 (td, J=12.8, 4.7 Hz, 1H), 1.66 (d, J=12.8 Hz, 1H), 1.56 (d, J=13.1 Hz, 1H), 1.48-1.34 (m, 3H), 1.30 (d, J=13.2 Hz, 1H), 1.19 (q, J=13.3 Hz, 1H), 1.04 (qd, J=12.8, 3.4 Hz, 1H).

Scheme 11. Synthesis of dextromethorphan derivative.

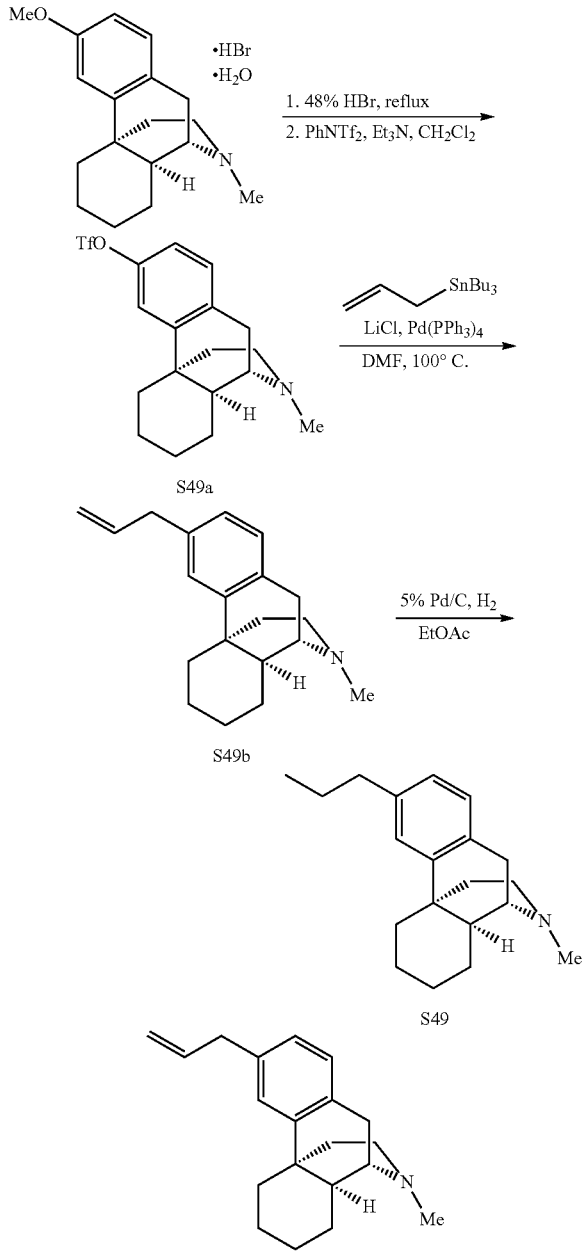

(4bS,8aS,9S)-3-allyl-11-methyl-6,7,8,8a,9,10-hexahydro-5H-9,4b-(epiminoethano)phenanthrene [S49b]

To a flame-dried 200 mL round-bottom flask were added (4bS,8aS,9S)-11-methyl-6,7,8,8a,9,10-hexahydro-5H-9,4b-(epiminoethano)phenanthren-3-yl trifluoromethanesulfonate S49a (2.33 g, 5.99 mmol, 1.0 equiv.), LiCl (1.02 g, 24.0 mmol, 4.0 equiv.), Pd(PPh$_3$)$_4$ (207.7 mg, 0.180 mmol, 0.030 equiv.), allyltributylstannane (2.1 mL, 2.18 g, 6.59 mmol, 1.1 equiv.), and DMF (24 mL, 0.25 M). The reaction was heated to 100° C. and stirred overnight. Upon cooling to room temperature, the reaction was washed with 10% ammonia solution (24 mL). The aqueous layer was extracted with ethyl acetate (3×30 mL). The organic layers were combined, dried over $MgSO_4$, filtered, and condensed via rotary evaporation. Purification by flash chromatography on silica (200 mL) eluting with 2% (1.5 column volumes)→5% (2.5 column volumes) $MeOH/CH_2Cl_2$ doped with 2% $NH_4OH$ yielded the product as a yellow oil (1.41 g, 5.02 mmol, 84% yield).

$^1$H NMR (500 MHz, $CDCl_3$): δ 7.05 (s, 1H), 7.03 (d, J=7.8 Hz, 1H), 6.94 (d, J=7.7 Hz, 1H), 5.97 (ddt, J=16.9, 1.0, 6.7 Hz, 1H), 5.10-5.01 (m, 2H), 3.35 (d, J=6.6 Hz, 1H), 3.01 (d, J=18.4 Hz, 1H), 2.84-2.78 (m, 1H), 2.62 (dd, J=18.3, 5.6 Hz, 1H), 2.48-2.36 (m, 2H), 2.40 (s, 3H), 2.07 (td, J=12.1, 2.6 Hz, 1H), 1.83 (app d, J=12.5 Hz, 1H), 1.74 (td, J=12.5, 4.6 Hz, 1H), 1.63 (d, J=12.6 Hz, 1H), 1.51 (d, J=12.4 Hz, 1H), 1.45-1.20 (m, 5H), 1.13 (qd, J=12.4, 3.2 Hz, 1H).

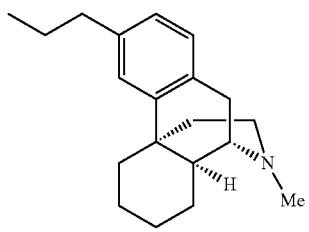 [SMILES: CCCc1ccc2c(c1)[C@]13CCCC[C@@H]1[C@H](C2)N(C)CC3]

(4bS,8aS,9S)-11-methyl-3-propyl-6,7,8,8a,9,10-hexahydro-5H-9,4b-(epiminoethano)phenanthrene [S49]

To a 100 mL round-bottom flask were added (4bS,8aS, 9S)-3-allyl-11-methyl-6,7,8,8a,9,10-hexahydro-5H-9,4b-(epiminoethano)phenanthrene S49b (1.41 g, 5.02 mmol, 1.0 equiv.), palladium on carbon (5% wt, 141 mg, 0.066 mmol, 0.013 equiv.), and ethyl acetate (20 mL). Hydrogen gas was allowed to pass through the reaction mixture, which was stirred overnight. The reaction progress was monitored by crude NMR. Upon completion, the palladium catalyst was removed via filtration, and the filtrate was condensed via rotary evaporation to give the product as a yellow gel (1.40 g, 4.94 mmol, 98% yield).

$^1$H NMR (500 MHz, $CDCl_3$): δ 7.03 (d, J=1.1 Hz, 1H), 7.01 (d, J=7.7 Hz, 1H), 6.93 (dd, J=7.7, 1.6 Hz, 1H), 3.00 (d, J=18.3 Hz, 1H), 2.80 (dd, J=5.4, 3.1 Hz, 1H), 2.60 (dd, J=18.3, 5.7 Hz, 1H), 2.54 (dt, J=8.2, 3.7 Hz, 2H), 2.46-2.38 (m, 2H), 2.39 (s, 3H), 2.07 (td, J=12.2, 3.2 Hz, 1H), 1.82 (dt, J=12.8, 3.0 Hz, 1H), 1.73 (td, J=12.6, 4.8 Hz, 1H), 1.67-1.58 (m, 3H), 1.51 (app d, J=12.0 Hz, 1H), 1.44-1.24 (m, 5H), 1.14 (qd, J=12.1, 3.5 Hz, 1H), 0.93 (t, J=7.3 Hz, 3H).

$^{13}$C NMR (126 MHz, $CDCl_3$): δ 140.61, 139.99, 134.66, 127.63, 125.66, 125.46, 58.30, 47.48, 45.49, 42.86, 42.15, 38.17, 37.03, 36.60, 26.83, 26.71, 24.95, 24.00, 22.28, 14.02

HRMS (ESI-TOF MS ES+): m/z calculated for $C_{20}H_{30}N$ $[M+H]^+$: 284.2378, found 284.2372.

$[\alpha]_D^{24}$=+59.0° (c=1.08, $CHCl_3$).

Example 8. HPLC Methods for the Determination of Product Selectivity

HPLC analysis was used to find the detection limit of these compounds to determine the selectivity of the disclosed reaction. As shown below, standards for both possible products were made using the reported rhodium catalyzed C—H amination procedure above. A Zorbax CN 4.6×250 column with a 1.0 mL/min flow rate was used with a 95:5 hexanes:isopropanol mobile phase.

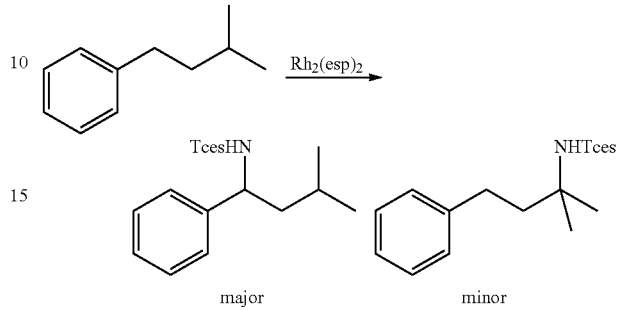

Scheme 12. Rh-catalyzed C—H amination of isopentylbenzene.

The products were purified and isolated as inseparable mixtures. The purified mixture used for determining the HPLC detection limit contained a 10:1 ratio of benzylic to tertiary amination. A solution of 10 mg of the mixture in 1 mL of acetonitrile (0.0267 mmol/mL concentration) was then diluted by a factor of 10 to give 1 mg in 1 mL. This solution was again diluted to give a final sample containing 0.1 mg in 1 mL of acetonitrile. A 2 L sample of this mixture was the concentration at which none of the tertiary product was detected by HPLC.

The manganese-catalyzed amination protocol was performed on isopentyl benzene and the crude reaction was analyzed by HPLC. No tertiary product was detected. Due to the high detection limit of the HPLC, it was concluded that the selectivity of the disclosed reaction is at least 100:1 in this case.

Likewise, the same approach was used to determine the detection limit of the minor mono-amination product in the following reaction.

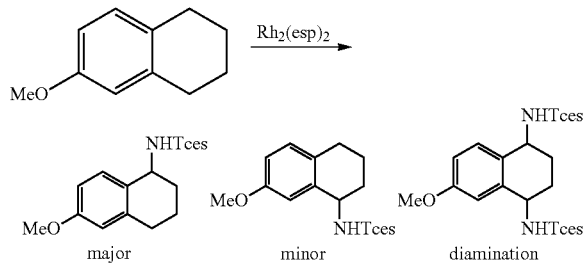

Scheme 13. Rh-catalyzed C—H amination of 6-methoxytetralin.

The purified mixture used from the rhodium reaction to determine the HPLC detection limit contained an 8:1 ratio of the major to minor products along with isolable diamination product. A solution of 5 mg of the major and minor product mixture in 1 mL of acetonitrile was then diluted by a factor of 10 to give 0.5 mg in 1 mL. This solution was again diluted to give a final sample containing 0.05 mg in 1 mL of acetonitrile. A 2 μL sample of this mixture was the concentration at which none of the minor product was detected by HPLC. A Zorbax CN 4.6×250 column with a 1.0 mL/min flow rate was used with a 95:5 hexanes:isopropanol mobile phase.

The diamination product from the rhodium reaction was also isolated but none of this product was detected using the disclosed amination reaction by $^1$H NMR, however a minor peak was detected by HPLC.

The starting material was subjected to the disclosed manganese-catalyzed reaction, then the crude reaction was analyzed by HPLC, and none of the minor product was detected. Due to the high detection limit of the HPLC, it was concluded that the selectivity of the disclosed reaction is at least 20:1 in this case.

Example 9. Experimental Kinetic Data and Methods for Scheme 4

Method for KIE Determination:

The twice column-purified product mixture (ca. 30 mg in 800 μL CDCl$_3$) was analyzed by $^{13}$C NMR (126 MHz instrument). Cr(acac)$_3$ (1.5 mg) was added directly to the solution in the NMR tube immediately prior to running the NMR study; this helps to significantly reduce delay times needed to obtain accurate integrations. The experiment was run under inverse-gated decoupling conditions without sample spinning. The KIE was reported as the area of the deuterated peak over that of the protonated peak. Three identical experiments were run and an average value was calculated with error reported as a standard deviation. Rh$_2$(esp)$_2$ experiments were performed using the previously reported procedure above on the same scale as the [Mn$^{III}$(ClPc)]Cl experiments.

[Mn$^{III}$(ClPc)]SbF$_6$: C—H/C-D=3.00±0.08 (3.00, 2.92, 3.08).

Rh$_2$(esp)$_2$: C—H/C-D=2.60±0.03 (2.60, 2.62, 2.57).

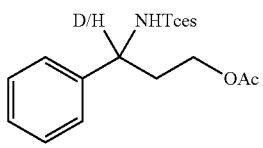

3-phenyl-3-(((2,2,2-trichloroethoxy)sulfonyl)amino) propyl-3-d acetate

According to the general procedure A on 1.5× scale, 3-phenylpropyl acetate (53.8 mg, 0.30 mmol, 1 equiv), benzene (0.60 mL, 0.5M), manganese (III) perchlorophthalocyanine chloride (34.6 mg, 0.030 mmol, 0.1 equiv), silver hexafluoroantimonate (10.3 mg, 0.030 mmol, 0.1 equiv) and 2,2,2-trichloroethyl (phenyl-λ$^3$-iodanylidene)sulfamate (258.3 mg, 0.60 mmol, 2 equiv) were combined in a 10 mL round-bottom flask and stirred for 8 h. After silica plug filtration using diethyl ether as the eluent (30 mL), the solvent was concentrated and the crude brown oil was loaded onto a silica gel column using dichloromethane to quantitatively transfer the product. Flash chromatography using gradient elution (500 mL of 100% dichloromethane then 300 mL of 2% diethyl ether in 98% dichloromethane followed by 300 mL of 5% diethyl ether in 95% dichloromethane) gave the product as a slightly yellow solid. The product was purified again to remove any trace impurities by flash chromatography using gradient elution (500 mL of 100% dichloromethane then 5%-15% ethyl acetate in hexanes) until the product elutes to give a pure white solid after solvent removal.

Scheme 14. Determination of kinetic isotope effect via initial rate.

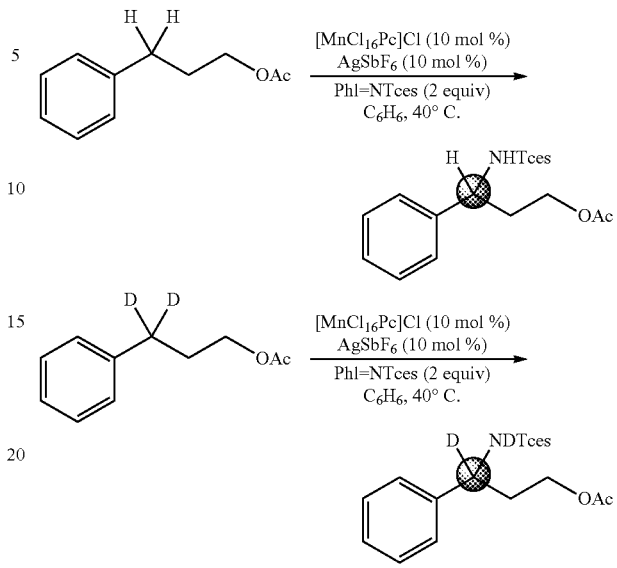

General Procedure for Initial Rate Analysis: All reactions for rate analysis were run on 2× the normal scale. In a 10 mL round bottom flask a Teflon stir bar was added and the flask was sealed with a Suba Seal rubber septum, placed under vacuum, flame-dried for 45 seconds, cooled under a purged and completely air-free argon balloon and wrapped in foil to exclude light. Once cooled, benzene (0.80 mL, 0.5 M to substrate), substrate (0.40 mmol, 1 equiv), and nitrobenzene (24.6 mg, 0.2 mmoles, 0.5 equiv) were added. Manganese (III) perchlorophthalocyanine chloride (46.2 mg, 0.040 mmol, 0.1 equiv) and silver hexafluoroantimonate (13.7 mg, 0.040 mmol, 0.1 equiv) were weighed in a foil wrapped 1-dram vial in the glove box and sealed with a Teflon cap. The vial was removed from the glove box and the contents added directly to the round bottom flask while maintaining an argon atmosphere. In a 1 dram vial open to air, 2,2,2-trichloroethyl (phenyl-λ$^3$-iodanylidene)sulfamate (344 mg, 0.80 mmol, 2 equiv) was weighed and added directly to the round bottom flask while maintaining an argon atmosphere and placed in a 40 OC oil bath. The Suba Seal septum and argon balloon were used to seal the flask throughout the duration of the experiments. Aliquots (50 μL) were taken every 2 minutes from the reaction flask for 14 minutes, and filtered through a silica pad with 1 mL of 80/20 Et$_2$O/CH$_2$Cl$_2$ for HPLC (Zorbax CN, 4.6×250 nm) analysis. The yield was determined by integration of the product peaks relative to the nitrobenzene internal standard and comparison to a standard curve. Yields are reported as the average of three runs with error bars denoting standard deviation. Error for kinetic isotopes was calculated via propagation of the standard error of the mean for each set of rates.

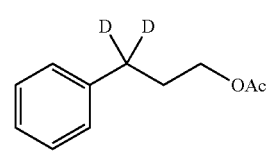 [SMILES: [2H]C([2H])(CCOC(C)=O)c1ccccc1]

3-phenylpropyl-3,3-$d_2$ acetate [1-$d_2$]

$^1$H NMR (400 MHz, Chloroform-d): δ 7.32-7.26 (m, 2H), 7.23-7.17 (m, 3H), 4.09 (t, J=6.6 Hz, 2H), 2.06 (s, 3H), 1.95 (t, J=6.6 Hz, 2H).

[Mn$^{III}$(ClPc)]SbF$_6$: $k_H/k_D$=0.3491/0.1384=2.5±0.2.

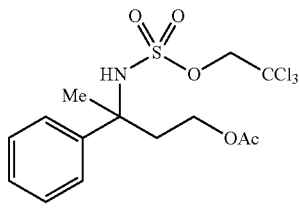

3-phenyl-3-(((2,2,2-trichloroethoxy)sulfonyl)amino) butyl acetate [53]

According to the general amination procedure B, 5 Å powdered molecular sieves (40 mg), 3-phenylbutyl acetate (38.5 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-λ$^3$-iodanylidene)sulfamate (172.2 mg, 0.40 mmol, 2 equiv) were combined in a 10 mL round-bottom flask and stirred for 8 h at 40° C. After silica plug filtration using diethyl ether as the eluent (30 mL), the solvent was concentrated and the crude material was dry loaded onto a silica gel column. Flash chromatography using gradient elution (100% hexanes to 10% ethyl acetate in hexanes) gave the pure product as a slightly discolored oil.

The enantiopure starting material was used for the analysis of stereoretention under [Mn$^{III}$(ClPc)] 4 catalysis using the same procedure described above for the racemic material. Analysis of stereoretention under Rh$_2$(esp)$_2$ catalysis was also performed using a previously reported procedure above.

$^1$H NMR (500 MHz, CDCl$_3$): δ 7.46 (d, J=7.9 Hz, 2H), 7.39 (t, J=7.8 Hz, 2H), 7.30 (t, J=7.3 Hz, 1H), 5.75 (s, 1H), 4.55 (s, 2H), 4.20 (dt, J=12.2, 6.3 Hz, 1H), 3.95 (dt, J=11.7, 6.4 Hz, 1H), 2.40 (td, J=6.4, 1.4 Hz, 2H), 1.93 (s, 3H), 1.89 (s, 3H).

$^{13}$C NMR (126 MHz, CDCl$_3$): δ 171.1, 143.2, 128.9, 128.0, 125.5, 93.6, 78.2, 62.0, 60.9, 40.9, 26.2, 20.9.

HRMS (ESI-TOF MS ES+): m/z calculated for C$_{14}$H$_{18}$NO$_5$SCl$_3$Na [M+Na]$^+$: 439.9869, found 439.9871.

HPLC Analysis: A Chiracel OJ-H 4.6 mm×150 mm column with a 1.0 mL/min flow rate was used with a 94:6 hexanes:isopropanol mobile phase.

Stereoretention study for the intramolecular [Mn(ClPc)] 4 catalyzed C—H amination.

Scheme 15. Mechanistic probes for stereoretention and radical intermediates.

benzylic

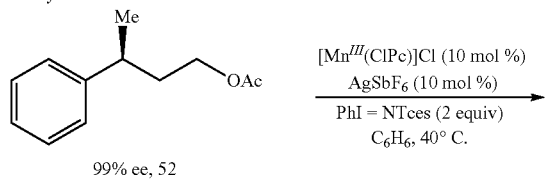

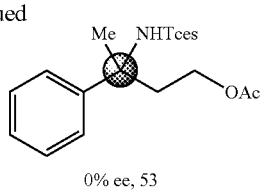

aliphatic

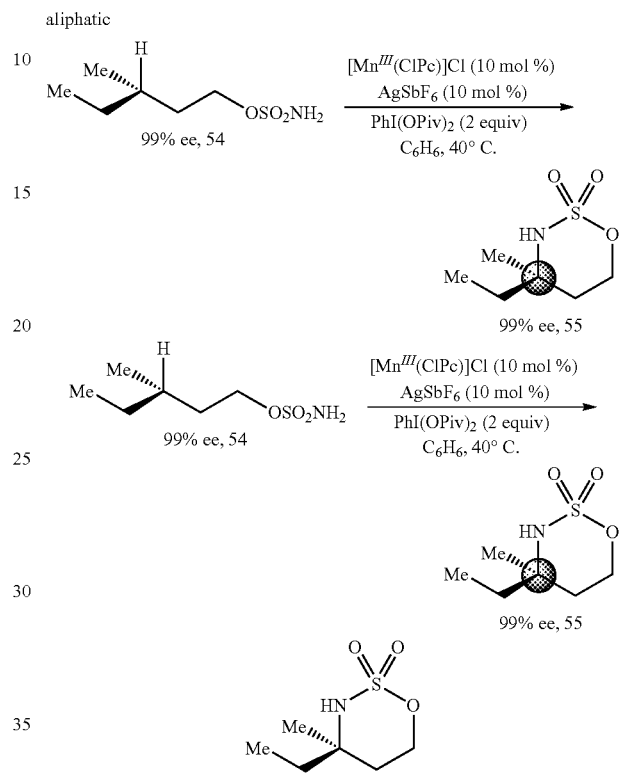

(R)-4-ethyl-4-methyl-1,2,3-oxathiazinane 2,2-dioxide [55]

The same procedure as previously reported above using manganese (III) perchlorophthalocyanine chloride (23.1 mg, 0.020 mmol, 0.1 equiv) instead of [Mn($^t$BuPc)]SbF$_6$ was performed. Similarly, the analysis was performed according to previously reported analytical procedures.

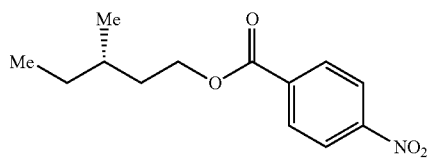 [SMILES: CC[C@H](C)CCOC(=O)c1ccc([N+](=O)[O-])cc1]

(S)-3-methylpentyl 4-nitrobenzoate [S50]

To obtain the enantiopurity of the (S)-(+)-3-methyl-1-pentanol starting material, the alcohol converted to the p-NO$_2$-benzoate derivative and evaluated by HPLC analysis.

$^1$H NMR (500 MHz, CDCl$_3$): 8.29 (d, J=8.9 Hz, 2H), 8.20 (d, J=8.8 Hz, 2H), 4.46-4.35 (m, 2H), 1.91-1.78 (m, 1H), 1.67-1.51 (m, 2H), 1.49-1.35 (m, 1H), 1.33-1.18 (m, 1H), 0.96 (d, J=6.4 Hz, 3H), 0.91 (t, J=7.4 Hz, 3H).

Example 10. Site-Selectivity Probe for Benzylic Sites

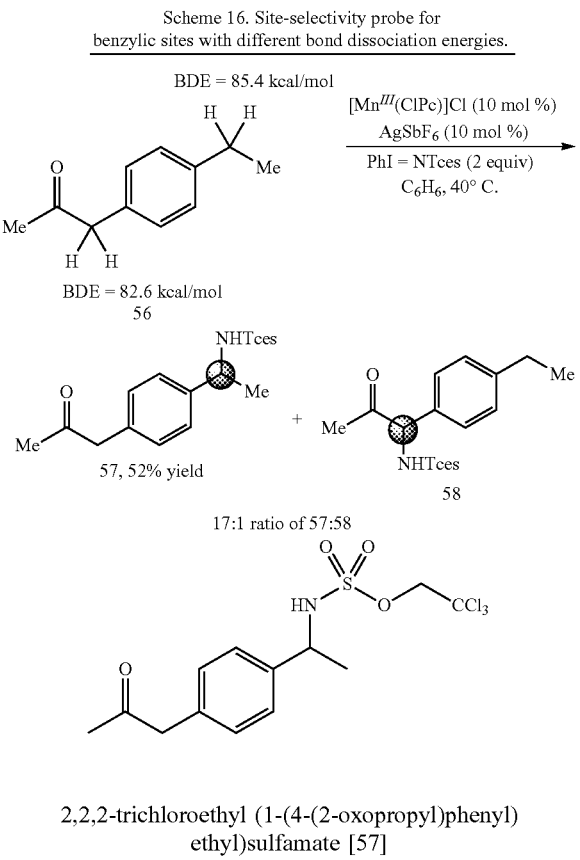

Scheme 16. Site-selectivity probe for benzylic sites with different bond dissociation energies.

2,2,2-trichloroethyl (1-(4-(2-oxopropyl)phenyl)ethyl)sulfamate [57]

According to the general amination procedure B, 5 Å powdered molecular sieves (40 mg), freshly distilled 4-ethylphenylacetone 56 (32.4 mg, 0.20 mmol, 1 equiv), benzene (0.40 mL, 0.5M), manganese (III) perchlorophthalocyanine chloride (23.1 mg, 0.020 mmol, 0.1 equiv), silver hexafluoroantimonate (6.9 mg, 0.020 mmol, 0.1 equiv) and 2,2,2-trichloroethyl (phenyl-$\lambda^3$-iodanylidene)sulfamate (172.2 mg, 0.40 mmol, 2 equiv) were combined in a 10 mL round-bottom flask and stirred for 24 h. After silica plug filtration using diethyl ether as the eluent (30 mL), the solvent was concentrated leaving a crude brown oil. A pipet tip of the crude material was diluted with diethyl ether to 0.8 mL in an HPLC vial. This solution was evaluated to determine the reaction selectivity (see HPLC traces below). The remaining crude material was dry loaded onto a silica gel column. Flash chromatography using gradient elution (400 mL of 5% ethyl acetate in 95% hexanes then 300 mL of 8% ethyl acetate in 92% hexanes, 300 mL of 10% ethyl acetate in 90% hexanes, 300 mL of 12% ethyl acetate in 88% hexanes, 200 mL of 14% ethyl acetate in 86% hexanes then 600 mL of 20% ethyl acetate in 80% hexanes) gave the pure product as a slightly discolored oil.

Run 1 (44 mg, 0.113 mmol, 56% yield, 16.0:1 57:58 selectivity by HPLC).
Run 2 (36 mg, 0.093 mmol, 47% yield, 17.5:1 57:58 selectivity by HPLC).
Run 3 (42 mg, 0.108 mmol, 54% yield, 17.2:1 57:58 selectivity by HPLC).

Average overall yield: 52% yield+4.7, 16.9:1 57:58 selectivity.

A slightly impure $^1$H NMR spectrum is assigned and reported for compound 58 below in the spectra section as full characterization was hampered by inadequate amounts of product.

Characterization Data for Major Regioisomer 57.
$^1$H NMR (500 MHz, CDCl$_3$): δ 7.33 (d, J=8.1 Hz, 2H), 7.21 (d, J=8.1 Hz, 2H), 4.93 (d, J=7.1 Hz, 1H), 4.73 (p, J=6.9 Hz, 1H), 4.46 (d, J=10.8 Hz, 1H), 4.45 (d, J=10.9 Hz, 1H), 3.70 (s, 2H), 2.18 (s, 3H), 1.62 (d, J=6.9 Hz, 3H).
$^{13}$C NMR (126 MHz, CDCl$_3$): δ 206.0, 140.3, 134.4, 130.2, 126.8, 93.5, 78.3, 54.8, 50.5, 29.7, 22.9.
HRMS (ESI-TOF MS ES+): m/z calculated for C$_{13}$H$_{17}$NO$_4$SCl$_3$ [M+H]$^+$: 387.9944, found 387.993.
HPLC Analysis: A Zorbax CN 4.6×250 column with a 1.0 mL/min flow rate was used with an 88:12 hexanes:isopropanol mobile phase.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

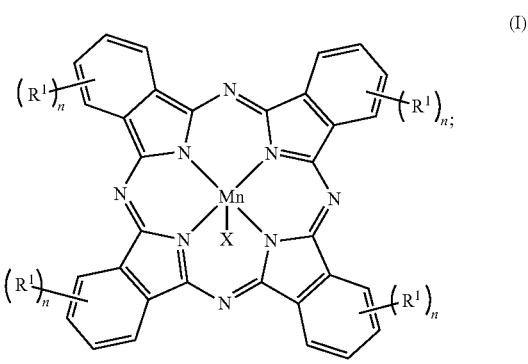

(I)

wherein
X is an anion;
each R$^1$ is independently chloro, bromo, iodo, —C(=O)R$^2$, —S(=O)$_2$R$^3$, —C≡CR$^4$, —CQ$_3$, or —CQ$_2$CQ$_3$;
R$^2$ is H, —CQ$_3$, —(C$_1$-C$_6$)alkyl, OR$^5$, N(R$^5$)$_2$, or phenyl;
R$^3$ is —CQ$_3$, —(C$_1$-C$_6$)alkyl, N(R$^5$)$_2$, or phenyl;
R$^4$ is H, halo, —CQ$_3$, —(C$_1$-C$_6$)alkyl, or phenyl;
Q is choro or fluoro;
each R$^5$ is independently H, or —(C$_1$-C$_6$)alkyl;
n is 3 or 4; and
the oxidation state of Mn is +3;

wherein optionally each phenyl is independently substituted with 1-5 substituents.

2. The compound of claim 1 wherein:
each $R^1$ is independently chloro, bromo, —C(=O)$R^2$, —S(=O)$_2R^3$, —CQ$_3$, or —CQ$_2$CQ.

3. The compound of claim 1 wherein X is halo or SbF$_6$.

4. The compound of claim 1 wherein $R^1$ is chloro.

5. The compound of claim 1 wherein the compound of Formula I is a compound of Formula II:

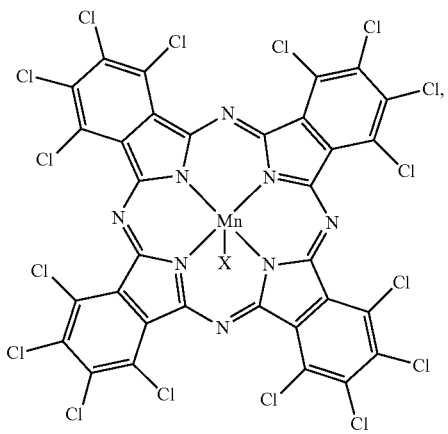

(II)

wherein X is Cl or SbF$_6$.

6. A composition comprising a compound of claim 1 and a salt.

7. The composition of claim 6 wherein the salt is AgSbF$_6$.

8. The composition of claim 6 wherein the compound is 3:

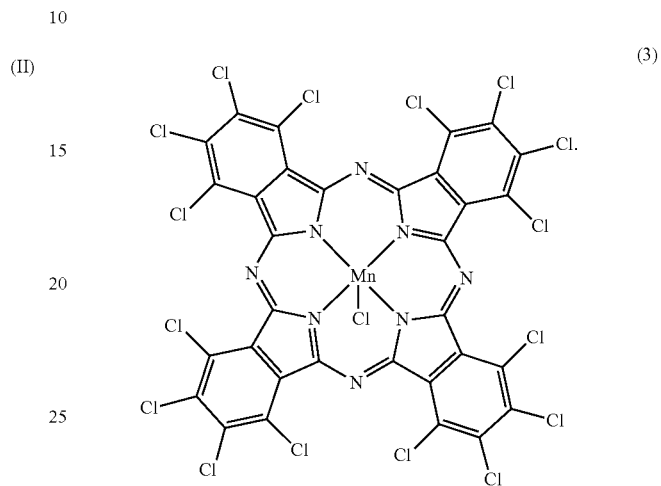

(3)

* * * * *